(12) United States Patent
Nakatsugawa et al.

(10) Patent No.: US 8,558,184 B2
(45) Date of Patent: Oct. 15, 2013

(54) RADIOGRAPHIC IMAGE CAPTURING APPARATUS

(75) Inventors: Haruyasu Nakatsugawa, Ashigarakami-gun (JP); Naoyuki Nishino, Ashigarakami-gun (JP); Naoto Iwakiri, Ashigarakami-gun (JP); Fumito Nariyuki, Ashigarakami-gun (JP); Yasunori Ohta, Ashigarakami-gun (JP); Kazuhiro Noda, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 26 days.

(21) Appl. No.: 13/298,886

(22) Filed: Nov. 17, 2011

(65) Prior Publication Data

US 2012/0126129 A1    May 24, 2012

(30) Foreign Application Priority Data

Nov. 18, 2010    (JP) ................. 2010-258184

(51) Int. Cl.
*G01T 1/20* (2006.01)
(52) U.S. Cl.
USPC ..................... 250/369; 250/363.01
(58) Field of Classification Search
USPC ....................................... 250/369
See application file for complete search history.

(56) References Cited

U.S. PATENT DOCUMENTS

| 7,989,772 | B2 | 8/2011 | Yagi et al. |
| 2002/0014592 | A1* | 2/2002 | Rutten et al. ............ 250/368 |
| 2005/0161610 | A1* | 7/2005 | Spahn ............... 250/370.09 |
| 2006/0180770 | A1* | 8/2006 | Spahn ............... 250/370.11 |
| 2009/0283685 | A1 | 11/2009 | Takeda et al. |
| 2010/0116996 | A1 | 5/2010 | Poorter |

FOREIGN PATENT DOCUMENTS

| JP | 2007-181183 A | 7/2007 |
| JP | 2007-225598 A | 9/2007 |
| JP | 2008-128885 A | 6/2008 |
| JP | 2008-178522 A | 8/2008 |
| JP | 2010-525359 A | 7/2010 |

\* cited by examiner

*Primary Examiner* — Marcus Taningco
(74) *Attorney, Agent, or Firm* — Sughrue Mion, PLLC

(57) ABSTRACT

A radiographic image capturing apparatus includes a photodetector substrate, a scintillator, a switching filter, and a resetting light source, which are arranged successively in this order. If the switching filter is made permeable to resetting light from the resetting light source, the switching filter allows resetting light to be applied to the photodetector substrate through the scintillator, whereas, if the switching filter is made impermeable to the resetting light, the switching filter reflects at least a fluorescence, which is converted from radiation by the scintillator, toward the photodetector substrate.

21 Claims, 32 Drawing Sheets

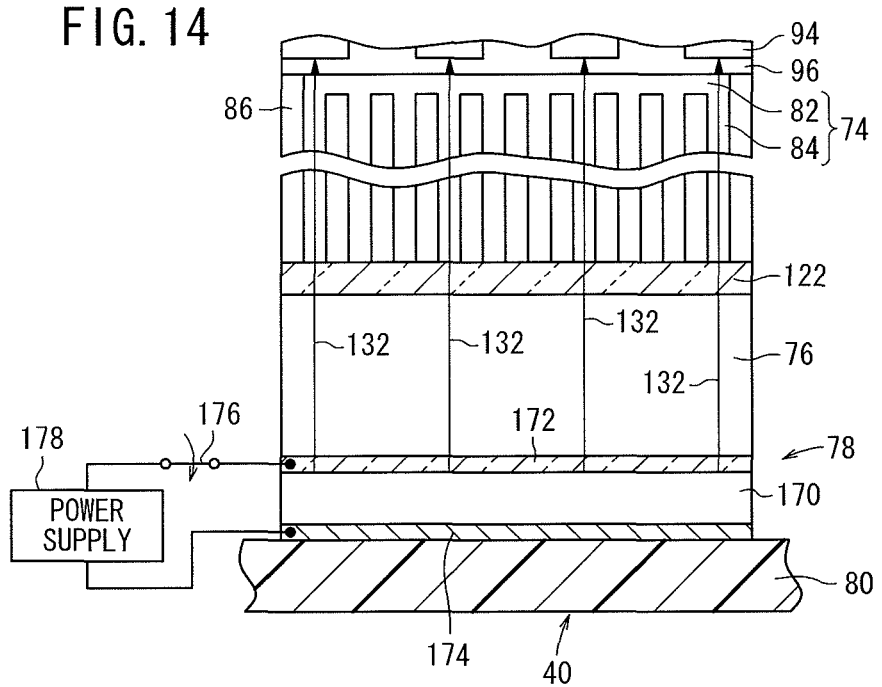

RADIOGRAPHIC IMAGE CAPTURING APPARATUS

CROSS-REFERENCE TO RELATED APPLICATION

This application is based upon and claims the benefit of priority from Japanese Patent Application No. 2010-258184 filed on Nov. 18, 2010, of which the contents are incorporated herein by reference.

BACKGROUND OF THE INVENTION

1. Field of the Invention

The present invention relates to a radiographic image capturing apparatus having a scintillator for converting radiation into fluorescence, and a photodetector substrate for converting the fluorescence into electric signals.

2. Description of the Related Art

In the medical field, it has widely been customary to apply radiation from a radiation source to a subject and detect radiation that has passed through the subject with a radiation detector that makes up part of a radiographic image capturing apparatus, thereby capturing a radiographic image of the subject. The radiographic image capturing apparatus includes a scintillator for converting radiation that has passed through the subject into fluorescence, and a photodetector substrate for converting the fluorescence into electric signals. The photodetector substrate includes photodetector devices, which include photodiodes for detecting the fluorescence.

If the photodiodes of the photodetector devices are made of amorphous silicon (a-Si) or the like, then some of the electric charges (i.e., electrons) that are converted from the fluorescence become temporarily trapped by the impurity level (defect) of the amorphous silicon. If such trapped electrons are subsequently released due to a rise in temperature of the photodiodes, which may be caused at the time a moving image is captured over a long period of time, unwanted current such as dark current tends to be generated, possibly producing noise in a resultant radiographic image of the subject. To solve this problem, as disclosed in Japanese Laid-Open Patent Publication No. 2010-525359 (PCT) and Japanese Laid-Open Patent Publication No. 2007-225598, there has been proposed a light resetting process for reducing noise by applying resetting light to the photodiodes at a time that radiation is not being applied to the subject, i.e., if a radiographic image of the subject is not being captured, to thereby embed electric charges in the impurity level, so that electric charges converted from fluorescence in a case where radiation is applied to the subject, i.e., in a case where a radiographic image of the subject is captured, will not become trapped by the impurity level.

According to Japanese Laid-Open Patent Publication No. 2010-525359 (PCT), a reflective layer having a plurality of small holes therein, a scintillator, and a photodetector substrate, are arranged in this order, and resetting light is applied to light detecting elements of the photodetector substrate through each of the small holes and the scintillator. According to Japanese Laid-Open Patent Publication No. 2007-225598, a reflecting layer, a resetting light source, a scintillator, and a photodetector substrate are arranged in this order, and resetting light emitted from the resetting light source is applied to a photodetector device of the photodetector substrate via the scintillator.

SUMMARY OF THE INVENTION

According to Japanese Laid-Open Patent Publication No. 2010-525359 (PCT), fluorescence converted from radiation by the scintillator is directly applied to the photodetector substrate, or alternatively, is applied to the photodetector substrate after reflection thereof by the reflective layer. However, because a plurality of small holes are provided in the reflective layer, a portion of the fluorescence that reaches the reflective layer escapes through the small holes, and as a result, the light amount of fluorescent light that is applied to the photodetector substrate is reduced, and thus the sensitivity of the photodetector substrate is degraded.

Further, as viewed in plan, shifting in position between the small holes and the light detecting elements tends to occur, or if the light detecting elements are arranged at positions that differ from each of the small holes, the resetting effect is insufficient (charges cannot be embedded sufficiently in the impurity level) even if resetting light is applied to the light detecting elements through the respective small holes. Consequently, if the dose of resetting light is made larger with the goal of obtaining an adequate resetting effect, a problem arises in that unwanted heat may be generated by the resetting light source that outputs the resetting light.

In this manner, with the technique proposed by Japanese Laid-Open Patent Publication No. 2010-525359 (PCT), by providing the reflective layer equipped with a plurality of small holes therein, radiographic images of high sensitivity cannot be obtained, while on the other hand, light-based resetting cannot be carried out adequately.

On the other hand, according to Japanese Laid-Open Patent Publication No. 2007-225598, fluorescence converted from radiation by the scintillator is directly applied to the photodetector substrate, or is reflected by the reflecting layer via the resetting light source, and thereafter is applied to the photodetector substrate via the resetting light source and the scintillator. However, since such fluorescence, which is reflected by the reflecting layer, passes through the resetting light source, blurring of radiographic images tends to occur easily.

It is an object of the present invention to provide a radiographic image capturing apparatus, which is capable of sufficiently applying resetting light to a photodetector substrate, of suppressing the occurrence of blurring in captured radiographic images, and of increasing the sensitivity of the photodetector substrate with respect to fluorescence.

To achieve the above object, there is provided in accordance with the present invention a radiographic image capturing apparatus comprising:

a scintillator for converting radiation into fluorescence;

a photodetector substrate for converting the fluorescence into electric signals;

a resetting light source for applying resetting light a switching filter, which is selectively permeable and impermeable to the resetting light, wherein the photodetector substrate, the scintillator, the switching filter, and the resetting light source are arranged in this order, and if the switching filter is made permeable to the resetting light, the switching filter allows the resetting light to be applied to the photodetector substrate through the scintillator, and if the switching filter is made impermeable to the resetting light, the switching filter reflects at least the fluorescence toward the photodetector substrate.

With the above arrangement, if the switching filter is switched to a permeable state with respect to the resetting light, the resetting light source can apply the resetting light to the photodetector substrate through the switching filter and the scintillator for sufficiently performing a light resetting process on the photodetector substrate.

If the switching filter is switched to an impermeable state with respect to the resetting light, among the fluorescence converted from the radiation by the scintillator, part of such fluorescence that travels toward the resetting light source is reflected toward the photodetector substrate by the switching filter. Therefore, the reflected light travels through the scintillator and is applied to the photodetector substrate without reaching the resetting light source. Consequently, high-quality radiographic images that are not blurred can be acquired, and the amount of fluorescence applied to the photodetector substrate can be increased, thereby increasing the sensitivity of the photodetector substrate with respect to fluorescence.

In this manner, according to the present embodiment, since the photodetector substrate, the scintillator, the switching filter, and the resetting light source are successively arranged in this order, and the switching filter can be made selectively permeable and impermeable to the resetting light, the light resetting process can sufficiently be performed on the photodetector substrate, blurring of radiographic images can be suppressed, and in addition, the sensitivity of the photodetector substrate with respect to fluorescence can be increased.

The scintillator converts radiation, which has passed through a subject, into fluorescence. The photodetector substrate converts the fluorescence into electric signals, which represent a radiographic image of the subject. The switching filter is selectively switchable to a transparent state (permeable state), which is permeable to the resetting light, and a mirror state (impermeable state), which reflects the fluorescence toward the photodetector substrate and also reflects the resetting light toward the resetting light source, based on an image capturing order concerning capturing of the radiographic image of the subject.

The switching filter can be kept in the transparent state or the mirror state, or can be switched to the transparent state or the mirror state, depending on an image capturing method (a still image capturing mode or a moving image capturing mode) for the subject, for thereby reliably and efficiently performing the light resetting process on the photodetector substrate, and for acquiring, with high sensitivity, high-quality radiographic images that are prevented from becoming blurred. If the switching filter in the mirror state reflects the fluorescence toward the photodetector substrate, the amount of fluorescence that is applied to the photodetector substrate is increased. Consequently, the amount of radiation that is applied to the subject can be reduced in order to reduce the dose of radiation applied to the subject.

More specifically, it is desirable for the radiographic image capturing apparatus to keep the switching filter in the transparent state or in the mirror state, or switch the switching filter to the transparent state or to the mirror state according to an image capturing order, as described below in cases [1] through [9].

[1] If the image capturing order includes a still image capturing mode for capturing at least one still image, or a moving image capturing mode at a frame rate lower than a frame rate threshold value, the switching filter is kept in the mirror state.

The above image capturing modes, in particular, require high-quality radiographic images to be acquired with high sensitivity. Since the image capturing interval in the aforementioned image capturing modes is relatively long, the temperature of the photodiodes does not rise significantly, and noise caused by electric charges, which are trapped by the impurity level, being discharged again is not expected to greatly affect the captured radiographic images.

If the above image capturing order is received, the switching filter is kept in the mirror state to hold the light resetting process off and also to reflect the fluorescence converted from radiation by the scintillator toward the photodetector substrate, thereby increasing the amount of fluorescence applied to the photodetector substrate. As a result, in case [1], it is possible to easily acquire low-noise, high-quality radiographic images with high sensitivity in which blurring of the radiographic images is suppressed.

[2] If the image capturing order includes a moving image capturing mode, the switching filter is kept in the transparent state.

In the case of a moving image capturing mode, by capturing of images over a prolonged period of time, the temperature of the photodiodes increases, and it is expected that noise, which is caused by re-discharging of electric charges that are trapped by the impurity level, will adversely influence the radiographic images significantly. Accordingly, by maintaining the transparent state of the switching filter, it is possible to carry out light resetting at a time that radiation is not being applied between capturing of radiographic images, and as a result, noise in the radiographic images can be reduced.

[3] If the image capturing order includes a moving image capturing mode, the switching filter is kept in the mirror state in each frame while the subject is irradiated with radiation, and is kept in the transparent state if the subject is not irradiated with radiation, whereby the switching filter is switched successively between the mirror state and the transparent state.

In this case, since the switching filter is switched successively between the mirror state and the transparent state in one frame, if the subject is irradiated with radiation, the switching filter is kept in the mirror state to reflect fluorescence reliably toward the photodetector substrate, thereby increasing the amount of fluorescence applied to the photodetector substrate. Further, if the subject is not irradiated with radiation, because the switching filter is kept in the transparent state, the light resetting process can be performed sufficiently with respect to the photodetector substrate.

In this manner, in the moving image capturing mode, therefore, the switching filter is switched alternately between the mirror state and the transparent state in one frame, to thereby acquire high-quality radiographic images with high sensitivity, and also to reduce noise in the acquired radiographic images. It is necessary for a switching filter of this type to have a switching time that can sufficiently catch up with the frame rate of the moving image capturing mode, i.e., for the switching filter to have a switching time shorter than a time interval between image capturing cycles. Accordingly, with a switching filter that does not have a switching time capable of sufficiently catching up with the frame rate, preferably, the aforementioned case [2] may be applied.

[4] If the image capturing order includes a moving image capturing mode and a still image capturing mode for capturing at least one still image, the switching filter is kept in a transparent state in the moving image capturing mode, and is kept in the mirror state in the still image capturing mode, and further is switched from the transparent state to the mirror state at a timing at which the moving image capturing mode is switched to the still image capturing mode, or the switching filter switches from the mirror state to the transparent state at a timing at which the still image capturing mode is switched to the moving image capturing mode.

In this manner, by switching the state of the switching filter at a timing at which switching takes place between the image capturing methods, i.e., the still image capturing mode and the moving image capturing mode, it is possible to reliably acquire optimum radiographic images corresponding to the image capturing method.

[5] If the image capturing order includes a moving image capturing mode at a frame rate higher than a frame rate threshold value, and a still image capturing mode for capturing at least one still image, the switching filter is kept in the mirror state during the still image capturing mode, is further kept in the mirror state during application of radiation with respect to the subject in each frame during the moving image capturing mode, and is kept in the transparent state while radiation is not being applied with respect to the subject, whereby switching between the mirror state and the transparent state is carried out successively, and the switching filter is switched to the mirror state from a state in which the switching filter is switched successively between the mirror state and the transparent state at a timing at which the moving image capturing mode is switched to the still image capturing mode, or is switched from the mirror state to the state in which the switching filter is switched successively between the mirror state and the transparent state at a timing at which the still image capturing mode is switched to the moving image capturing mode.

Even with this type of image capturing order, because the state of the switching filter can reliably be switched at a timing at which the image capturing methods are switched, it is also possible to reliably acquire optimum radiographic images corresponding to the image capturing method.

The frame rate threshold value refers to a threshold value for determining whether the light resetting process is required or not. If the frame rate of a moving image capturing mode included in the image capturing order is higher than the frame rate threshold value, then it is determined that the light resetting process is required. On the other hand, if the frame rate of a moving image capturing mode included in the image capturing order is lower than the frame rate threshold value, then it is determined that the light resetting process is not required.

Consequently, if a moving image capturing mode has a frame rate higher than the frame rate threshold value, thus requiring the light resetting process, and if the switching filter is capable of switching between the mirror state and the transparent state in a manner to catch up with the frame rate, then the switching filter is switched successively between the mirror state and the transparent state in one frame, thereby making it possible to perform the light resetting process reliably between image capturing cycles while the subject is not irradiated with radiation.

[6] If the image capturing order includes a first moving image capturing mode at a frame rate lower than a frame rate threshold value and a second moving image capturing mode at a frame rate higher than the frame rate threshold value, the switching filter is kept in the mirror state during the first moving image capturing mode, and is kept in the transparent state during the second image capturing mode, and the switching filter switches from the mirror state to the transparent state at a timing at which the first moving image capturing mode is switched to the second moving image capturing mode, or switches from the transparent state to the mirror state at a timing at which the second moving image capturing mode is switched to the first moving image capturing mode.

Therefore, even if the image capturing order has a frame rate thereof changed during the radiographic image capturing process, assuming that the state of the switching filter is switched at a timing at which the frame rate is changed, optimum radiographic images corresponding to the frame rate can reliably be acquired.

[7] If the image capturing order includes the aforementioned first moving image capturing mode and the aforementioned second moving image capturing mode, the switching filter is kept in the mirror state in the first moving image capturing mode, and the switching filter is kept in the mirror state if the subject is irradiated with radiation and is kept in the transparent state if the subject is not irradiated with radiation in each frame, whereby the switching filter is switched successively between the mirror state and the transparent state in the second moving image capturing mode, and the switching filter switches from the mirror state to successively switching between the mirror state and the transparent state at a timing at which the first moving image capturing mode is switched to the second moving image capturing mode, or switches from successively switching between the mirror state and the transparent state to the mirror state at a timing at which the second moving image capturing mode is switched to the first moving image capturing mode.

Even with the image capturing order of case [7], which is similar to the case of [6], has a frame rate thereof changed during the radiographic image capturing process, optimum radiographic images corresponding to the frame rate can reliably be acquired by switching the switching filter at the timing at which the frame rate is changed.

[8] If the image capturing order includes the aforementioned first moving image capturing mode and the aforementioned second moving image capturing mode, if the image capturing order includes an image capturing sequence in order of the first image capturing mode and the second image capturing mode, the switching filter is switched to the transparent state after the mirror state has been maintained until a predetermined frame in the first image capturing mode, and then maintains the transparent state for any remaining frames after switching and in the second image capturing mode, and if the image capturing order includes an image capturing sequence in order of the second image capturing mode and the first image capturing mode, the switching filter is switched to the mirror state after the transparent state has been maintained in the second image capturing mode and until a predetermined frame in the first image capturing mode, and then maintains the mirror state for any remaining frames after switching.

In view of the fact that time is required for switching between the mirror state and the transparent state, cases may occur in which switching between the mirror state and the transparent state cannot be performed smoothly at the timing at which the first image capturing mode and the second image capturing mode are changed. Thus, in the foregoing manner, by performing switching between the mirror state and the transparent state in between frames in the first image capturing mode at which the frame rate is low, during the second image capturing mode, superimposition of noise in the radiographic image caused by re-discharging of electric charges that are trapped by the impurity level can reliably be avoided.

[9] If the image capturing order indicated in cases [6] through [8] above further includes a still image capturing mode for capturing at least one still image, the switching filter is kept in the mirror state in the still image capturing mode, and switches from a state in which the switching filter corresponds to the moving image capturing modes to the mirror state, at a timing at which the moving image capturing mode is switched to the still image capturing mode, or switches from the mirror state to the state in which the switching filter corresponds to the moving image capturing mode, at a timing at which the still image capturing mode is switched to the moving image capturing mode.

Accordingly, even if the image capturing order includes a still image capturing mode, optimum radiographic images can easily be acquired in each of the image capturing modes by switching the switching filter as described above.

In the aforementioned radiographic image capturing apparatus, the photodetector substrate includes a plurality of photodetector devices for converting fluorescence into electric signals, and the switching filter has a window defined in a portion thereof for passing resetting light therethrough at all times. If the resetting light source applies the resetting light through the window to one of the photodetector devices, which faces toward the window, the photodetector device, which is irradiated with resetting light, detects a dark current signal generated by the resetting light, and the switching filter switches to the mirror state or the transparent state based on a temperature of the photodetector device depending on the dark current signal and the image capturing order.

The level of noise trapped by an impurity level varies with the temperature of the photodetector devices, which are in the form of photodiodes made of a-Si or the like. Noise can thus be efficiently reduced depending on changes in the temperature of the photodetector devices by switching the switching filter to the mirror state or the transparent state based on the temperature, which depends on the dark current signal and the image capturing order, as described above.

Preferably, the switching filter includes a light-regulating mirror film layer, which is electrically controlled to be permeable or impermeable to the resetting light. The switching filter includes a transparent base permeable to the resetting light, and the light-regulating mirror film layer is disposed on the transparent base. The scintillator is disposed on a side of the light-regulating mirror film layer, and the resetting light source is disposed on a side of the transparent base. Therefore, the switching filter can easily and efficiently be switched to the permeable state or the impermeable state (mirror state).

Further, the resetting light source may comprise an array of light-emitting elements, a backlight, or an electroluminescent light source, disposed in facing relation to the photodetector substrate with the switching filter and the scintillator interposed therebetween.

The backlight comprises a light guide plate disposed on a side of the switching filter remote from the scintillator, a light source disposed on a side of the light guide plate, a reflective sheet disposed in surrounding relation to the light guide plate and the light source, and a diffusion sheet disposed on a surface of the light guide plate, which faces toward the switching filter. The light source applies light to the light guide plate, and the light applied to the light guide plate is repeatedly reflected in the light guide plate between surfaces of the reflective sheet and the diffusion sheet, and thereafter, the light is emitted as resetting light from the diffusion sheet to the switching filter.

In this manner, the backlight makes it possible to place the light source in an area that is not irradiated with radiation. Therefore, the light source is prevented from becoming degraded by radiation. The light source may comprise a light-emitting diode or a cold-cathode ray tube.

Further, if the resetting light source is in the form of an organic electroluminescent light source, then the resetting light source may be made low in profile.

In the above radiographic image capturing apparatus, the scintillator and the photodetector substrate may be bonded to each other by a bonding layer, the scintillator and the photodetector substrate may be adhered to each other by an adhesive layer, or the scintillator may be directly deposited on the photodetector substrate as a film.

In this case, after the scintillator has been deposited as a film on a vapor deposition substrate, a distal end portion of the scintillator and the photodetector substrate may be bonded to each other by the bonding layer or adhered to each other by the adhesive layer.

In the event that the vapor deposition substrate is non-transparent with respect to resetting light, after the scintillator has been deposited as a film through a peel-off layer on the vapor deposition substrate, the distal end portion of the scintillator and the photodetector substrate may be bonded to each other by the bonding layer or adhered to each other by the adhesive layer, and thereafter, the peel-off layer and the vapor deposition substrate can be peeled off from the scintillator, and the resetting light source may be arranged on the peeled-off surface of the scintillator.

On the other hand, in the event that the vapor deposition substrate is transparent to resetting light, the resetting light source can be disposed on the substrate with the vapor deposition substrate remaining therebetween.

The photodetector substrate may include a photodetector device for converting fluorescence into electric signals, and a switching element for reading the electric signals from the photodetector device. The photodetector device may be made of an organic photoelectric converter material or an amorphous oxide semiconductor, and the switching element may be made of an organic semiconductor material, an amorphous oxide semiconductor, or carbon nanotubes. Thus, the photodetector device and the switching device can be deposited as films at low temperature.

The radiographic image capturing apparatus may further comprise an oblique light blocking layer for blocking fluorescence or resetting light that travels obliquely to a direction in which radiation is applied, the oblique light blocking layer being interposed between the photodetector substrate and the scintillator. It is thus possible to increase the sensitivity of the photodetector substrate with respect to fluorescence and to prevent the radiographic images from becoming blurred.

The photodetector substrate, the scintillator, the switching filter, and the resetting light source, are successively arranged in this order, or alternatively, the resetting light source, the switching filter, the scintillator, and the photodetector substrate are successively arranged in this order, along a direction in which radiation is applied.

If the resetting light source, the switching filter, the scintillator, and the photodetector substrate are successively arranged in this order along the direction in which radiation is applied, the switching filter may be kept in a mirror state, for thereby reflecting the resetting light toward the resetting light source while reflecting the fluorescence toward the photodetector substrate, at least at times that the radiation is applied.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 14 is a cross-sectional view showing a switching filter and a resetting light source;

DESCRIPTION OF THE PREFERRED EMBODIMENTS

Radiographic image capturing apparatus according to preferred embodiments of the present invention will be described in detail below with reference to FIGS. 1 through 32B.

Arrangement of the First Embodiment

Figure 1:
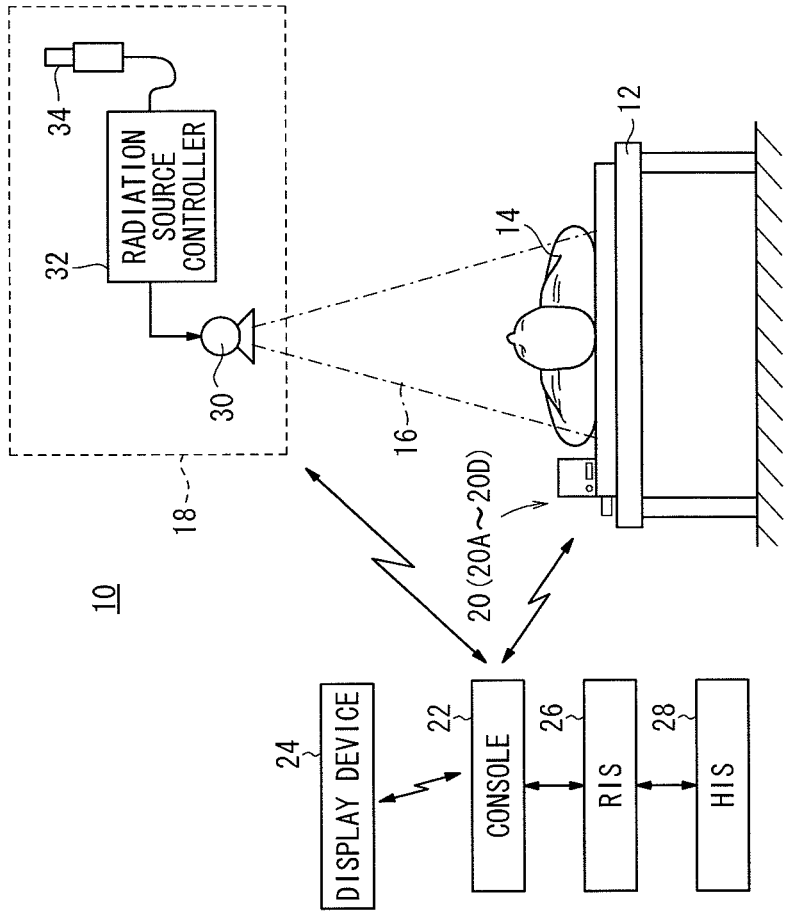
FIG. 1 is a schematic view, partially in block form, of a radiographic image capturing system, which incorporates therein an electronic cassette (radiographic image capturing apparatus) according to a first embodiment of the present invention.

FIG. 1 is a schematic view, partially in block form, of a radiographic image capturing system 10 incorporating therein an electronic cassette (radiographic image capturing apparatus) 20 according to a first embodiment of the present invention.

As shown in FIG. 1, the radiographic image capturing system 10 includes a radiation output device 18 for applying radiation 16 to a subject 14 such as a patient lying on an image capturing base 12 such as a bed or the like, an electronic cassette 20 for detecting radiation 16 that has passed through the subject 14 and converting the detected radiation into a radiographic image, a console 22 for controlling the radiographic image capturing system 10 in its entirety and receiving input actions from a doctor or radiological technician (hereinafter referred to as a "doctor"), and a display device 24 for displaying captured radiographic images, etc.

The radiation output device 18, the electronic cassette 20, the console 22, and the display device 24 send and receive signals to and from each other by way of a wireless LAN according to standards such as UWB (Ultra-Wide Band), IEEE802.11.a/b/g/n., or the like, or wireless communications using milliwaves. The radiation output device 18, the electronic cassette 20, the console 22, and the display device 24 may also send and receive signals to and from each other by way of wired communications through cables.

The console 22 is connected to a radiology information system (RIS) 26, which generally manages radiographic image information and other information handled by the radiological department of a hospital. The RIS 26 is connected to a hospital information system (HIS) 28, which generally manages medical information in the hospital.

The radiation output device 18 has a radiation source 30 for emitting radiation 16, a radiation source controller 32 for controlling the radiation source 30, and a radiation switch 34. Radiation 16, which is emitted from the radiation source 30, may be X-rays, α-rays, β-rays, γ-rays, an electron beam, or the like. The radiation switch 34 can be pushed in two strokes, i.e., the radiation switch 34 can be pushed in a half stroke and a full stroke. If the radiation switch 34 is pushed in a half stroke by the doctor, the radiation switch 34 sends signals to the radiation source controller 32 to prepare the radiation source 30 to emit radiation 16. If the radiation switch 34 is pushed in a full stroke, the radiation switch 34 sends signals to the radiation source controller 32 to enable the radiation source 30 to start emitting radiation 16.

Since the radiation output device 18, the electronic cassette 20, the console 22, and the display device 24 can send and receive signals to and from each other, the radiation output device 18 can send a signal indicating that the radiation source 30 is being made ready to emit radiation 16 to the console 22 if the radiation switch 34 is pushed in a half stroke by the doctor, and may send a signal indicating that the radiation source 30 is capable of emitting radiation 16 to the console 22 if the radiation switch 34 is pushed in a full stroke by the doctor.

Figure 2:
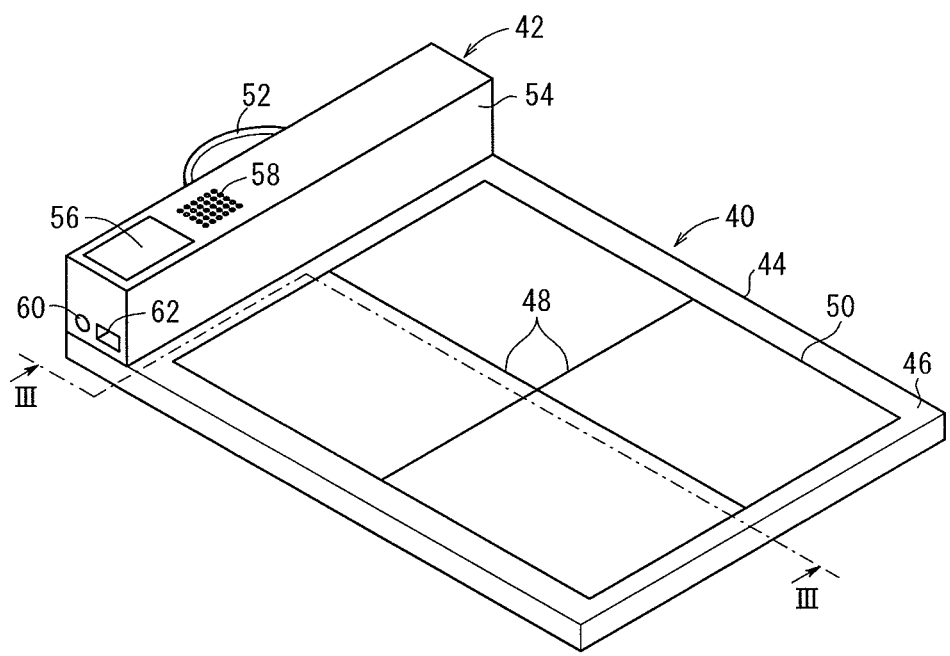
FIG. 2 is a perspective view of the electronic cassette shown in FIG. 1.
Figure 3A:
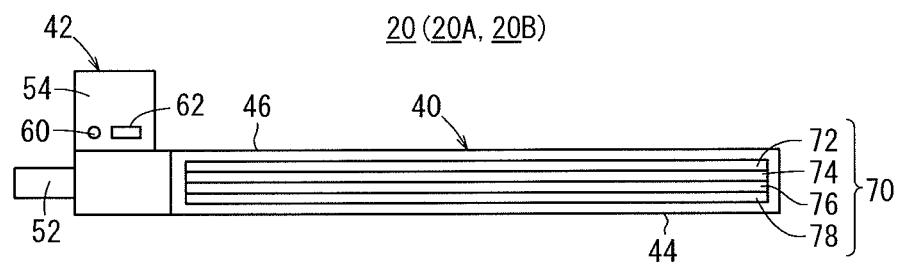
FIGS. 3A and 3B are cross-sectional views of the electronic cassette shown in FIG. 2, taken along line III-III of FIG. 2.
Figure 3B:
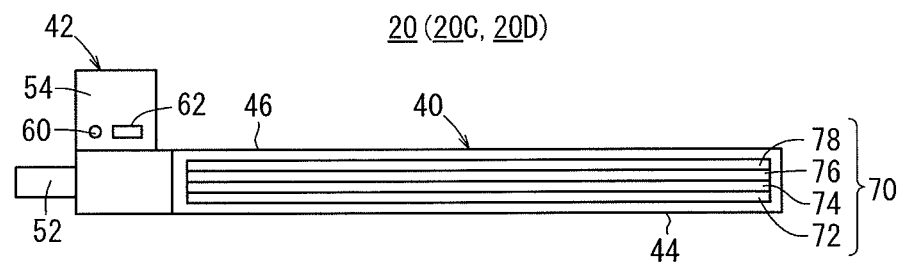

FIG. 2 is a perspective view of the electronic cassette 20 shown in FIG. 1, and FIGS. 3A and 3B are cross-sectional views of the electronic cassette 20 shown in FIG. 2, taken along line III-III of FIG. 2.

The electronic cassette 20 has a panel 40 and a controller 42 disposed on the panel 40. The panel 40 is thinner than the controller 42.

The panel 40 includes a substantially rectangular casing 44 made of a material that is permeable to radiation 16 (see FIG. 1). The panel 40 has an upper irradiation surface 46, which is irradiated with radiation 16. The irradiation surface 46 has guide lines 48 disposed substantially centrally thereon, which serve as a reference for an image capturing area and an image capturing position for the subject 14. The guide lines 48 include an outer frame representing an image capturing area 50, which indicates an irradiation field to be irradiated with radiation 16 on the irradiation surface 46. The guide lines 48 have a central position, in a central region of the image capturing area 50, where the guide lines 48 cross each other in a crisscross pattern.

The electronic cassette 20 also has a grip 52 on a side thereof close to the controller 42 for the doctor to hold. The doctor can hold the grip 52 and carry the electronic cassette 20 to a desired location, e.g., the image capturing base 12. Thus, the electronic cassette 20 serves as a portable radiographic image capturing apparatus.

The controller 42 includes a substantially rectangular casing 54 made of a material that is impermeable to radiation 16. The casing 54 extends along an end of the irradiation surface 46, and the controller 42 is disposed on the irradiation surface 46 outside of the image capturing area 50. The casing 54 has on an upper surface thereof a display control panel 56 in the form of a touch panel for the doctor to enter various items of information, and a speaker 58 for outputting sounds representing various notices for the doctor. The casing 54 also has on a side surface thereof an AC adapter input terminal 60 supplied with charging electric power from an external power source, and an USB terminal 62 serving as an interface for sending and receiving information to and from an external device such as the console 22, for example.

As shown in FIGS. 3A and 3B, the casing 44 houses therein a radiation detector 70 for converting radiation 16 into a radiographic image.

The radiation detector 70 comprises an indirect-conversion-type radiation detector including a photodetector substrate 72, a scintillator 74, a switching filter 76, and a resetting light source 78 arranged in this order.

Figure 11A:
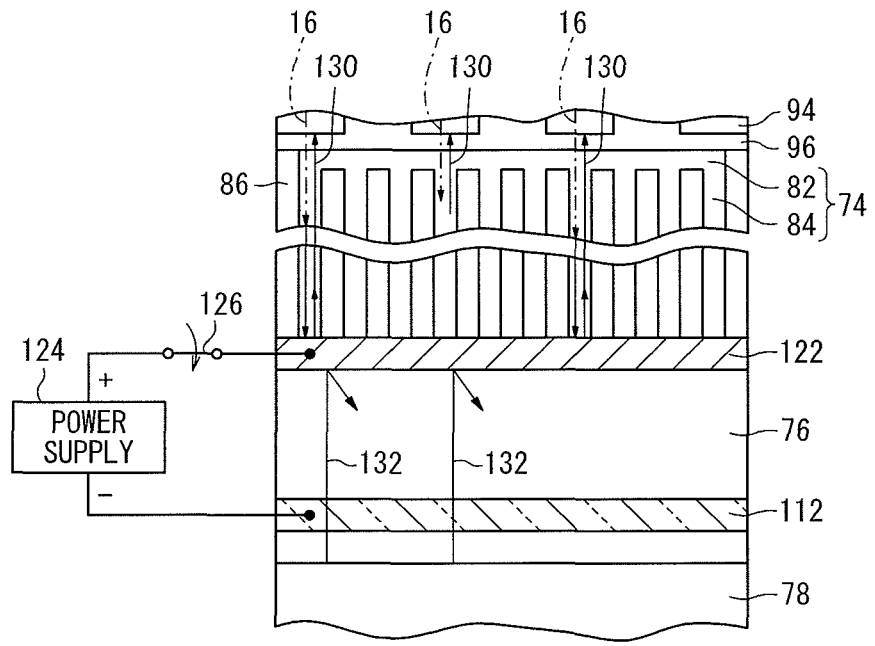
FIGS. 11A and 11B are cross-sectional views showing the manner in which the switching filter is brought into a mirror state.
Figure 11B:
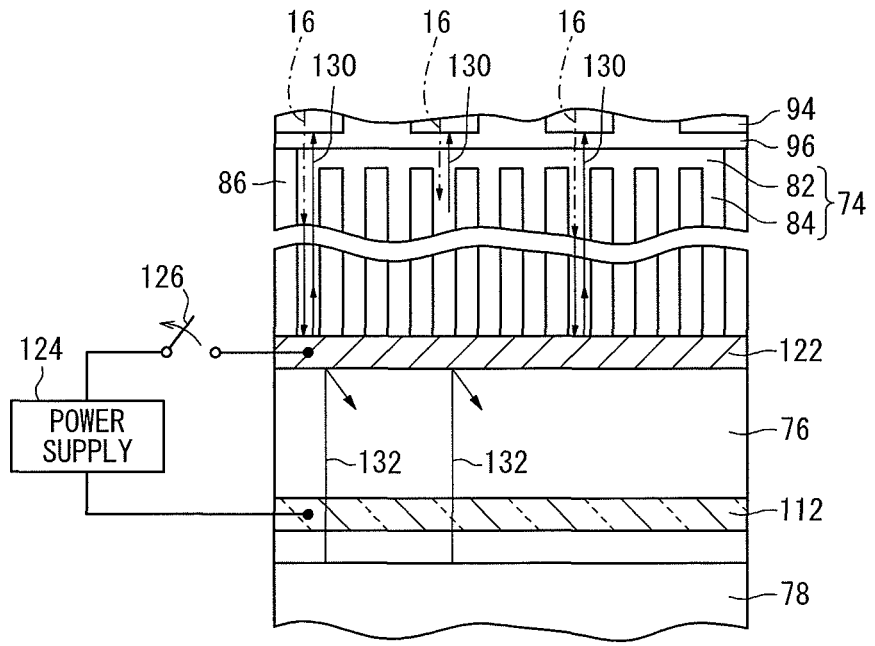

The scintillator 74 converts radiation 16 that has passed through the subject 14 into fluorescence, e.g., fluorescence in the visible range or the ultraviolet range. In FIGS. 11A and 11B to be described later, the scintillator 74 converts radiation 16 into visible light 130. In the description below, it is assumed that the scintillator 74 converts radiation 16 into visible light 130, unless otherwise noted.

The photodetector substrate 72 converts visible light 130, as fluorescence, into electric signals. The resetting light source 78 applies resetting light 132 (see FIGS. 10A through 12B, FIG. 13B, and FIG. 14) to the photodetector substrate 72 in order to reset the photodetector devices 94 (see FIGS. 6A through 8) of the photodetector substrate 72. The switching filter 76 is able to selectively switch between a transmitting state in which the switching filter 76 passes resetting light 132 therethrough, and a blocking state in which the switching filter 76 blocks resetting light 132 against transmission.

The electronic cassette 20 according to the present embodiment is available as different electronic cassettes according to four examples, i.e., as electronic cassettes 20A through 20D according to first through fourth examples, depending on the order in which the photodetector substrate 72, the scintillator 74, the switching filter 76, and the resetting light source 78 are arranged along the direction in which radiation 16 is applied.

FIG. 3A shows the electronic cassettes 20A, 20B according to the first and second examples. Each of the electronic cassettes 20A, 20B is an indirect-conversion-type radiographic image capturing apparatus, in which the radiation detector 70 is an ISS (Irradiation Side Sampling) type, i.e., a face-side readout type, which includes the photodetector substrate 72, and the scintillator 74, the switching filter 76, and the resetting light source 78, which are arranged successively in this order along the direction in which radiation 16 is applied (see FIGS. 1, and 4A through 5B).

FIG. 3B shows the electronic cassettes 20C, 20D according to third and fourth examples. Each of the electronic cassettes 20C, 20D is an indirect-conversion-type radiographic image capturing apparatus, in which the radiation detector 70 is a PSS (Penetration Side Sampling) type, i.e., a reverse-readout type, which includes the resetting light source 78, the switching filter 76, the scintillator 74 and the photodetector substrate 72, which are arranged successively in this order along the direction in which radiation 16 is applied.

Basic structural details of the electronic cassettes 20A through 20D according to the first through fourth examples will be described below, respectively, with reference to FIGS. 4A through 5B. FIGS. 4A through 5B are fragmentary cross-sectional views of the electronic cassettes 20A through 20D in the vicinity of the radiation detector 70 in the casing 44.

In each of the electronic cassettes 20A through 20D according to the first through fourth examples, the radiation detector 70 is disposed between the irradiation surface 46, as a top plate and a bottom plate 80, on a bottom side remote from the irradiation surface 46. The electronic cassettes 20A through 20D are different from each other in the following ways.

Figure 4A:
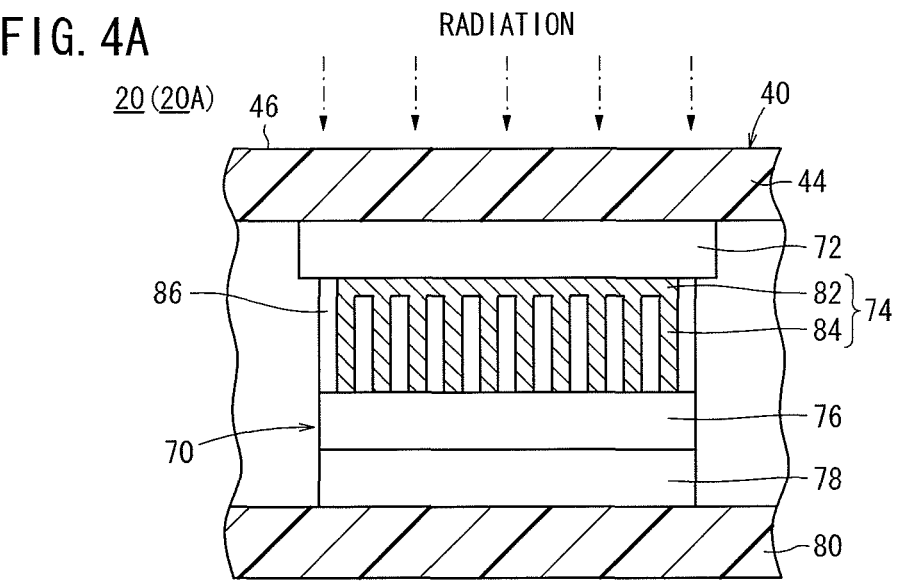
FIGS. 4A and 4B are enlarged fragmentary cross-sectional views of the electronic cassette (electronic cassettes according to a first example and a second example) shown in FIG. 3A in the vicinity of a radiation detector thereof.

In the electronic cassette 20A according to the first example, as shown in FIG. 4A, the scintillator 74 is deposited on a bottom plate 80 of a photodetector substrate 72. More specifically, the scintillator 74 is formed as strips of a columnar crystalline structure 84 by depositing CsI:Tl (cesium iodide with added thallium), for example, by vacuum vapor deposition, on the side of the bottom plate 80 of the photodetector substrate 72. The scintillator 74 includes a proximal end portion located near the photodetector substrate 72, serving as a non-columnar crystalline portion 82.

The columnar crystalline structure 84 includes columns, which extend in a direction substantially perpendicular to the photodetector substrate 72, i.e., in a vertical direction in FIG. 4A along which radiation 16 is applied, with certain gaps being present between adjacent ones of the columns. Since the columnar crystalline structure 84, particularly the non-columnar crystalline portion 82, is vulnerable to moisture, the scintillator 74 of CsI (CsI:Tl) is sealed by a light-permeable moisture-resistant protective layer 86 made of polyparaxylylene resin (Parylene: registered trademark). In FIG. 4A and certain subsequent figures, the gaps between the columns of the columnar crystalline structure 84 are shown as exaggerated for enabling easier understanding of the present invention.

Further, visible light 130 (see FIGS. 11A and 11B) emitted by the scintillator 74 should preferably be in a wavelength range from 360 nm to 830 nm, and more preferably, should include a wavelength range of the color green in order to make it possible for the radiation detector 70 to capture monochromatic radiographic images. In particular, CsI:Tl has an emission spectrum in a wavelength range from 420 nm to 700 nm upon being irradiated with radiation 16, with an emission peak wavelength of 565 nm in the visible range.

Figure 4B:
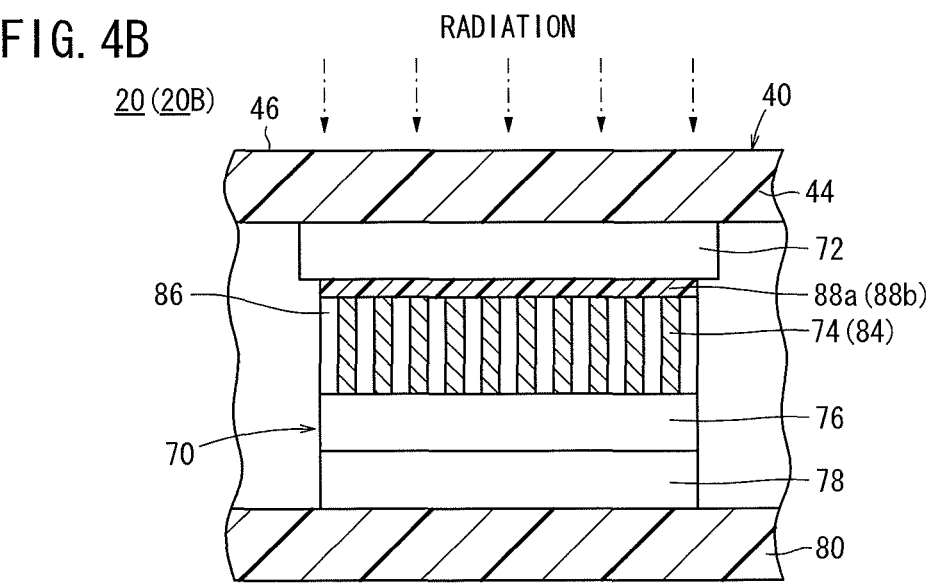

As shown in FIG. 4B, the electronic cassette 20B according to the second example differs from the electronic cassette 20A according to the first example, in that the scintillator 74 and the photodetector substrate 72 are maintained in close contact with each other through a bonding layer 88a or an adhesive layer 88b, which is transparent to visible light 130 as well as to resetting light 132 (see FIGS. 10A through 12B).

In this case, for example, the scintillator 74 is vapor deposited on a later-described vapor deposition substrate 240 (see FIG. 28A), and thereafter, the scintillator 74 is sealed in a moisture-resistant protective layer 86. Next, the scintillator 74 is separated from the vapor deposition substrate 240, and the distal end portion of the columnar crystalline structure 84 and the photodetector substrate 72 are placed in close contact through a bonding layer 88a or an adhesive layer 88b, whereby the scintillator shown in FIG. 4B is constructed by elimination of the non-columnar crystalline portion 82. Further, upon forming the scintillator 74, after deposition conditions have been determined such that the non-columnar crystalline portion 82 is not formed, the scintillator 74 may be vapor deposited on the vapor deposition substrate 240 in accordance with such deposition conditions.

Further, in the aforementioned first example, in order to enhance close contact between the photodetector substrate 72 and the scintillator 74, the non-columnar crystalline portion 82 is positively formed, however, with the second example, to avoid generation of scattered light caused by the non-columnar crystalline portion 82, the scintillator 74 is formed without the non-columnar crystalline portion 82.

A method for manufacturing the electronic cassette 20B according to the second example shall be described in detail later.

In order to keep the distal end portion of the columnar crystalline structure 84 and the photodetector substrate 72 in increased close contact with each other, for thereby preventing the scintillator 74 and the photodetector substrate 72 from becoming spaced from each other while the electronic cassette 20B of the second example is in use, the distal end portion of the columnar crystalline structure 84 and the photodetector substrate 72 should firmly be bonded to each other by the bonding layer 88a. Further, if at least one of the scintillator 74 and the photodetector substrate 72 are configured to be replaceable in view of possible failures thereof, then the distal end portion of the columnar crystalline structure 84 and the photodetector substrate 72 may be adhered to each other separately by the adhesive layer 88b, which does not require as strong a bonding strength as the bonding layer 88a.

Figure 5A:
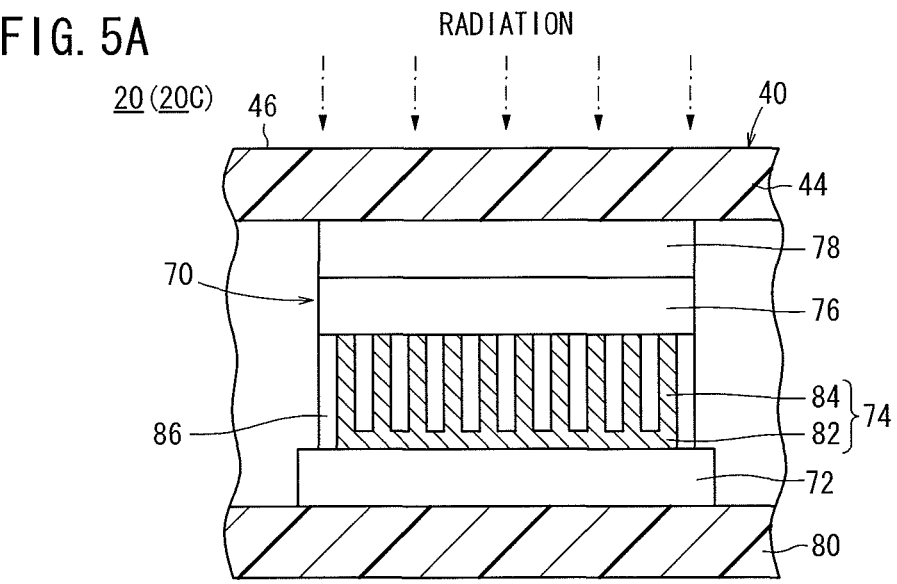
FIGS. 5A and 5B are enlarged fragmentary cross-sectional views of the electronic cassette (electronic cassettes according to a third example and a fourth example) shown in FIG. 3B in the vicinity of a radiation detector thereof.
Figure 5B:
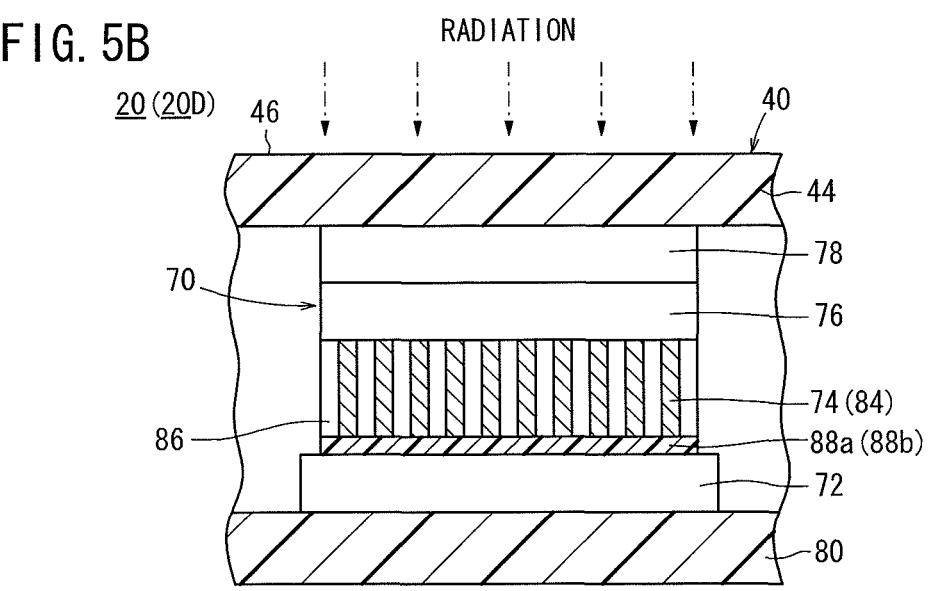

As shown in FIG. 5A, the electronic cassette 20C according to the third example differs from the electronic cassette 20A (see FIG. 4A) according to the first example, in that the radiation detector 70 is vertically reversed or turned upside down. As shown in FIG. 5B, the electronic cassette 20D according to the fourth example differs from the electronic cassette 20B (see FIG. 4B) according to the second example, in that the radiation detector 70 is vertically reversed or turned upside down.

In each of the electronic cassettes 20A through 20D according to the first through fourth examples, the photodetector substrate 72, the switching filter 76, and the resetting light source 78 may be secured in position within the casing 44 by any of various known securing means, such as bonding with a bonding agent, adhesion with an adhesive agent, or fixing with a fixing means.

In FIGS. 4A through 5B, the scintillator 74 is made of CsI:Tl. However, the scintillator 74 may be made of GOS (gadolinium oxide sulfur), for example, by coating the photodetector substrate 72 or the switching filter 76 with GOS.

Further, other than the scintillator 74 made of CsI:Tl or GOS, for example, the scintillator 74 may be made of BaFCl:Eu, BaFBr:Eu, YTaO$_4$, BaSO$_4$:Eu, or HfP$_2$O$_7$, which emits fluorescence (e.g., ultraviolet radiation) having an emission peak wavelength in a wavelength range from the violet (light) range to the ultraviolet range. In this case, the photodetector substrate 72 may convert fluorescence having such an emission peak wavelength emitted from the scintillator 74 into electric signals.

Next, specific structural details of the photodetector substrate 72, the switching filter 76, and the resetting light source 78 will be described below with reference to FIGS. 6A through 14.

As a representative example, specific structural details of the photodetector substrate 72, the switching filter 76, and the resetting light source 78 of the electronic cassette 20A according to the first example will be described below with reference to FIGS. 6A through 14. In FIGS. 6A through 14, certain components thereof are illustrated in a simplified or exaggerated form to facilitate easier understanding of the present invention. Specific structural details shown in FIGS. 6A through 14 may be modified and/or applied to the electronic cassettes 20B through 20D according to the second through fourth examples.

FIGS. 6A through 8 show different structures of the photodetector substrate 72. FIGS. 9 through 11B show a process of manufacturing the switching filter 76. FIGS. 12A through 14 show different structures of the resetting light source 78.

Figure 6A:
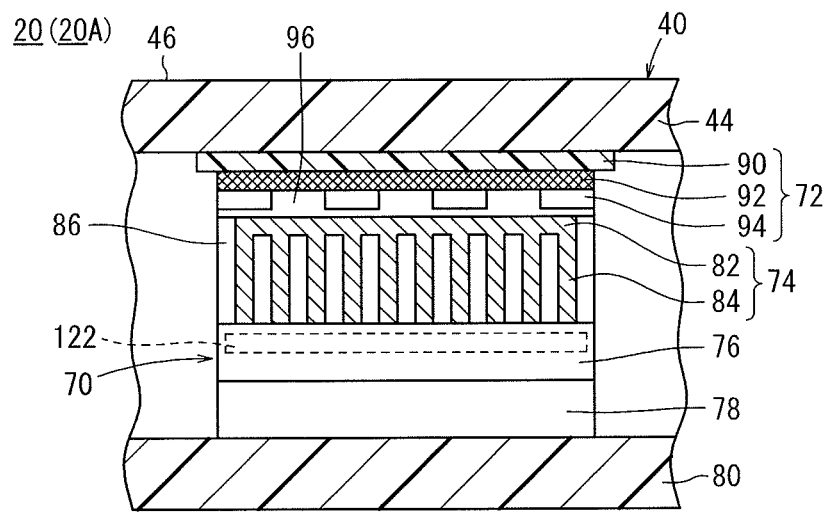
FIG. 6A is an enlarged fragmentary cross-sectional view of an electronic cassette in the vicinity of a radiation detector thereof.

In the structure shown in FIG. 6A, the photodetector substrate 72 includes a base 90, an array of TFTs (Thin Film Transistors) 92 disposed as switching elements on a surface of the base 90 that faces toward the bottom plate 80, and a plurality of photodetector devices 94 such as photodiodes made of a-Si or the like disposed on the array of TFTs 92. The photodetector devices 94, which contain a-Si, have a wide absorption spectrum and hence are capable of efficiently absorbing visible light 130 from the scintillator 74.

Since the photodetector devices 94, which are provided on the array of TFTs 92 disposed on the surface of the base 90 that faces the bottom plate 80, make surface irregularities on the photodetector substrate 72, it is desirable to perform a planarization process by covering the photodetector devices 94 with a planarization film 96 of polytetrafluoroethylene. The scintillator 74 of CsI:Tl is vapor deposited on the photodetector substrate 72 through the planarization film 96, and thereafter, the moisture-resistant protective layer 86 is applied thereto. Therefore, in the structure of FIG. 6A, the base 90, the TFTs 92, the photodetector devices 94, the planarization film 96, and the scintillator 74 are arranged or stacked successively along the direction in which radiation 16 is applied, i.e., in the downward direction shown in FIG. 6A.

The base 90 may be a thin base plate, which is resistant to heat that is applied upon vapor deposition of the scintillator 74. The base 90 is normally a glass substrate, but may be made of various other materials.

More specifically, so that the TFTs 92 and the photodetector devices 94 can be deposited as films at low temperatures, the photodetector devices 94 may be made of an organic photoconductor (OPC) for converting fluorescence in the visible range (visible light 130) emitted from the scintillator 74 into electric signals, or an amorphous oxide semiconductor, e.g., IGZO (InGaZnOx) or the like, for converting fluorescence having an emission peak wavelength in the wavelength range from the violet range to the ultraviolet range (e.g., ultraviolet radiation) emitted from the scintillator 74 into electric signals. The TFTs 92 may be made of an organic semiconductor (e.g., phthalocyanine compound, pentacene, or vanadyl phthalocyanine), an amorphous oxide semiconductor, e.g., a-IGZO (InGaZnO$_4$), or carbon nanotubes. With such materials, a plastic film, which is flexible and permeable at least to the resetting light 132, such as a polyimide film, a polyarylate film, a biaxially-oriented polystyrene film, an aramid film, or a film of bionanofibers, may be used as the base 90.

The plastic film, which may be used as the base 90, will be described in greater detail below. The plastic film, which may be used as the base 90, should preferably be a flexible substrate of a polyester such as polyethylene terephthalate, polybutylene phthalate, polyethylene naphthalate, or the like, or polystyrene, polycarbonate, polyethersulfone, polyarylate, polyimide, polycycloolefin, norbornene resin, poly(chlorotrifluoroethylene), or the like. A flexible substrate of plastic makes the electronic cassette 20 (20A) light in weight and hence easy to carry.

The base 90 may include an insulating layer for making the base 90 electrically insulative, a gas barrier layer for making the base 90 impermeable to water and oxygen, and an undercoat layer for making the base 90 flat or in better intimate contact with electrodes.

An aramid film for use as the base 90 is advantageous in that, since a high-temperature process at 200 degrees Celsius may be applied thereto, the aramid film allows a transparent electrode material to be set at a high temperature in order to exhibit lower resistance, and also allows driver ICs to be automatically mounted thereon by a process including a solder reflow process. Furthermore, inasmuch as an aramid film has a coefficient of thermal expansion close to that of ITO (Indium Tin Oxide) and glass, a base made of an aramid film is less likely to become warped or cracked after fabrication. In addition, a base made of an aramid film may be made thinner than a glass substrate or the like. The base 90 may also be in the form of a stacked assembly comprising an ultrathin glass substrate and an aramid film.

Bionanofibers are made by compounding a bundle of cellulose microfibrils (bacteria cellulose) produced by bacteria (acetic acid bacteria, Acetobacter Xylinum) and a transparent resin. The bundle of cellulose microfibrils has a width of 50 nm, which is 1/10 the wavelength of visible light 130, is highly strong and highly resilient, and is subject to low thermal expansion. Bionanofibers, which contain 60% to 70% of fibers and exhibit a light transmittance of about 90% at a wavelength of 500 nm, can be produced by impregnating bacteria cellulose with a transparent resin such as an acrylic resin, an epoxy resin, or the like, and setting the transparent resin. Bionanofibers are flexible and have a low coefficient of thermal expansion ranging from 3 ppm to 7 ppm, which is comparable to silicon crystals, a high strength of 460 MPa that matches the strength of steel, and a high resiliency of 30 GPa. Therefore, if the base 90 is made of bionanofibers, the base 90 can be thinner than glass substrates or the like.

The photodetector devices 94, which include an organic photoconductor, exhibit a sharp absorption spectrum in the range of visible light 130 and do not absorb electromagnetic waves other than visible light 130, such that any noise that would be produced if radiation 16 were absorbed by the photodetector devices 94 is effectively minimized.

In order for the organic photoconductor to absorb visible light 130 most efficiently, the absorption peak wavelength thereof should preferably be as close as possible to the light emission peak wavelength of the scintillator 74. Although the absorption peak wavelength of the organic photoconductor and the light emission peak wavelength of the scintillator 74 should ideally be in agreement with each other, it is possible to sufficiently absorb visible light 130 if the difference in wavelength between the absorption peak wavelength and the light emission peak wavelength is small enough. More specifically, the difference between the absorption peak wavelength of the organic photoconductor and the light emission peak wavelength should preferably be 10 nm or smaller, and more preferably, 5 nm or smaller.

Organic photoconductors that meet the above requirements include quinacridone-based organic compounds and phthalocyanine-based organic compounds. Since quinacridone has an absorption peak wavelength of 560 nm in the visible range, if quinacridone is used as the organic photoconductor and CsI:Tl is used as the material of the scintillator 74, then the difference between the aforementioned peak wavelengths can be reduced to 5 nm or smaller, thereby making it possible to substantially maximize the amount of electric charge generated by the photodetector devices 94.

Further, if the TFTs 92 are made of an organic semiconductor, an amorphous oxide semiconductor, or carbon nanotubes, then the TFTs 92 can effectively prevent noise from being produced, because the TFTs 92 do not absorb radiation 16 or absorb only a small dose of radiation 16. In particular, if the TFTs 92 are made of carbon nanotubes, then the TFTs 92 can have a high switching speed and exhibit a low absorption rate both for visible light 130 and resetting light 132. If the TFTs 92 are made of carbon nanotubes, then since the performance of the TFTs 92 could be degraded significantly by trace metal impurities mixed therein, it is necessary to separate and extract highly pure carbon nanotubes by a centrifugal separator or the like.

With the electronic cassette shown in FIG. 6A, radiation 16 that has passed through the subject 14 is transmitted to the scintillator 74 through the irradiation surface 46 (top plate) of the casing 44 and the photodetector substrate 72. Such radiation 16 is then converted by the columnar crystalline structure 84 of the scintillator 74 into fluorescence in the visible range (visible light 130), which travels through the columns of the columnar crystalline structure 84, and then is transmitted to the photodetector devices 94 via the non-columnar crystalline portion 82 and the planarization film 96 (see FIGS. 11A and 11B).

Part of the visible light 130 that travels toward the switching filter 76 is reflected toward the photodetector substrate 72 by a later-described light-regulating mirror film layer 122 of the switching filter 76. Owing thereto, this portion of the visible light 130 (i.e., reflected light) reaches the photodetector devices 94 via the scintillator 74 and the planarization film 96.

Therefore, the photodetector devices 94 convert visible light 130 into analog electric signals and store the electric signals as electric charges. The TFTs 92 read the electric charges stored in the photodetector devices 94 as an image signal.

Figure 6B:
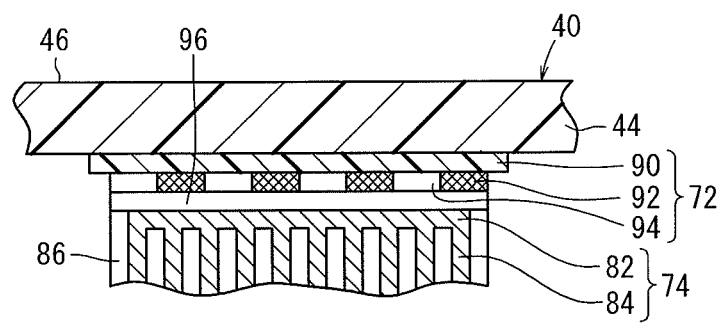
FIG. 6B is an enlarged fragmentary cross-sectional view of an electronic cassette in the vicinity of a photodetector substrate.

The structure shown in FIG. 6B differs from the structure shown in FIG. 6A, in that the TFTs 92 and the photodetector devices 94 are alternately positioned. A TFT 92 and a photodetector device 94, which are disposed adjacent to each other, make up an area corresponding to one pixel. With the structure of FIG. 6B, since the TFTs 92 and the photodetector devices 94 of the photodetector substrate 72 have surface irregularities, it is preferable for the TFTs 92 and the photodetector devices 94 to be covered with a planarization film 96, in order to keep the scintillator 74 that is vapor deposited on the photodetector substrate 72 in close contact with respect to the photodetector substrate 72.

Figure 7A:
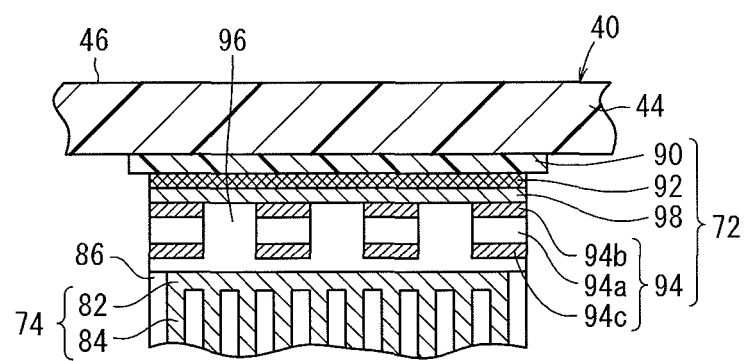
FIGS. 7A and 7B are enlarged fragmentary cross-sectional views of electronic cassettes in the vicinity of a photodetector substrate.

The structure shown in FIG. 7A differs from the structures shown in FIGS. 6A and 6B, in that an array of TFTs 92 made of a-Si, a reflective layer 98 made of a metal such as aluminum or the like, and a plurality of photodetector devices 94 are stacked in this order on a surface of the base 90 that faces toward the scintillator 74, and the planarization film 96 is formed on the side of the photodetector substrate 72 that includes the photodetector devices 94.

In this case, the respective photodetector devices 94 are constituted by sandwiching photodetectors 94a respectively between two electrodes 94b, 94c provided on upper and lower sides thereof.

In addition, with the structure of FIG. 7A, by providing the reflective layer 98 on the array of TFTs 92, in the case that visible light 130 from the scintillator 74 or resetting light 132 from the resetting light source 78 is incident on the photodetector substrate 72, all of such light is reflected by the reflective layer 98 toward the side of the photodetector devices 94. Consequently, generation of switching noise by the TFTs 92 due to incidence thereon of the visible light 130 or the resetting light 132 can be avoided. Further, by the reflective layer 98 reflecting the visible light 130 and the resetting light 132, because such reflected light is made incident on the photodetectors 94a of the photodetector devices 94, the intensity of the visible light 130 or the resetting light 132 incident on the photodetectors 94a is increased. As a result, sensitivity of the photodetectors 94a with respect to visible light 130 can be enhanced, and resetting of the photodetector devices 94 by the resetting light 132 can be performed more efficiently.

In FIG. 7A, a case is shown in which the reflective layer 98 is stacked on the array of TFTs 92, however, instead of this structure, the reflective layer 98 may be formed between the respective photodetector devices 94 and the array of TFTs 92, such that the photodetector devices 94 overlap therewith. In this case, because the reflective layer 98 is formed with substantially the same area as the photodetector devices 94, such that one photodetector device 94 corresponds to a pixel unit making up one pixel, generation of crosstalk between respective pixels caused by reflection of visible light 130 or resetting light 132 by the reflective layer 98 can be avoided.

Figure 7B:
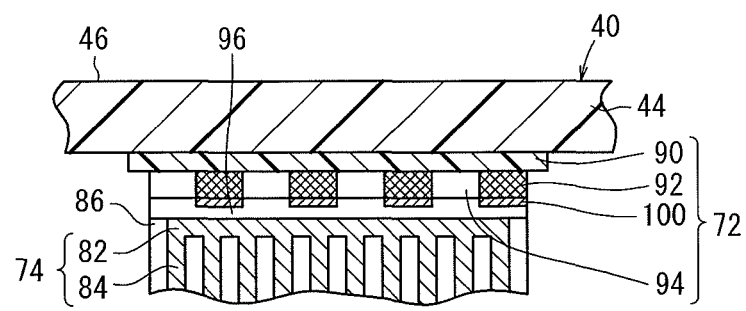

The structure of FIG. 7B differs from the structure of FIGS. 6A through 7A, in that the TFTs 92 made from a-Si and the photodetector devices 94, which employ photodiodes made from a-Si, are formed alternately on the surface of the base 90 facing the scintillator 74, a light shield layer 100 is formed on the bottom plate 80 side of the respective TFTs 92, and a planarization film 96 is formed on the side of the light shield layer 100 and the photodetector devices 94 of the photodetector substrate 72.

In this case, by forming the light shield layer 100 on the TFTs 92, even if visible light 130 from the scintillator 74 and resetting light 132 from the resetting light source 78 are applied to the photodetector substrate 72, light traveling toward the photodetector devices 94 is applied to the photodetector devices 94, and light traveling toward the TFTs 92 is fully absorbed by the light shield layer 100. Consequently, with the structure of FIG. 7B, visible light 130 or resetting light 132 can efficiently be applied to the photodetector devices 94, and switching noise, which otherwise would be generated by the TFTs 92 if the TFTs 92 were exposed to visible light 130 or resetting light 132, can reliably be prevented.

Figure 8:
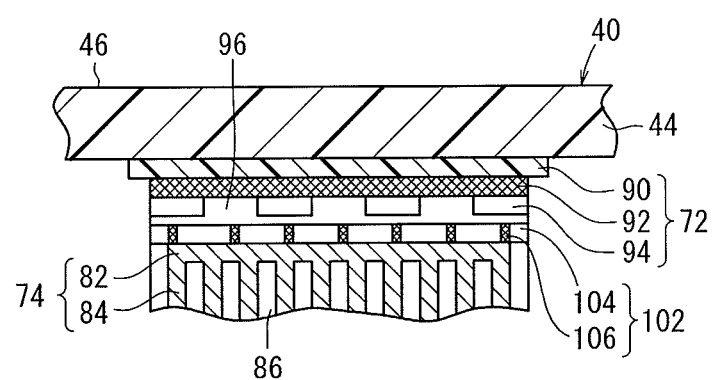
FIG. 8 is an enlarged fragmentary cross-sectional view of an electronic cassette in the vicinity of a photodetector substrate.

The structure shown in FIG. 8 differs from the structures shown in FIGS. 6A through 7B, in that an oblique light blocking layer 102, for blocking visible light 130 or resetting light 132 that travels obliquely to the direction in which radiation 16 is applied, is interposed between the planarization film 96 and the scintillator 74. The oblique light blocking layer 102 includes light transmitters 104 made of a material permeable to visible light 130 or resetting light 132 (e.g., silicone resin, olefin resin, urethane resin, acrylic resin, cellulose resin, polyester resin, or polycarbonate resin) and light blockers 106 made of a material having a high absorption rate for visible light 130 or resetting light 132 (e.g., a dark metal oxide, a pigment, or a dye). The light transmitters 104 and the light blockers 106 are alternately arrayed along the surface, i.e., in a horizontal direction, of the planarization film 96.

In this case, visible light 130 or resetting light 132, which is applied within a predetermined angle with respect to the direction in which radiation 16 is applied, passes through the light transmitters 104 and is applied to the photodetector substrate 72. On the other hand, visible light 130 or resetting light 132 that is applied obliquely at an angle beyond the predetermined angle is fully absorbed by the light blockers 106 and is prevented from being applied to the photodetector substrate 72. As a result, the photodetector devices 94 are rendered more sensitive with respect to visible light 130, resetting of the photodetector devices 94 by resetting light 132 can be performed more efficiently, and the generated radiographic images can be prevented from becoming blurred due to obliquely applied light.

The structures shown in FIGS. 6A through 8 are simply examples, and the structures thereof may be combined appropriately to make up the photodetector substrate 72. For example, in each of the structures shown in FIGS. 6B through 7B, the oblique light blocking layer 102 may be interposed between the surface of the planarization film 96 and the scintillator 74.

Figure 9:
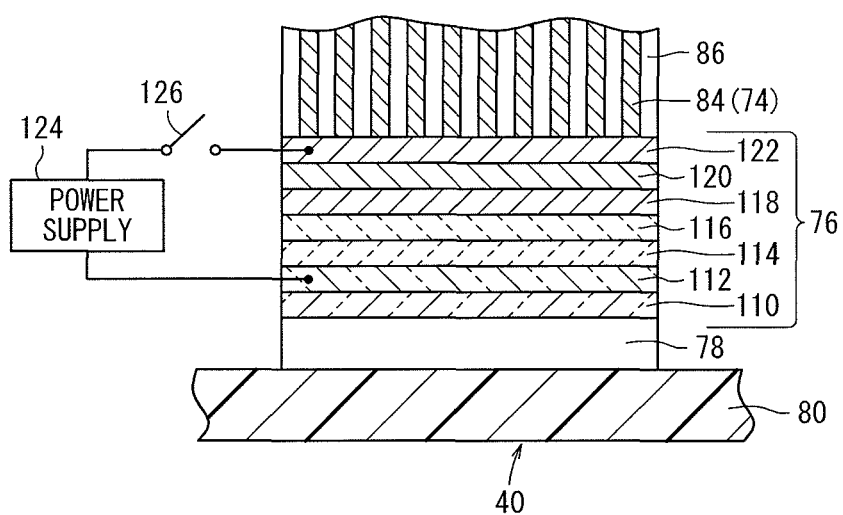
FIG. 9 is a cross-sectional view of a switching filter.

As shown in FIG. 9, the switching filter 76 is constructed by stacking a transparent base 110, a transparent conductive film 112, an ion storage layer 114, a solid-state electrolytic layer 116, a buffer layer 118, a catalyst layer 120, and a light-regulating mirror film layer 122 in this order along a direction from the resetting light source 78 toward the photodetector substrate 72. In this case, a power supply 124 and a switch 126 are electrically connected to the transparent conductive film 112 and the light-regulating mirror film layer 122.

The transparent base 110 serves as an evaporated substrate of the switching filter 76, which is located near the resetting light source 78. The transparent base 110 may be a glass substrate or a plastic substrate, which is permeable to resetting light 132 (see FIGS. 10A and 10B) emitted from the resetting light source 78. The transparent conductive film 112 is a transparent electrode made of ITO, which is permeable to the resetting light 132. The ion storage layer 114 is a thin film made of $WO_3$ (tungsten oxide), which is capable of storing hydrogen ions ($H^+$). The solid-state electrolytic layer 116 is a thin film made of $Ta_2O_5$ (tantalum oxide). The buffer layer 118 is a metal film made of Al (aluminum). The catalyst layer 120 is a thin film made of Pd (palladium). The light-regulating mirror film layer 122 comprises a thin film fabricated from a Mg.Ni (magnesium•nickel) alloy.

In this case, if the switch 126 is turned on, the power supply 124 applies a voltage between the transparent conductive film 112 and the light-regulating mirror film layer 122, whereby the light-regulating mirror film layer 122 changes to a mirror state (non-transmissive state) or a transparent state (transmissive state). The mirror state (non-transmissive state) is a state in which the light-regulating mirror film layer 122 reflects resetting light 132 toward the resetting light source 78, and also reflects visible light 130 (see FIGS. 11A and 11B) emitted by the scintillator 74 toward the photodetector substrate 72. The transparent state (transmissive state) is a state in which the light-regulating mirror film layer 122 passes resetting light 132 through the scintillator 74 to the photodetector devices 94 of the photodetector substrate 72.

Switching of the light-regulating mirror film layer 122 between the mirror state and the transparent state will be described in specific detail below.

The light-regulating mirror film layer 122 has a surface, which is normally in a mirror state and is capable of reflecting visible light 130 and resetting light 132 due to the metallic luster of the Mg.Ni alloy thin film.

Figure 10A:
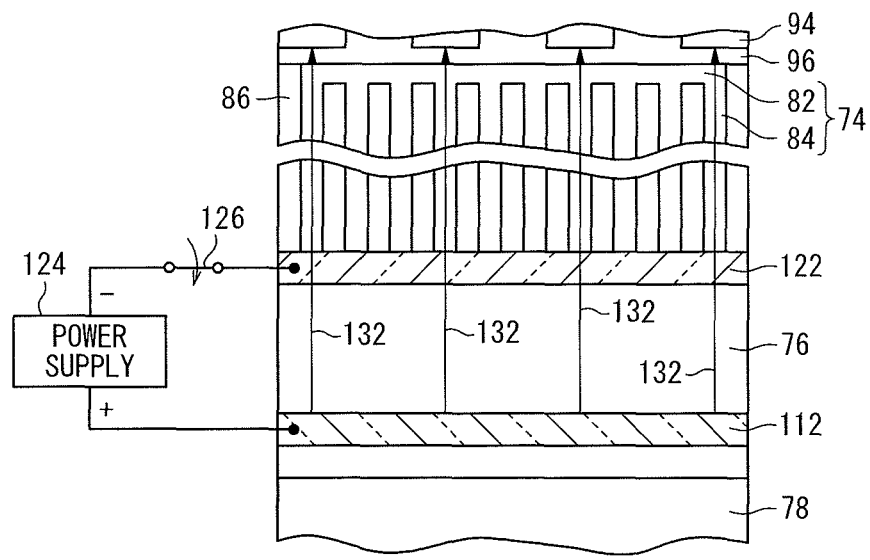
FIGS. 10A and 10B are cross-sectional views showing the manner in which the switching filter is brought into a transparent state.

If the light-regulating mirror film layer 122 is in a mirror state, the switch 126 is turned on to apply a voltage, i.e., a DC voltage of a few volts, from the power supply 124 to the switching filter 76, such that the light-regulating mirror film layer 122 is set at a negative polarity and the transparent conductive film 112 is set at a positive polarity, as shown in FIG. 10A. At this time, the light-regulating mirror film layer 122 switches from the mirror state to the transparent state. More specifically, hydrogen ions ($H^+$) stored in the ion storage layer 114 move through the solid-state electrolytic layer 116, the buffer layer 118, and the catalyst layer 120 to the light-regulating mirror film layer 122, whereupon the Mg.Ni alloy is hydrogenated from its metal state into a non-metal state and becomes transparent.

Figure 10B:
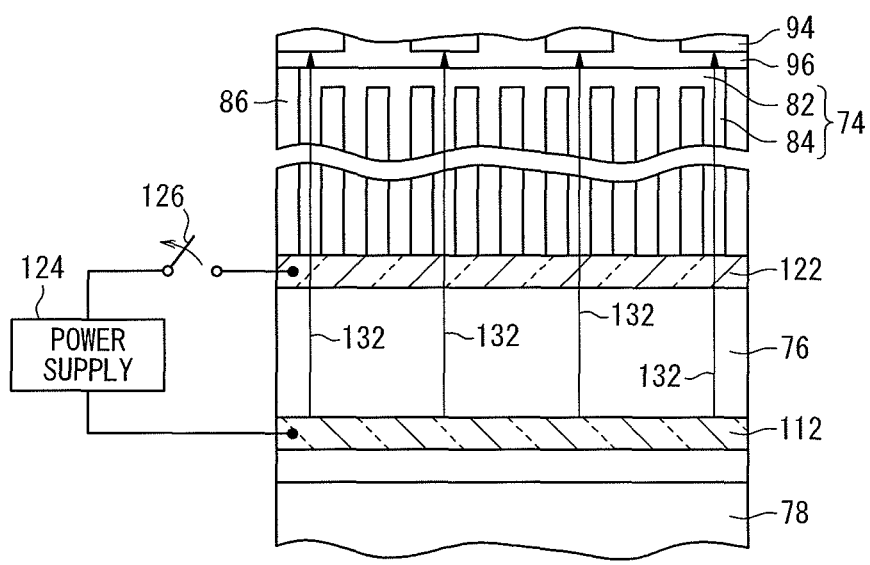

Once the light-regulating mirror film layer 122 has become transparent, the light-regulating mirror film layer 122 remains transparent even if the switch 126 is turned off and application of voltage from the power supply 124 to the switching filter 76 is stopped, i.e., energization of the switching filter 76 is turned off, as shown in FIG. 10B.

While the light-regulating mirror film layer 122 is in the transparent state and radiation 16 is not applied to the subject 14, i.e., a radiographic image of the subject 14 is not being captured, if the resetting light source 78 emits resetting light 132 toward the switching filter 76, the resetting light 132 passes through the transparent conductive film 112 and the light-regulating mirror film layer 122 and is made incident on the scintillator 74, and furthermore, is made incident on the photodetector devices 94 from the scintillator 74 via the planarization film 96. If resetting light 132 is applied to the photodetector devices 94, each in the form of a photodiode of a-Si or the like, the photodetector devices 94 are reset to embed electric charges at the impurity level of the photodiode, so that electric charges converted from visible light 130 by the photodetector devices 94 during application of radiation 16 thereto, i.e., when a radiographic image of the subject 14 is being captured, will not become trapped by the impurity level.

On the other hand, if the light-regulating mirror film layer 122 is in the transparent state, the switch 126 is turned on to apply a voltage, i.e., a DC voltage of a few volts, which is opposite in polarity to the voltage polarity shown in FIG. 10A, to the switching filter 76, such that the light-regulating mirror film layer 122 is set at a positive polarity and the transparent conductive film 112 is set at a negative polarity, as shown in FIG. 11A. At this time, the light-regulating mirror film layer 122 switches from the transparent state to the mirror state. More specifically, hydrogen ions, which have moved to the light-regulating mirror film layer 122, flow back through the catalyst layer 120, the buffer layer 118, and the solid-state electrolytic layer 116 to the ion storage layer 114, under the influence of the applied voltage that is opposite in polarity, whereupon the light-regulating mirror film layer 122 changes back to its original metal state.

With the light-regulating mirror film layer 122 returned to the mirror state, the light-regulating mirror film layer 122 remains in the mirror state even if the switch 126 is turned off and application of voltage from the power supply 124 to the switching filter 76 is stopped, as shown in FIG. 11B.

While the light-regulating mirror film layer 122 is in a mirror state and radiation 16 is applied to the subject 14, i.e., if a radiographic image of the subject 14 is captured, among the visible light 130 that is converted from radiation 16 by the scintillator 74, light that travels toward the light-regulating mirror film layer 122 is reflected toward the photodetector substrate 72 by the light-regulating mirror film layer 122. The photodetector devices 94 then detect, as electric signals, fluorescence, i.e., visible light 130, converted by the scintillator 74 and applied directly through the planarization film 96, and also detect reflected light (i.e., visible light 130) that is reflected by the light-regulating mirror film layer 122 and is applied through the scintillator 74 and the planarization film 96. As a result, the sensitivity of the photodetector devices 94 with respect to visible light 130 easily is increased.

When a radiographic image of the subject 14 is captured, i.e., when radiation 16 is applied to the subject 14, the resetting light source 78 may be irradiated with radiation 16 and caused to emit resetting light 132, or may be energized in error and thereby emit resetting light 132.

Notwithstanding, during image capturing, because in the scintillator 74 a large portion of the radiation 16 is converted into visible light 130, the radiation 16 that passes through the scintillator 74 and reaches the switching filter 76 is extremely small. Further during image capturing, because the light-regulating mirror film layer 122 is in a mirror state (metal state), radiation 16 that reaches the switching filter 76 is absorbed by the light-regulating mirror film layer 122, which is in a metal state, and hence such radiation 16 is prevented from reaching the resetting light source 78. Even if radiation 16 does reach the resetting light source 78, thereby causing the resetting light source 78 to emit resetting light 132, the resetting light 132 can be reflected toward the resetting light source 78 by the light-regulating mirror film layer 122, which is in a mirror state. Therefore, resetting light 132 is prevented from traveling toward the scintillator 74 and the photodetector substrate 72.

With electronic cassettes 20A and 20B of an ISS type, since the photodetector substrate 72, the scintillator 74, the switching filter 76, and the resetting light source 78 are successively arranged in this order in the casing 44 along the direction in which radiation 16 is applied, the above operations and advantages are achieved without reducing the amount of radiation 16 that reaches the scintillator 74.

As described above, with ISS type electronic cassettes 20A and 20B, since most of the radiation 16 is converted into visible light 130 by the scintillator 74, only minimal radiation 16 passes through the scintillator 74 and reaches the switching filter 76. Accordingly, it is possible to keep the switching filter 76 in a transparent state while radiation 16 is applied. In this case as well, the aforementioned problems do not arise, or even if they occur, it can be expected that a significant adverse influence will not be imparted thereby to the radiographic images.

FIGS. 12A through 14 show different resetting light sources 78. Each of the resetting light sources 78 includes an array of light-emitting elements 142, and a backlight (see FIGS. 12B through 13B), or an electroluminescent light source (see FIG. 14), disposed in facing relation to the photodetector substrate 72, with the switching filter 76 and the scintillator 74 interposed therebetween.

Figure 12A:
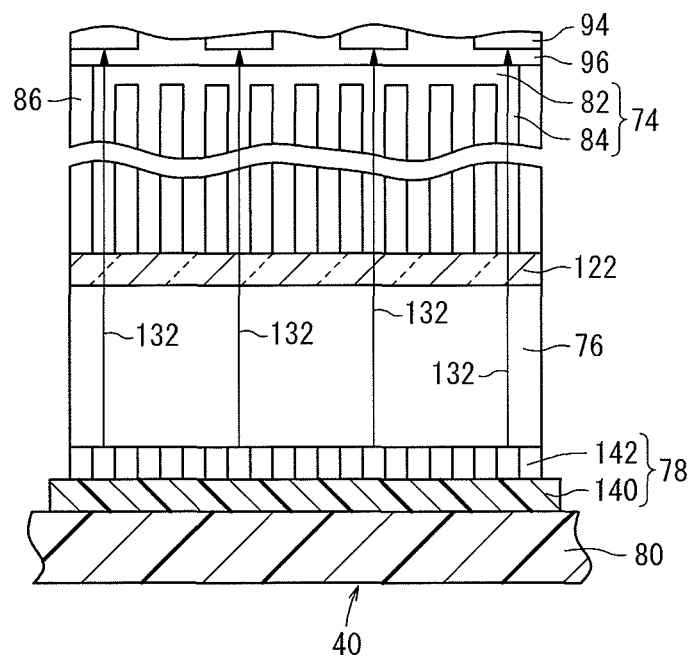
FIGS. 12A and 12B are cross-sectional views, each showing a switching filter and a resetting light source.

The resetting light source 78 shown in FIG. 12A includes the array of light-emitting elements 142 in the form of light-emitting diodes (LEDs) or the like, which are disposed on a base 140 disposed on the bottom plate 80 of the casing 44. While the light-regulating mirror film layer 122 is in the transparent state, if the light-emitting elements 142 simultaneously emit resetting light 132, the resetting light source 78 functions as a surface emission light source. Resetting light 132 is uniformly applied through the switching filter 76, the scintillator 74, and the planarization film 96 to the photodetector devices 94 in order to reset the photodetector devices 94.

The resetting light source 78 shown in FIG. 12A also is capable of pinpointing each of the photodetector devices 94 to reset a certain device by energizing only the light-emitting element 142 that faces toward the pinpointed photodetector device 94.

Figure 12B:
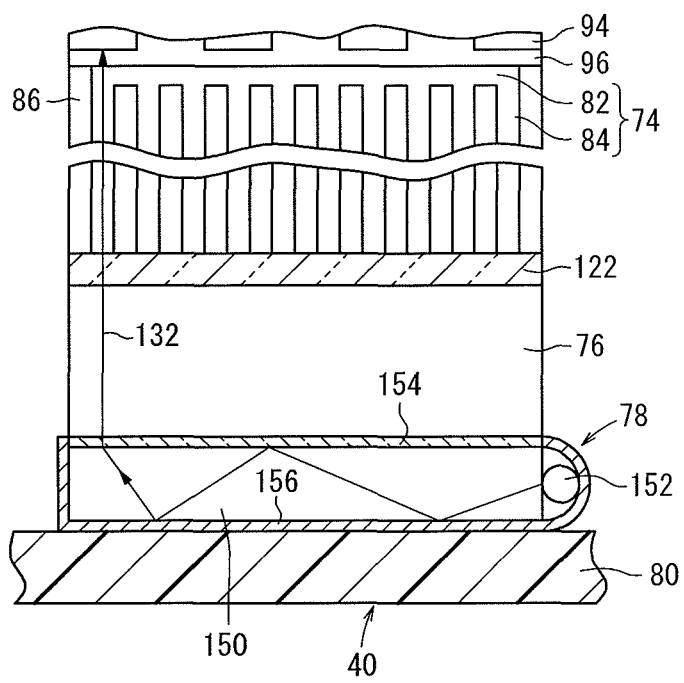

The resetting light source 78 shown in FIG. 12B is an edge-lit backlight, including a light guide plate 150 disposed between the bottom plate 80 of the casing 44 and the switching filter 76, and a cold-cathode ray tube (light source) 152 disposed on a side of the light guide plate 150. The region in which the cold-cathode ray tube 152 is disposed is not irradiated with radiation 16. A diffusion sheet 154 is interposed between the light guide plate 150 and the switching filter 76, and a reflective sheet 156 is disposed in surrounding relation to the light guide plate 150 and the cold-cathode ray tube 152. If light is applied from the cold-cathode ray tube 152 toward the light guide plate 150, the applied light is repeatedly reflected within the light guide plate 150 by surfaces of the reflective sheet 156 and the diffusion sheet 154, and then the light is emitted as resetting light 132 through the diffusion sheet 154 toward the switching filter 76.

In FIG. 12B, only one ray of resetting light 132 is illustrated. Actually, however, light applied from the cold-cathode ray tube 152 toward the light guide plate 150 is repeatedly reflected by the surfaces, and spreads fully within the light guide plate 150, so that such light is emitted as surface-emission resetting light 132 from the diffusion sheet 154 toward the switching filter 76. Therefore, the resetting light source 78 in the form of a backlight also functions as a surface-emission light source for uniformly applying resetting light 132 through the switching filter 76, the scintillator 74, and the planarization film 96 to the photodetector devices 94 to thereby reset the photodetector devices 94.

Figure 13A:
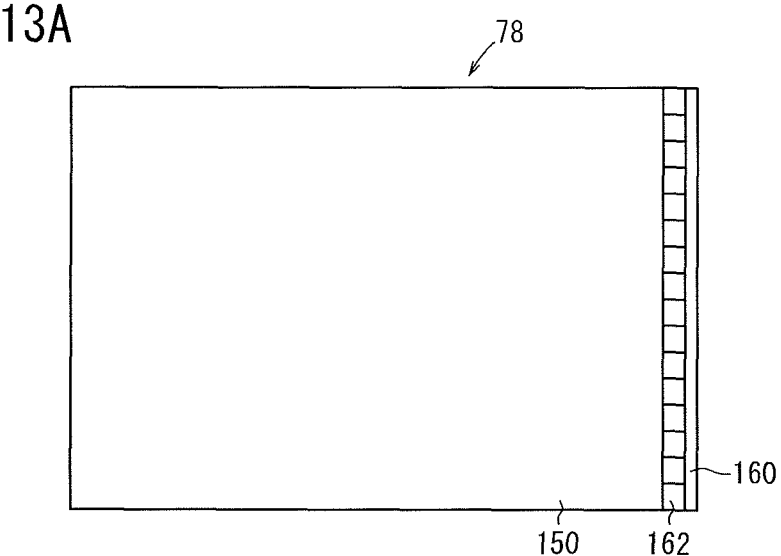
FIG. 13A is a fragmentary plan view of a resetting light source.
Figure 13B:
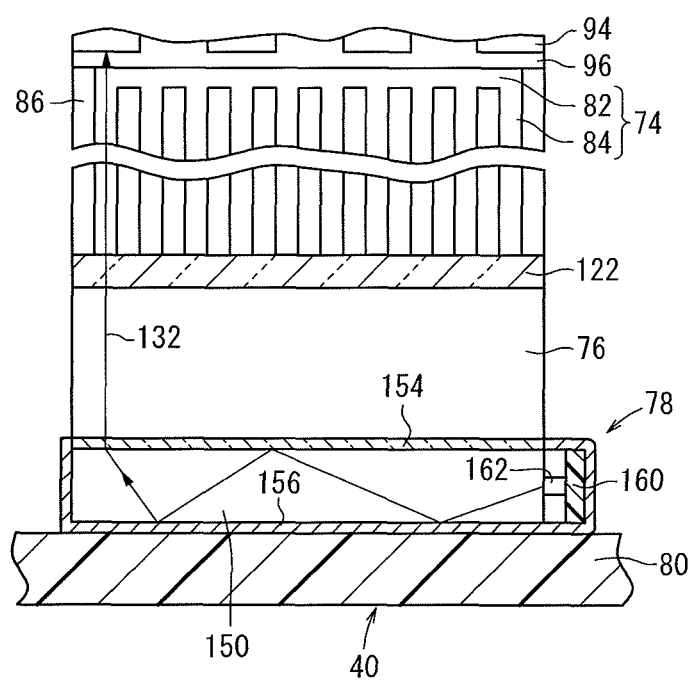
FIG. 13B is a cross-sectional view showing a switching filter and a resetting light source.

The resetting light source 78 shown in FIGS. 13A and 13B, which also is an edge-lit backlight, differs from the resetting light source 78 shown in FIG. 12B, in that the resetting light source 78 includes a substrate 160 supporting thereon a linear array of light-emitting elements (light sources) 162 such as LEDs or the like, instead of the cold-cathode ray tube 152. The region in which the light-emitting elements 162 and the substrate 160 are disposed is not irradiated with radiation 16. If light is applied from the light-emitting elements 162 toward the light guide plate 150, the applied light is repeatedly reflected by surfaces of the reflective sheet 156 and the diffusion sheet 154, and spreads fully within the light guide plate 150, so that such light is emitted as surface-emission resetting light 132 from the diffusion sheet 154 toward the switching filter 76. Therefore, the resetting light source 78 is capable of uniformly applying resetting light 132 through the switching filter 76, the scintillator 74, and the planarization film 96, to the respective photodetector devices 94 to thereby reset the photodetector devices 94. In FIG. 13B, only one ray of the resetting light 132 is illustrated.

The resetting light source 78 shown in FIG. 14 is an organic electroluminescence (EL) light source or an inorganic electroluminescence (EL) light source. The resetting light source 78 includes a light-emitting layer 170 made of an organic EL material or an inorganic EL material, a transparent electrode 172 made of ITO, which is permeable to resetting light 132, and a metal electrode 174, which is impermeable to resetting light 132. The transparent electrode 172 and the metal electrode 174 are electrically connected to a switch 176 and a power supply 178. If the light-regulating mirror film layer 122 is in the transparent state, the switch 176 is turned on to apply a voltage from the power supply 178 between the transparent electrode 172 and the metal electrode 174, such that the transparent electrode 172 is set at a positive polarity and the metal electrode 174 is set at a negative polarity. At this time, the light-emitting layer 170 emits surface-emission resetting light 132 through the transparent electrode 172 to the switching filter 76.

Therefore, the resetting light source 78, whether it is made of an organic EL light source or an inorganic EL light source, is capable of uniformly applying resetting light 132 through the switching filter 76, the scintillator 74, and the planarization film 96 to the photodetector devices 94, to thereby reset the photodetector devices 94.

As the above-mentioned resetting light 132 emitted from the resetting light source 78, for example, it is preferable to use dark red light or infrared radiation having energy of 0.8 eV to 2.0 eV (corresponding to wavelengths from 620 nm to 1550 nm) for resetting the photodetector devices 94.

Figure 15:
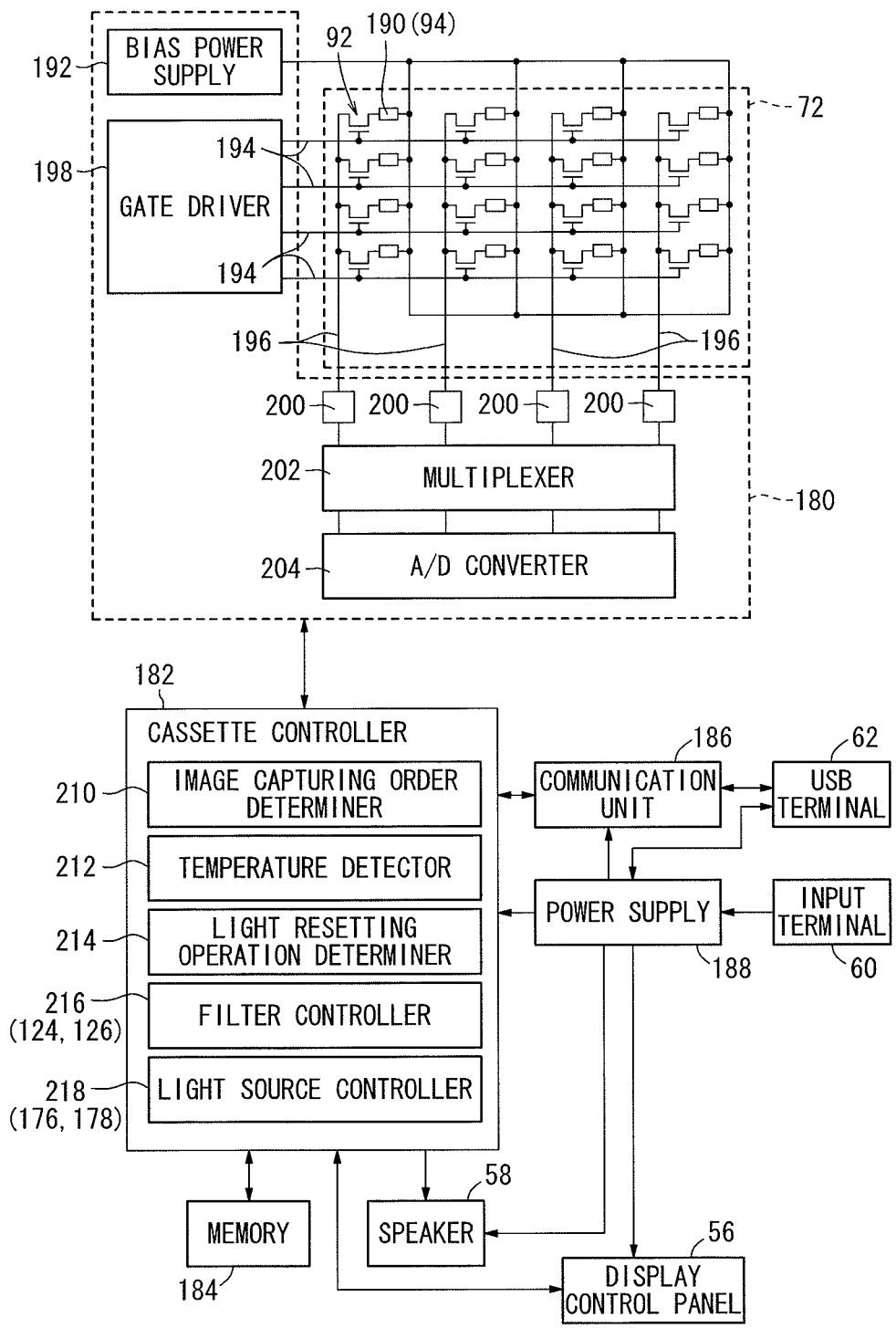
FIG. 15 is a schematic view, partially in block form, of an electric arrangement of the electronic cassette shown in FIG. 1.

FIG. 15 is a schematic view, partially in block form, of an electric arrangement of the electronic cassette 20 (20A through 20D) shown in FIG. 1.

As shown in FIG. 15, the photodetector substrate 72 of the electronic cassette 20 (20A through 20D) has a structure including an array or matrix of photodetector devices 94 and TFTs 92 on the base 90 (see FIGS. 6A through 8). The photodetector devices 94 will also be referred to as pixels 190.

The pixels 190, which are arranged in a matrix of rows and columns, are energized upon application of a bias voltage thereto from a bias power supply 192 of a drive circuit 180. The pixels 190 store electric charges that are generated in a case where visible light 130 converted from radiation 16 by the scintillator 74 is photoelectrically converted. The electric charges stored in the pixels 190 are read as pixel values of analog signals (electric charge signals, electric signals) via signal lines 196 if the TFTs 92 are successively turned on column by column. In FIG. 15, the pixels 190 and the TFTs 92 are arranged in a matrix of four vertical columns and four horizontal rows. However, the pixels 190 and the TFTs 92 may be arranged in a matrix of any desired number of vertical columns and any desired number of horizontal rows.

The TFTs 92, which are electrically connected to the respective pixels 190, are connected to gate lines 194 extending along the respective rows and signal lines 196 extending along the respective columns. The gate lines 194 are connected to a gate driver 198 of the drive circuit 180, and the signal lines 196 are connected to a multiplexer 202 of the drive circuit 180 through respective charge amplifiers 200. The multiplexer 202 is connected to an A/D converter 204, which converts analog electric signals into digital electric signals. The A/D converter 204 outputs digital electric signals, i.e., digital signal pixel values (hereinafter also referred to as digital values) to a cassette controller 182. The drive circuit 180 is included in the panel 40 or in the controller 42 (see FIG. 2). The cassette controller 182 is included in the controller 42.

The cassette controller 182 controls the electronic cassette 20 (20A through 20D) in its entirety. An information processing apparatus such as a computer or the like may function as the cassette controller 182 if the information processing apparatus reads and executes a program, which corresponds functionally to the cassette controller 182.

A memory 184 and a communication unit 186 are connected to the cassette controller 182. The memory 184 stores the digital signal pixel values, and the communication unit 186 sends signals to and receives signals from the console 22. The communication unit 186 sends packets of a single image, i.e., a one-frame image, made up of a matrix of pixel values to the console 22. A power supply 188 supplies electric power to the cassette controller 182, the memory 184, and the communication unit 186, etc., and also supplies electric power to the bias power supply 192. The memory 184, the communication unit 186, and the power supply 188 are included in the controller 42.

The cassette controller 182 includes an image capturing order determiner 210, a temperature detector 212, a light resetting operation determiner 214, a filter controller 216, and a light source controller 218.

If the image capturing order determiner 210 receives order information representing an image capturing order with respect to application of radiation 16 to the subject 14, i.e., for capturing radiographic images of the subject 14, the image capturing order determiner 210 identifies, i.e., determines, an image capturing method included within the order information. The order information is produced by the doctor in the RIS 26 or the HIS 28, and includes subject information for identifying the subject 14, such as the name, age, gender, etc., of the subject 14, information concerning the radiation output device 18 and the electronic cassette 20 that are used to capture a radiographic image of the subject 14, a region to be imaged of the subject 14, a technique used to capture a radiographic image of the subject 14, and an image capturing method indicative of capturing of a still image or capturing of a moving image.

Further, if resetting light 132 emitted from the resetting light source 78 is applied to the photodetector devices 94, i.e., the pixels 190, to thereby reset the photodetector devices 94, the photodetector devices 94 detect electric signals, i.e., dark current signals, depending on the resetting light 132, and store the detected dark current signals as electric charges. The level of the dark current signals varies depending on the temperature of the photodiodes that serve as the photodetector devices 94. The temperature detector 212 detects the temperature of the photodetector devices 94 based on the dark current signals, i.e., pixel values thereof, which are read via the signal lines 196 from the photodetector devices 94 if the TFTs 92 are successively turned on.

The light resetting operation determiner 214 determines whether or not a light resetting process is to be performed on the photodetector devices 94, i.e., whether the photodetector devices 94 are to be reset by the resetting light 132, based on the image capturing method identified by the image capturing order determiner 210 and the temperature of the photodetector devices 94 detected by the temperature detector 212.

The filter controller 216 performs functions of the power supply 124 and the switch 126 (see FIGS. 9 through 11B), so as to apply a voltage to the switching filter 76 and control switching of the light-regulating mirror film layer 122 between the mirror state and the transparent state. The light source controller 218 performs functions of the switch 176 and the power supply 178 (see FIG. 14), so as to control emission of resetting light 132 from the resetting light source 78.

The image capturing method identified by the image capturing order determiner 210, the temperature detected by the temperature detector 212, the light resetting process determined by the light resetting operation determiner 214, switching of the switching filter 76 controlled by the filter controller 216, and emission of resetting light 132 from the resetting light source 78, which is controlled by the light source controller 218, are displayed respectively on the display control panel 56, or may be output as sounds from the speaker 58, and may be sent or indicated from the communication unit 186 to the console 22 via a wireless communication link.

Operations of the Present Embodiment

The radiographic image capturing system 10 incorporating therein the electronic cassette 20 (20A through 20D) according to the present embodiment is basically constructed as described above. Operations of the radiographic image capturing system 10 will be described below with reference to FIGS. 16 through 26, and also to FIGS. 1 through 15 as needed.

More specifically, operations of the radiographic image capturing system 10, which incorporates the electronic cassette 20A according to the first example, will be described below with reference to FIGS. 16 through 26. However, the description of operations of the radiographic image capturing system 10 also is applicable to the electronic cassettes 20B through 20D according to the second through fourth examples, provided such operations are modified depending on the configurations of the electronic cassettes 20B through 20D.

Radiographic image capturing processes [1] through [7] according to different image capturing orders will be described below.

[1] The radiographic image capturing process according to an image capturing order including capturing of at least one still image of the subject 14, i.e., a radiographic image capturing mode for capturing at least one radiographic image of the subject 14, or capturing of a moving image at a frame rate lower than a frame rate threshold value Fth, i.e., a low-rate moving image capturing mode or a first moving image capturing mode (see FIGS. 16 and 17), will be described below.

The radiographic image capturing process is an image capturing process in which the light resetting process is not performed on the photodetector devices 94.

The light resetting process is not performed on the photodetector devices 94 if noise caused by dark current signals produced in a case where electric charges trapped by the impurity level are discharged again is low enough so as not to prevent a doctor from interpreting the captured radiographic image.

The frame rate threshold value Fth is a threshold value (see FIG. 20) used to determine whether the light resetting process should be carried out or not. If the frame rate of a moving image capturing mode is higher than the frame rate threshold value Fth, then it is judged that the light resetting process should be carried out. On the other hand, if the frame rate of a moving image capturing mode is lower than the frame rate threshold value Fth, then it is judged that the light resetting process should not be carried out.

Further, the low-rate moving image capturing mode refers to a moving image capturing mode at a frame rate lower than the frame rate threshold value Fth (normally, Fth=Fth0). A moving image capturing mode at a frame rate higher than the frame rate threshold value Fth will hereinafter be referred to as a high-rate moving image capturing mode, or a second moving image capturing mode.

Figure 16:
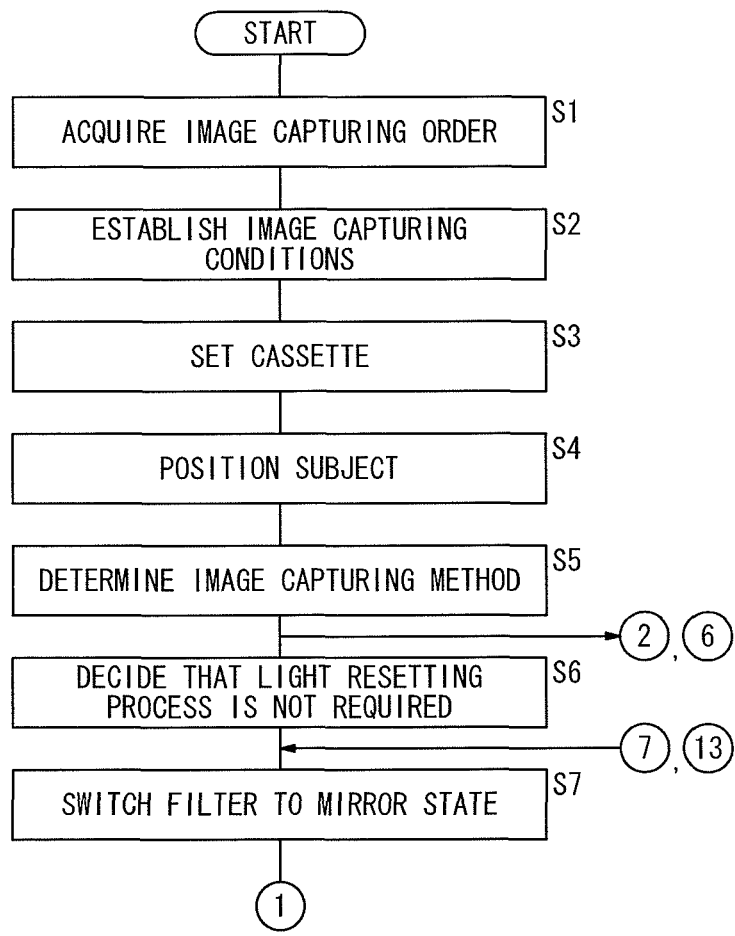
FIG. 16 is a flowchart of a basic operation sequence of the radiographic image capturing system shown in FIG. 1.

First, in step S1 shown in FIG. 16, the console 22 (see FIG. 1) acquires order information representing an image capturing order produced by the doctor in the RIS 26 or the HIS 28. In step S2, the doctor establishes image capturing conditions for the subject 14 based on the order information acquired by the console 22. The image capturing conditions refer to various conditions required for applying radiation 16 to a region to be imaged of the subject 14, e.g., a tube voltage and a tube current of the radiation source 30, a radiation exposure time, etc.

In step S3, the doctor grips the grip 52 (see FIGS. 2 and 3A) of the electronic cassette 20A, which has been placed in a given storage location, carries the electronic cassette 20A, and places the electronic cassette 20A on the image capturing base 12. In step S4, the doctor lays the subject 14 on the image capturing base 12 and the electronic cassette 20A so that the region to be imaged of the subject 14 is positioned within the image capturing area 50, thereby positioning the region to be imaged of the subject 14 with respect to the image capturing area 50.

Up to this time, the power supply 188 (see FIG. 15) has been supplying electric power to the cassette controller 182, the communication unit 186, and the display control panel 56. After positioning the subject 14, the doctor operates the display control panel 56 to indicate activation of the electronic cassette 20A. The cassette controller 182 then starts to supply electric power from the power supply 188 to the drive circuit 180 and the speaker 58. The bias power supply 192 starts applying a bias voltage to the pixels 190, i.e., the photodetector devices 94, which are now readied to store electric charges. The speaker 58 is also readied to output sounds representing audio signals from the cassette controller 182. As a result, the electronic cassette 20A switches from a sleep mode into an activated mode.

The cassette controller 182 sends a transmission request signal for requesting transmission of an image capturing order and image capturing conditions from the communication unit 186 to the console 22 via a wireless communication link. In response to the transmission request signal, the console 22 sends the image capturing order and the image capturing conditions to the electronic cassette 20A via a wireless communication link, and also sends the image capturing conditions to the radiation output device 18 via a wireless communication link. In the radiation output device 18, the received image capturing conditions are registered in the radiation source controller 32. In the electronic cassette 20A, the image capturing order and the image capturing conditions, which have been received, are registered in the cassette controller 182. The cassette controller 182 may also display the image capturing order and the image capturing conditions, which have been received, on the display control panel 56.

In step S5, the image capturing order determiner 210 of the cassette controller 182 determines an image capturing method included in the order information. At this time, the determined image capturing method represents capturing of at least one still image of the subject 14, or capturing of a moving image at a frame rate lower than the frame rate threshold value Fth (Fth0) (see FIG. 20), i.e., the low-rate moving image capturing mode. The image capturing order determiner 210 indicates the determined image capturing method to the light resetting operation determiner 214, and displays the determined image capturing method on the display control panel 56.

Based on the image capturing method indicated by the image capturing order determiner 210, the light resetting operation determiner 214 determines whether or not a light resetting process is to be performed on the pixels 190, i.e., the photodetector devices 94. Since the image capturing method represents capturing of at least one still image or the low-rate moving image capturing mode, in step S6, the light resetting operation determiner 214 decides that the pixels 190 do not need to be reset. The light resetting operation determiner 214 indicates the decision to the filter controller 216 and the light source controller 218, and displays the decision on the display control panel 56. The light resetting operation determiner 214 may also output a sound indicative of the decision from the speaker 58.

Based on the decision indicated by the light resetting operation determiner 214, the filter controller 216 prohibits voltage from being applied to the switching filter 76, and the light source controller 218 prohibits the resetting light source 78 from being energized. Therefore, in step S7, the light-regulating mirror film layer 122 of the switching filter 76 remains in a mirror state, and the resetting light source 78 does not emit resetting light 132.

Since the decisions made in steps S5 and S6 are displayed on the display control panel 56, by viewing the decisions displayed on the display control panel 56, the doctor can recognize that the light resetting process is not performed. If sounds representing the decisions made in steps S5 and S6 are output from the speaker 58, then by listening to sounds output from the speaker 58, the doctor can recognize that the light resetting process is not performed.

Furthermore, decisions may be sent from the communication unit 186 to the console 22 via a wireless communication link. In this case, the console 22 may send the received decisions to the display device 24 via a wireless communication link, so that the display device 24 can display the judgements. Accordingly, the doctor can recognize for sure that the pixels 190 have not been reset.

Figure 17:
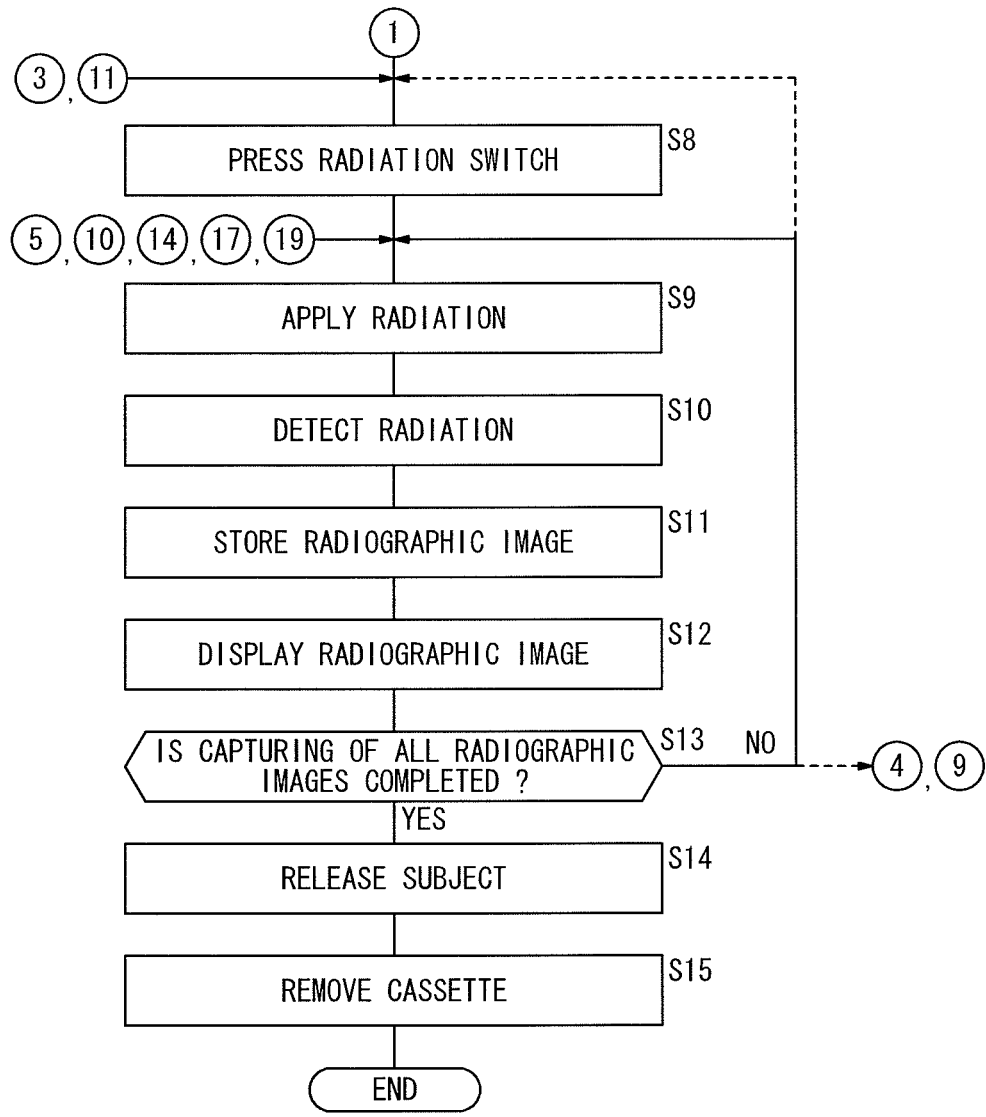
FIG. 17 is a flowchart of a basic operation sequence of the radiographic image capturing system shown in FIG. 1.

In step S8 shown in FIG. 17, after the preparatory processes in steps S1 through S7 have been performed on the radiographic image capturing system 10, the doctor presses the radiation switch 34 (see FIG. 1). The radiation source controller 32 prepares itself to apply radiation 16, and sends a notice signal indicating readiness to apply radiation 16 to the console 22 via a wireless communication link. The console 22 sends a synchronization control signal for achieving synchronism with application of radiation 16 from the radiation source 30 to the electronic cassette 20A via a wireless communication link. Upon receipt of the synchronization control signal by the cassette controller 182 of the electronic cassette 20A, the cassette controller 182 displays information indicative of readiness for application of radiation 16 on the display control panel 56 (see FIGS. 2 and 15). The cassette controller 182 may also output a sound indicative of such information from the speaker 58.

Thereafter, in step S9, by the doctor subsequently pressing the radiation switch 34, the radiation source controller 32 applies radiation 16 from the radiation source 30 to the region to be imaged of the subject 14 for a preset period of time according to the image capturing conditions. The radiation source controller 32 may send a notice signal indicative of start of application of radiation 16 to the console 22 via a wireless communication link at the same time that radiation 16 starts to be applied. The console 22 may transfer the received notice signal to the electronic cassette 20A. In response to reception of the notice signal, the cassette controller 182 of the electronic cassette 20A may display information indicative of application of radiation 16 on the display control panel 56, and may also output a sound indicative of such information from the speaker 58.

In step S10, at the time that radiation 16 passes through the region to be imaged of the subject 14 and is applied to the radiation detector 70 of the electronic cassette 20A, because the radiation detector 70 is of an ISS type as shown in FIGS. 3A and 4A, radiation 16 passes through the photodetector substrate 72, to arrive at the columnar crystalline structure 84 of the scintillator 74.

The columnar crystalline structure 84 emits visible light 130 (see FIGS. 11A and 11B) having an intensity corresponding to the intensity of the radiation 16. The visible light 130 travels from the columnar portion of the columnar crystalline structure 84 toward the non-columnar crystalline portion 82 and is made incident on the photodetector substrate 72. Although part of the visible light 130 travels from the columnar portion of the columnar crystalline structure 84 to the distal end portion thereof, because the light-regulating mirror film layer 122 of the switching filter 76 is in a mirror state (see FIGS. 11A and 11B), that part of the visible light 130 is reflected toward the photodetector substrate 72, and the reflected light (part of the visible light 130) is applied to the photodetector substrate 72 through the columnar crystalline structure 84 and the non-columnar crystalline portion 82. Consequently, at the photodetector substrate 72, because reflected light (visible light 130), which is reflected by the light-regulating mirror film layer 122 in the mirror state, is applied in addition to visible light 130 that is applied directly after conversion by the columnar crystalline structure 84, the sensitivity of the respective pixels 190 (the respective photodetector devices 94) of the photodetector substrate 72 with respect to visible light 130 can easily be increased.

The respective pixels 190 convert the applied visible light 130, which as noted above is applied through the planarization film 96, into electric signals and store the electric signals as electric charges. The electric charge information stored in the pixels 190, which represents a radiographic image of the region to be imaged of the subject 14, are read according to drive signals supplied from the cassette controller 182 (see FIG. 15) to the gate driver 198.

More specifically, the gate driver 198 successively selects the gate lines 194 from the 0th row of the matrix of pixels 190, and supplies gate signals to the selected gate lines 194 to turn on the TFTs 92 connected to the selected gate lines 194, thereby successively reading the electric charges stored in the pixels 190 one row at a time from the 0th row of the matrix of pixels 190. The electric charges read from the pixels 190 one row at a time are transferred along the signal lines 196 to the charge amplifiers 200 in respective columns of the matrix of pixels 190. Then, in step S11, the electric charges are processed by the multiplexer 202 and the A/D converter 204, and are stored as digital electric signals in the memory 184. More specifically, the memory 184 successively stores radiographic image information represented by the digital electric signals obtained from the rows of the matrix of pixels 190.

The radiographic image information stored in the memory 184 is sent, together with cassette ID information for identifying the electronic cassette 20A, from the communication unit 186 to the console 22 (see FIG. 1) via a wireless communication link. In step S12, the console 22 displays a radiographic image represented by the radiographic image information and the cassette ID information on the display device 24. The cassette controller 182 may also display the radiographic image and the cassette ID information on the display control panel 56.

The doctor confirms the radiographic image by observing the contents displayed on the display device 24 or the display control panel 56. Thereafter, in step S13, if capturing of all of the radiographic images registered in the image capturing order is completed (step S13: YES), then in step S14, the doctor releases the subject 14 from the image capturing base 12.

Then, the doctor operates the display control panel 56 to de-energize the electronic cassette 20A. The cassette controller 182 stops supplying electric power from the power supply 188 to the drive circuit 180 and the speaker 58. The supply of the bias voltage from the bias power supply 192 to the pixels 190 also is stopped. As a result, the electronic cassette 20A switches from the activated mode into a sleep mode.

In step S15, after having confirmed that nothing is displayed on the display control panel 56 and that the electronic cassette 20A has switched to the sleep mode, the doctor grips the grip 52 (see FIGS. 2 and 3A) of the electronic cassette 20A and carries the electronic cassette 20A to the given storage location.

In step S13, if the image capturing order includes a low-rate moving image capturing mode and capturing of all moving images is not yet completed (step S13: NO), then the radiation source controller 32 performs a next moving image capturing mode (second and subsequent radiographic images), and in step S9, controls the radiation source 30 to apply radiation 16 to the region to be imaged of the subject 14 according to the image capturing conditions.

In step S13, if the image capturing order includes capturing of a plurality of still images and capturing of all still images is not yet completed (step S13: NO), then the doctor carries out step S8 again in order to perform a next still image capturing mode (second and subsequent radiographic images).

As described above, for capturing at least one still image of the subject 14 or for a low-rate moving image capturing mode, in the case that the light resetting process is not performed with respect to the respective photodetector devices 94 (i.e., each of the pixels 190), a radiographic image capturing process is performed on the subject 14 while the light-regulating mirror film layer 122 of the switching filter 76 remains in the mirror state.

The radiographic image capturing process [1] for a case in which the light resetting process is not performed has been described above.

Next, radiographic image capturing processes [2] through [7], for cases in which the light resetting process is performed on the photodetector devices 94 (pixels 190), will be described below with reference to FIGS. 18 through 26.

Prior to describing the radiographic image capturing processes [2] through [7], the need for resetting the photodetector devices 94 or the pixels 190 with resetting light 132 will be described.

If the photodiodes of the photodetector devices 94 (see FIGS. 6A through 8, FIGS. 10A through 12B, and FIGS. 13B through 15) are made of amorphous silicon (a-Si) or the like, then some of the electric charges converted from visible light 130 are temporarily trapped by the impurity level of the amorphous silicon. If such trapped electrons are subsequently released due to a rise in temperature of the photodiodes, which may be caused upon capturing of a moving image at a high rate, unwanted current such as dark current is generated, possibly producing noise in a resultant radiographic image of the subject 14. As explained in the "Description of the Related Art," it heretofore has been customary to reduce noise by applying resetting light 132 to the photodiodes when radiation is not being applied to the subject 14, i.e., when a radiographic image of the subject 14 is not being captured, to thereby embed electric charges in the impurity level, so that electric charges converted from visible light 130 upon application of radiation 16 to the subject 14 will not be trapped by the impurity level.

According to the above process of the related art, however, since electric charges are embedded in a relatively shallow position, if the temperature of the photodiodes rises, almost all of the electric charges are discharged from the impurity level, making it ineffective at reducing noise. In the high-rate moving image capturing mode, since the temperature of the photodiodes rises due to repeated capturing of moving images over a long period of time, if the image capturing interval, i.e., the frame rate, and the time during which electric charges are discharged from the impurity level are comparable with each other, such electric charges tend to be more prominently discharged from the impurity level and at different rates between frames.

According to the present embodiment, it is desirable that electric charges be embedded sufficiently deeply in the impurity level to eliminate varying rates between frames, during which the electric charges are discharged due to an increase in the temperature of the photodiodes, and also to remove or correct noise caused by electric charges, which are discharged at a certain rate from radiographic images, by way of an image processing sequence.

On the other hand, the level of dark current also varies depending on the temperature of the photodiodes. In particular, the level of dark current becomes higher as the temperature of the photodiodes rises. Not only during the moving image capturing mode, but also if a radiographic image capturing process is performed over a long period of time, such as during capturing of still images at a reduced interval in the still image capturing mode, upon switching of the moving image capturing mode to the still image capturing mode, and upon switching of the still image capturing mode to the moving image capturing mode, the temperature of the photodiodes is likely to rise, and noise due to dark current signals is not negligible.

Figure 20:
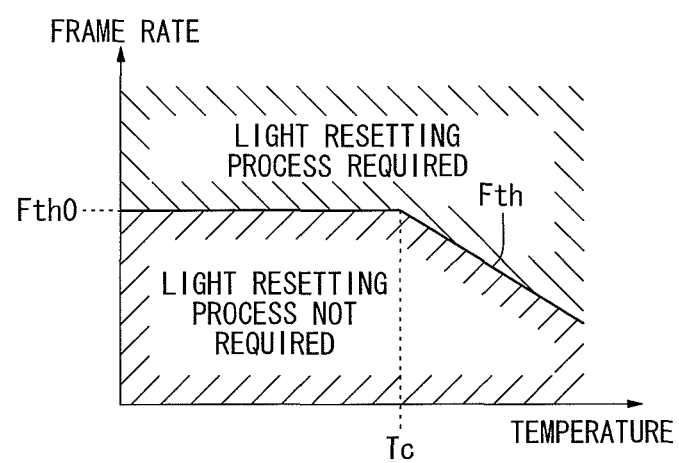
FIG. 20 is a graph showing how a frame rate threshold value changes depending on a temperature of photodiodes.

If noise due to a rise in temperature of the photodiodes increases to the extent that such noise is not negligible, then if the temperature of the photodiodes is higher than a threshold temperature Tc, as shown in FIG. 20, it is desirable to reduce the frame rate threshold value Fth from the initial value Fth0, and to determine whether or not the photodetector devices 94 should be reset in view of the temperature of the photodiodes, regardless of whether the low-rate moving image capturing mode or the high-rate moving image capturing mode has been indicated by the image capturing order.

In the radiographic image capturing processes, with the light resetting process being performed as shown in FIGS. 18 through 26, it is determined whether or not the light resetting process should be performed in view of the temperature of the photodetector devices 94, which include photodiodes made of amorphous silicon.

Radiographic image capturing processes [2] through [7] with the light resetting process being performed will be described separately below with reference to FIGS. 18 through 26.

[2] The radiographic image capturing process according to an image capturing order including a still image capturing mode or a low-rate moving image capturing mode, with the light resetting process being carried out at least once prior to the image capturing mode (see FIG. 18), shall be described below.

Since high-quality radiographic images are required, it is assumed that the light resetting process is performed at least once prior to the image capturing mode in order to acquire radiographic images with only slight noise therein. More specifically, even if the image capturing order described above with respect to the radiographic image capturing process [1] is given, it is assumed that the light resetting process is performed at least once prior to the image capturing mode, so as to acquire radiographic images of higher quality.

Figure 18:
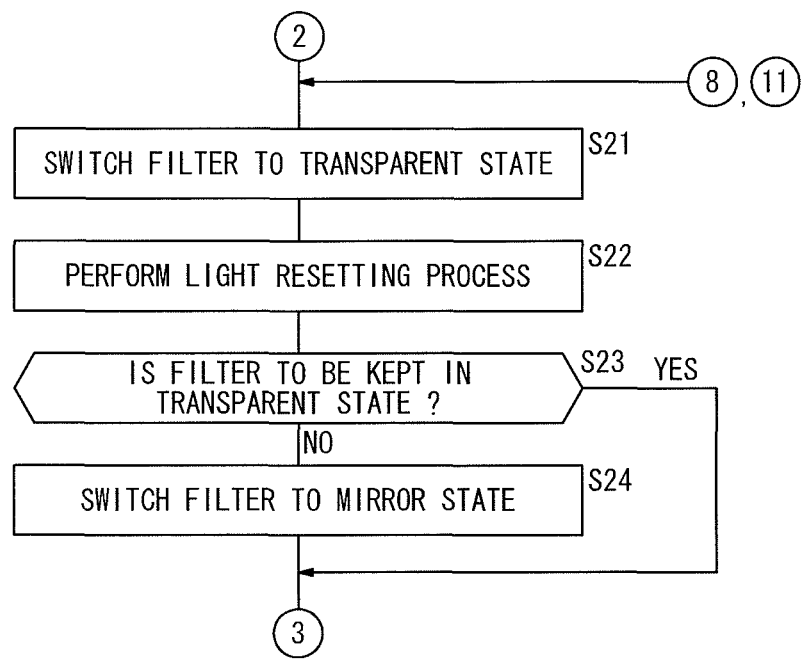
FIG. 18 is a flowchart of a switching sequence and a resetting sequence of the switching filter.

In step S21 shown in FIG. 18, after step S5 (see FIG. 16), the light resetting operation determiner 214 (see FIG. 15) decides that the light resetting process needs to be performed at least once prior to the image capturing mode, because the image capturing method identified by the image capturing order determiner 210 represents a radiographic image capturing mode for capturing at least one radiographic image or a low-rate moving image capturing mode. Then, the light resetting operation determiner 214 outputs the decision that the light resetting process needs to be performed at least once prior to the image capturing mode to the filter controller 216 and to the light source controller 218, while also displaying the decision on the display control panel 56. The speaker 58 may also output a sound representative of the decision.

Based on the decision from the light resetting operation determiner 214, in step S21, the filter controller 216 applies a voltage to the switching filter 76 (see FIG. 3A, FIG. 4A, FIG. 6A, FIGS. 9 through 12B, FIG. 13B and FIG. 14) in order to switch the light-regulating mirror film layer 122 from the mirror state to the transparent state. Based on the same decision, the light source controller 218 energizes the resetting light source 78 to start emitting resetting light 132.

Resetting light 132 passes through the light-regulating mirror film layer 122 and is applied to the photodetector substrate 72 via the scintillator 74, thereby starting the light resetting process for resetting the photodetector devices 94, i.e., the pixels 190, with resetting light 132 in step S22. Thereafter, the light source controller 218 de-energizes the resetting light source 78 so that emission of resetting light 132 is stopped, thereby finishing the light resetting process.

If, based on the decision from the light resetting operation determiner 214 in step S23, the filter controller 216 decides that it is necessary to return the light-regulating mirror film layer 122 to the mirror state (step S23: NO), then in step S24, the filter controller 216 applies a voltage, which is opposite in polarity to the voltage applied in step S21, to the switching filter 76 in order to switch the light-regulating mirror film layer 122 from the transparent state to the mirror state. Further, based on the determination result, if the filter controller 216 decides that it is necessary to keep the light-regulating mirror film layer 122 in the transparent state (step S23: YES), supply of voltage to the switching filter 76 is not carried out and the transparent state is maintained.

In this manner, after the light resetting process is finished, the radiographic image capturing system 10 executes step S8 shown in FIG. 17.

In step S23 shown in FIG. 18, the filter controller 216 determines whether or not the switching filter 76 should be kept in a transparent state. For example, such a decision is made in accordance with the following criteria (1) and (2).

(1) In a radiographic image capturing mode for capturing a single still image, a radiographic image with only slight noise therein can be acquired if resetting is performed once prior to the image capturing mode. Further, during image capturing, if the switching filter 76 is in the mirror state, then since visible light 130 traveling toward the switching filter 76 is reflected toward the photodetector substrate 72, the sensitivity of the photodetector devices 94 can easily be increased. In a radiographic image capturing mode for capturing a plurality of radiographic images or a low-rate moving image capturing mode, since the temperature of the photodiodes is not expected to rise significantly if images are captured over a relatively long interval, high-quality radiographic images can be captured even if the photodetector devices 94 are not reset prior to capturing of second and subsequent radiographic images. Accordingly, concerning such image capturing modes, the filter controller 216 may determine whether or not the light-regulating mirror film layer 122 should be returned to the mirror state, with the object of obtaining high sensitivity and acquiring high quality radiographic images.

(2) Even in a radiographic image capturing mode for capturing a plurality of radiographic images or a low-rate moving image capturing mode, if images are captured within a relatively short interval, then as the number of captured images increases, the temperature of the photodiodes rises. Thus, in capturing of second and subsequent images, if the light resetting process is not performed immediately before an image is captured, it is expected that noise due to dark current will adversely affect the radiographic images. Further, if the time required for the light-regulating mirror film layer 122 to switch between the mirror state and the transparent state is longer than the image capturing interval, then switching of the switching filter 76 may not be able to catch up with the frame rate of the moving image capturing mode. In such cases, the filter controller 216 may not return the light-regulating mirror film layer 122 to the mirror state, but may determine that the light-regulating mirror film layer 122 should be kept in the transparent state, for the purpose of performing the light resetting process reliably and to acquire radiographic images having only slight noise therein.

As described above, with the electronic cassette 20A (or the electronic cassette 20B) of an ISS type, since the photodetector substrate 72, the scintillator 74, the switching filter 76, and the resetting light source 78 are arranged successively in this order along the direction in which radiation 16 is applied, almost all of the radiation 16 is converted into visible light 130 by the columnar crystalline structure 84, and the possibility that radiation 16 will reach the switching filter 76 and the resetting light source 78 is extremely small. In accordance with an ISS type electronic cassette, therefore, the switching filter 76 and the resetting light source 78 are prevented from becoming degraded by radiation 16, and even if the light-regulating mirror film layer 122 is kept in a transparent state while radiation 16 is applied, the resetting light source 78 can be prevented from emitting resetting light 132 in error due to being irradiated with radiation 16.

Further, in the radiographic image capturing process [2], the light resetting process is performed at least once prior to the image capturing mode. After the light resetting process has been performed, in the case of an image capturing order for capturing still images, the light-regulating mirror film layer 122 is kept in the mirror state, and capturing of still images is carried out. On the other hand, in the case of a low rate moving image capturing mode, the light-regulating mirror film layer 122 is placed in the mirror state and capturing of moving images is carried out, or alternatively, the light-regulating mirror film layer 122 is placed in the transparent state and capturing of moving images is carried out.

[3] The radiographic image capturing process according to an image capturing order including capturing of a plurality of images (a still image capturing mode or a moving image capturing mode) with the light resetting process being performed between image capturing cycles (see FIG. 19) shall be described below.

It is assumed that the light resetting process is performed while images are successively being captured in an image capturing mode for capturing a plurality of still images, a low-rate moving image capturing mode, or a high-rate moving image capturing mode.

In step S13 (see FIG. 17), if capturing of all moving images is not yet completed (step S13: NO), then in step S25 of FIG. 19, the light resetting operation determiner 214 (see FIG. 15) decides that the light resetting process needs to be performed between image capturing cycles (step S25: YES), because the decision made by the image capturing order determiner 210 represents capturing of a plurality of images (an image capturing mode for capturing a plurality of still images or a moving image capturing mode). The light resetting operation determiner 214 outputs the decision to the filter controller 216 and the light source controller 218, while also displaying the decision on the display control panel 56. The light resetting operation determiner 214 may also output a sound indicative of the decision from the speaker 58.

Based on the decision from the light resetting operation determiner 214, in step S26, the filter controller 216 determines whether or not the light-regulating mirror film layer 122 (see FIG. 6A, FIGS. 9 through 12B, FIG. 13B and FIG. 14) is in the mirror state. In step S26, if the light-regulating mirror film layer 122 is in the mirror state (step S26: YES), then in step S27, similar to step S21 (see FIG. 18), the filter controller 216 applies a voltage to the switching filter 76 in order to switch the light-regulating mirror film layer 122 from the mirror state to the transparent state.

Based on the same decision, the light source controller 218 energizes the resetting light source 78 to start emitting resetting light 132, in the same manner as with step S22. More specifically, in step S28, resetting light 132 passes through the light-regulating mirror film layer 122 and is applied to the photodetector substrate 72 via the scintillator 74, thereby resetting the photodetector devices 94, i.e., the pixels 190.

Thereafter, the light source controller 218 de-energizes the resetting light source 78 so as to stop emitting resetting light 132. In step S29, the filter controller 216 applies a voltage to the switching filter 76, which is opposite in polarity to the voltage in step S27, to thereby switch the light-regulating mirror film layer 122 from the transparent state to the mirror state. Thereafter, control goes back to step S9 shown in FIG. 17, in which the radiographic image capturing system 10 performs a next radiographic image capturing process.

In the radiographic image capturing process [3], therefore, steps S25 through S29 are carried out between image capturing cycles with respect to an image capturing order, which includes an image capturing mode for capturing a plurality of still images, a low-rate moving image capturing mode, or a high-rate moving image capturing mode. Accordingly, the light-regulating mirror film layer 122 is switched alternately between the mirror state and the transparent state during one frame, and the light resetting process is performed during the transparent state.

If the light-regulating mirror film layer 122 is in the transparent state (step S26: NO), i.e., if the moving image capturing mode is carried out with the light-regulating mirror film layer 122 being kept in the transparent state, then the filter controller 216 does not supply any voltage to the switching filter 76, so as to continuously maintain the light-regulating mirror film layer 122 in a transparent state, and together therewith, in step S30, the light source controller 218 energizes the resetting light source 78 to perform the light resetting process on the pixels 190, in the same manner as in steps S22 and S28. Thereafter, the light source controller 218 de-energizes the resetting light source 78 to stop emitting resetting light 132. Then, control goes back to step S9, and the radiographic image capturing system 10 performs a next radiographic image capturing process.

In this manner, according to the radiographic image capturing process [3], if the light-regulating mirror film layer 122 is kept in the transparent state, then the light resetting process can be performed between image capturing cycles, and thereafter, the light-regulating mirror film layer 122 can be kept in a transparent state without switching back to the mirror state. In particular, if the image capturing order includes a high-rate moving image capturing mode, then since the switching time of the light-regulating mirror film layer 122 may not be able to catch up with the frame rate of the high-rate moving image capturing mode, the light resetting process can reliably be performed between image capturing cycles by maintaining the light-regulating mirror film layer 122 in the transparent state.

In step S25, if the light resetting operation determiner 214 decides that the light resetting process does not need to be performed between image capturing cycles (step S25: NO), even though the decision made by the image capturing order determiner 210 represents capturing of a plurality of images, then the light resetting operation determiner 214 outputs the decision to the filter controller 216 and to the light source controller 218, while displaying the decision on the display control panel 56. The light resetting operation determiner 214 may also output a sound indicative of the decision from the speaker 58. Thereafter, control goes back to step S9 shown in FIG. 19, in which the radiographic image capturing system 10 performs a next radiographic image capturing process.

In step S25, the light resetting operation determiner 214 may determine whether or not the light resetting process needs to be performed between image capturing cycles in view of the temperature of the photodetector devices 94, in addition to the above image capturing method (an image capturing mode for capturing a plurality of still images or a moving image capturing mode).

For example, among pixel values of the electric signals read from the pixels 190 in a preceding image capturing cycle, the pixel values of electric signals read from the pixels 190, which are located within a region not irradiated with radiation 16, are assumed to be dark current dependent pixel values. Based on the pixel values of (dark current dependent) electric signals read from such pixels 190, the temperature detector 212 detects the temperature of the pixels 190, i.e., the photodiodes, and outputs the detected temperature to the light resetting operation determiner 214.

In this case, in step S25, the light resetting operation determiner 214 identifies the frame rate threshold value Fth corresponding to the temperature detected by the temperature detector 212 in FIG. 20, and compares the frame rate threshold value Fth with the frame rate of the image capturing method identified by the image capturing order determiner 210. If the frame rate of the identified image capturing method is higher than the frame rate threshold value Fth dependent on the detected temperature, then in step S25, the light resetting operation determiner 214 determines that the pixels 190 need to be reset (step S25: YES). If the frame rate of the identified image capturing method is lower than the frame rate threshold value Fth dependent on the detected temperature, then in step S25, the light resetting operation determiner 214 determines that the pixels 190 do not need to be reset (step S25: NO).

If the temperature detected by the temperature detector 212 is lower than the threshold temperature Tc, and the frame rate threshold value Fth is at the initial value Fth0, then the light resetting operation determiner 214 does not determine whether the light resetting process needs to be performed in view of the temperature of the photodetector devices 94, but may determine whether the light resetting process needs to be performed simply by comparing the frame rate of the image capturing method with the frame rate threshold value Fth0.

In the radiographic image capturing processes [2] and [3], the subject 14 is imaged with radiation 16 according to an image capturing order, including at least one of an image capturing mode for capturing at least one still image, a low-rate moving image capturing mode, and a high-rate moving image capturing mode.

Figure 21A:
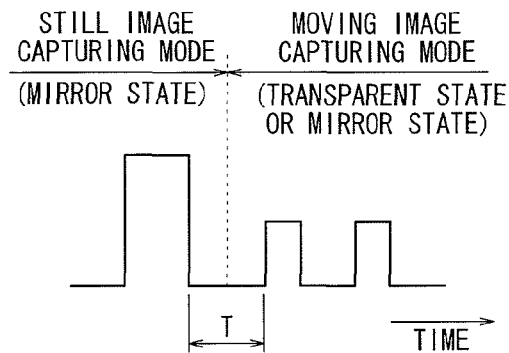
FIG. 21A is a timing chart showing switching from a still image capturing mode to a moving image capturing mode.
Figure 21B:
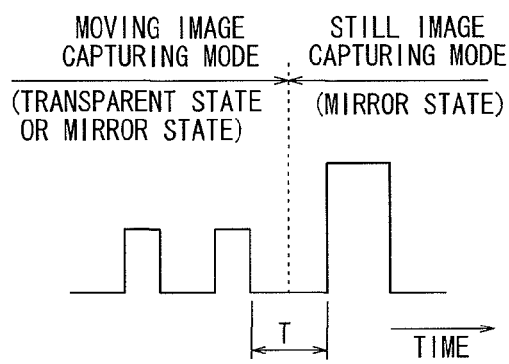
FIG. 21B is a timing chart showing switching from the moving image capturing mode to the still image capturing mode.
Figure 21C:
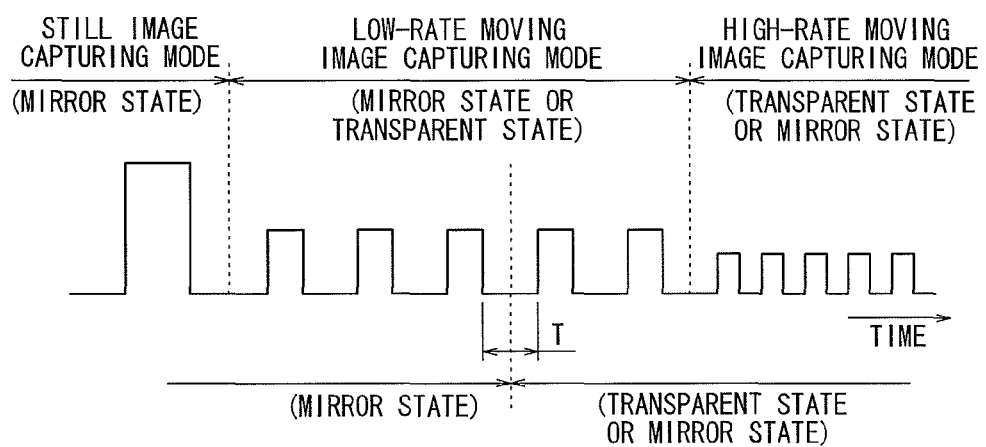
FIG. 21C is a timing chart showing switching between the still image capturing mode, a low-rate moving image capturing mode, and a high-rate moving image capturing mode.
Figure 22:
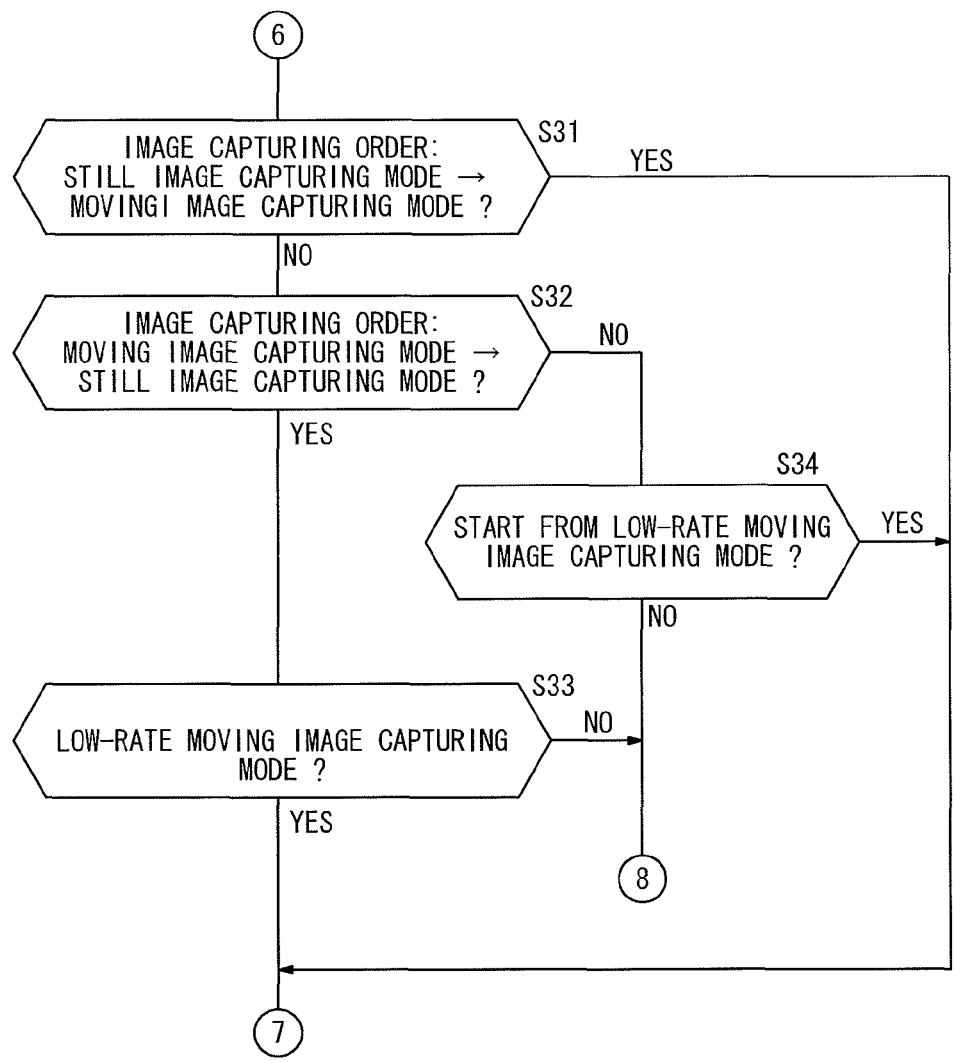
FIG. 22 is a flowchart of an operation sequence for determining an image capturing order.

However, as shown in FIGS. 21A through 21C, for example, certain image capturing orders include two or more image capturing modes, not just one image capturing mode. For example, FIG. 21A shows an image capturing order in which a still image capturing mode switches to a moving image capturing mode. FIG. 21B shows an image capturing order in which a moving image capturing mode switches to a still image capturing mode. FIG. 21C shows an image capturing order in which a still image capturing mode switches to a low-rate moving image capturing mode and then to a high-rate moving image capturing mode.

According to an image capturing order including two or more image capturing modes, the light-regulating mirror film layer 122 switches between the mirror state and the transparent state at a timing (time period T) at which the image capturing modes are switched (see FIGS. 21A and 21B), or alternatively, since it is time-consuming to switch the light-regulating mirror film layer 122 at a timing at which the image capturing modes are changed (i.e., since the switching time is unable to catch up with the frame rate of the moving image capturing mode) the state of the light-regulating mirror film layer 122 may be switched in advance, during a period in which the image capturing interval is relatively long. (see FIG. 21C).

Radiographic image capturing processes [4] through [7] and light resetting processes for image capturing orders, which include two or more image capturing modes, will be described below with reference to FIGS. 22 through 26.

[4] A radiographic image capturing process according to an image capturing order including, in this order, a sequence of an image capturing mode for capturing at least one still image and a moving image capturing mode, with the switching filter 76 switching between the mirror state and the transparent state at a timing at which the still image capturing mode is switched to the moving image capturing mode, will be described below (see FIG. 21A).

In the still image capturing mode, the light-regulating mirror film layer 122 (see FIG. 6A, FIGS. 9 through 12B, FIG.

13B and FIG. 14) is in the mirror state. After a time period T, in which the still image capturing mode switches to the moving image capturing mode, the light-regulating mirror film layer 122 remains in the mirror state, remains in the transparent state, or switches alternately between the mirror state and the transparent state, depending on the frame rate of the moving image capturing mode. The light-regulating mirror film layer 122 switches between the mirror state and the transparent state during the time period T. The moving image capturing mode in the radiographic image capturing process [4] refers to either a low-rate moving image capturing mode or a high-rate moving image capturing mode.

If the image capturing method included within the image capturing order represents, in this order, a sequence of a still image capturing mode and a moving image capturing mode (step S31: YES) (see FIG. 22), then after step S5 shown in FIG. 16, control proceeds to step S7 (see FIG. 16) in which the light-regulating mirror film layer 122 is set to the mirror state, and the still image capturing mode is carried out.

Thereafter, in step S13, after it has been decided that capturing of all radiographic images is not yet completed (step S13: NO) (see FIG. 17), if the decision sent from the image capturing order determiner 210 (see FIG. 15) indicates a sequence of a still image capturing mode and a moving image capturing mode in this order (step S41: YES) (see FIG. 23), then in step S42, the light resetting operation determiner 214 determines whether or not the present time represents a timing at which the still image capturing mode is switched to the moving image capturing mode.

In step S42, if the light resetting operation determiner 214 decides that the present time does not represent a timing at which the still image capturing mode is switched to the moving image capturing mode, i.e., that the next mode also is a still image capturing mode (step S42: NO), then the light resetting operation determiner 214 displays the decision on the display control panel 56. The doctor confirms the decision displayed on the display control panel 56, and control goes back to step S8 in FIG. 17, in order to perform a next still image capturing mode again.

On the other hand, if the light resetting operation determiner 214 decides that the present time is a timing during the time period T, at which the still image capturing mode is switched to the moving image capturing mode (step S42: YES), then in step S43, the light resetting operation determiner 214 determines whether or not the light resetting process should be performed.

If the preceding image capturing mode is a still image capturing mode with a relatively high radiation dose, whereas the next image capturing mode is a moving image capturing mode with a relatively low radiation dose, then the light resetting operation determiner 214 determines that the light resetting process needs to be performed (step S43: YES). The light resetting operation determiner 214 outputs the decision indicating that the light resetting process needs to be performed to the filter controller 216 and to the light source controller 218, and displays the decision on the display control panel 56. The light resetting operation determiner 214 may also output a sound indicative of the decision from the speaker 58.

In step S44, the filter controller 216 applies a voltage to the switching filter 76 (see FIG. 3A, FIG. 4A, FIG. 6A, FIGS. 9 through 12B, FIG. 13B and FIG. 14) to switch the light-regulating mirror film layer 122 from the mirror state to the transparent state. The light source controller 218 energizes the resetting light source 78 to start emitting resetting light 132. As a result, in step S45, the resetting light 132 passes through the light-regulating mirror film layer 122, and is applied to the photodetector substrate 72 through the scintillator 74, thereby performing the light resetting process with respect to the pixels 190. Thereafter, the light source controller 218 stops emission of resetting light 132 from the resetting light source 78, whereby the resetting process is completed. On the other hand, in step S46, the filter controller 216 determines whether or not the moving image capturing mode to be performed next is a low rate moving image capturing mode.

Since the low-rate moving image capturing mode is a moving image capturing mode at a relatively low frame rate, the image capturing interval is comparatively long and the temperature of the photodiodes does not rise significantly, and thus, the light resetting process may not be necessary. Further, since the image capturing interval is comparatively long, if the light resetting process is carried out, it is possible to provide a time period during which the switching filter 76 can be switched between image capturing cycles.

If the next moving image capturing mode is a low-rate moving image capturing mode (step S46: YES), then in step S47, the filter controller 216 applies a voltage, which is opposite in polarity to the voltage in step S44, to the switching filter 76 in order to switch the light-regulating mirror film layer 122 from the transparent state to the mirror state. After step S47, step S9 in FIG. 17 is carried out to start the low-rate moving image capturing mode.

In step S43, in the case that the temperature of the photodiodes is not particularly high since the time period T in FIG. 21A is relatively long, or in the event that the effect of noise due to dark current is small even if the resetting operation is not performed, or if the previous image capturing mode was a still image capturing mode at a comparatively low radiation dose, the light resetting operation determiner 214 determines that resetting is unnecessary (step S43: NO), and the determination result is output to the filter controller 216 and the light source controller 218, while also being displayed on the display control panel 56. Thereafter, the filter controller 216 carries out the determination process of step S46.

Further, if the next moving image capturing mode is a high-rate moving image capturing mode (step S46: NO), then in step S48, the filter controller 216 determines that the light-regulating mirror film layer 122 should remain in the transparent state. Thereafter, step S9 of FIG. 17 is carried out to start the high-rate moving image capturing mode.

If the decision in step S43 is negative (step S43: NO), then there is a possibility that the light-regulating mirror film layer 122 will presently be in a mirror state. Therefore, in step S46, if the filter controller 216 determines that the next moving image capturing mode is a high-rate moving image capturing mode (step S46: NO), then in step S48, the filter controller 216 may apply a voltage to the switching filter 76 in order to switch the light-regulating mirror film layer 122 from the mirror state to the transparent state.

Figure 23:
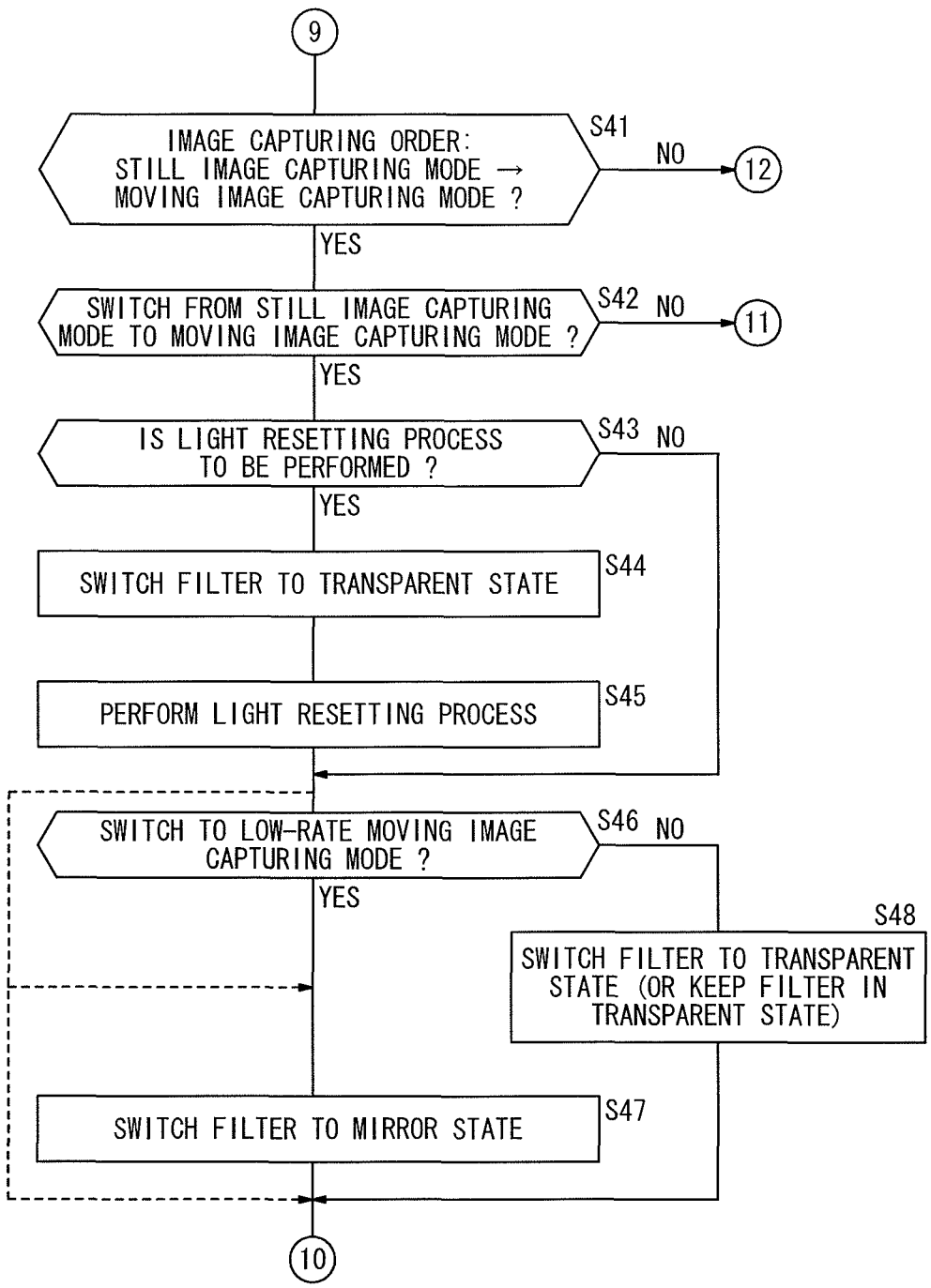
FIG. 23 is a flowchart of a switching sequence and a resetting sequence of the switching filter.

If the light-regulating mirror film layer 122 is to be kept in a mirror state even during the moving image capturing mode (low rate moving image capturing mode) following the still image capturing mode, or as described in [3] above, if within one frame, the light-regulating mirror film layer 122 is switched alternately between the mirror state and the transparent state and resetting is performed in the moving image capturing mode (e.g., the high rate moving image capturing mode), then the process of step S46 may be skipped, as indicated by the broken lines in FIG. 23, and step S47 may be carried out to switch the light-regulating mirror film layer 122 to the mirror state.

In the moving image capturing mode (e.g., a high-rate moving image capturing mode), the light-regulating mirror film layer 122 may be kept in the transparent state, or if the switching time of the light-regulating mirror film layer 122 is longer than the frame rate, steps S46 and S47 may be skipped.

[5] The radiographic image capturing process according to an image capturing order including a sequence of a moving image capturing mode and an image capturing mode for capturing at least one still image in this order, while the switching filter 76 switches between the mirror state and the transparent state at a timing at which the moving image capturing mode is switched to the still image capturing mode (see FIG. 21B), will be described below.

A case shall be described in which, in the moving image capturing mode, the light-regulating mirror film layer 122 (see FIG. 6A, FIGS. 9 through 12B, FIG. 13B and FIG. 14) is kept in the mirror state, is kept in the transparent state, or alternatively, switches between the mirror state and the transparent state in one frame, and after a time period T during which the moving image capturing mode switches to the still image capturing mode, the light-regulating mirror film layer 122 remains in the mirror state in the still image capturing mode. Accordingly, during the time period T in which the moving image capturing mode switches to the still image capturing mode, the state of the light-regulating mirror film layer 122 also is changed. The moving image capturing mode in the radiographic image capturing process [5] may also refer to either a low-rate moving image capturing mode or a high-rate moving image capturing mode.

First, after step S5 in FIG. 16, if the image capturing method included within the image capturing order represents, in this order, a sequence of a moving image capturing mode and a still image capturing mode in step S31 (step S31: NO) and in step S32 (step S32: YES) (see FIG. 22), and also if the moving image capturing mode is a low-rate moving image capturing mode (step S33: YES), then in step S7 and subsequent steps, the low-rate moving image capturing mode is carried out with the light-regulating mirror film layer 122 being in the mirror state.

Figure 19:
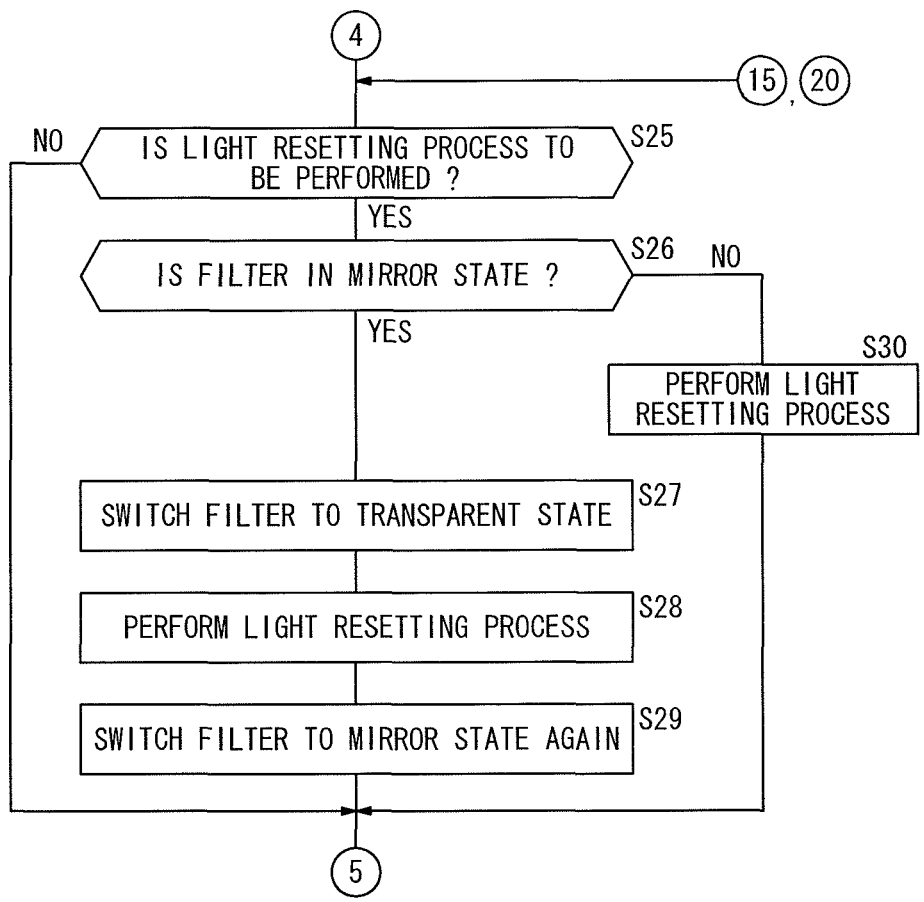
FIG. 19 is a flowchart of a switching sequence and a resetting sequence of the switching filter.

On the other hand, if the moving image capturing mode is a high-rate moving image capturing mode (step S33: NO), then control proceeds to steps S21 through S24 in FIG. 18. Step S8 and subsequent steps in FIG. 19 are carried out after the photodetector devices 94 have been reset prior to capturing of images.

Thereafter, in step S13, after it has been decided that capturing of all radiographic images is not yet completed (step S13: NO) (see FIG. 17), since the decision sent from the image capturing order determiner 210 indicates, in this order, a sequence of a moving image capturing mode and a still image capturing mode in step S41 (step S41: NO) (see FIG. 23) and step S51 (step S51: YES) (see FIG. 24), in step S52, the light resetting operation determiner 214 determines whether or not the present time represents a timing at which the moving image capturing mode is switched to the still image capturing mode.

In step S52, if the light resetting operation determiner 214 determines that the present time represents a timing at which the moving image capturing mode is switched to the still image capturing mode, i.e., that the next mode is a still image capturing mode during the time period T (step S52: YES), then in step S53, the light resetting operation determiner 214 determines whether or not the light resetting process is to be performed.

If a radiographic image with only slight noise is to be acquired in a still image capturing mode, or if the frame rate of a moving image capturing mode is higher than the frame rate threshold value Fth (see FIG. 20) depending on the temperature of the photodiodes, then in step S53, the light resetting operation determiner 214 determines that the light resetting process needs to be performed (step S53: YES). The light resetting operation determiner 214 outputs the decision indicating that the light resetting process is to be performed to the filter controller 216 and to the light source controller 218, while also displaying the decision on the display control panel 56. The light resetting operation determiner 214 may also output a sound indicative of the decision from the speaker 58.

In step S54, the filter controller 216 applies a voltage to the switching filter 76 to switch the light-regulating mirror film layer 122 from the mirror state to the transparent state. The light source controller 218 energizes the resetting light source 78 to start emitting resetting light 132. In step S55, resetting light 132 passes through the light-regulating mirror film layer 122 and is applied to the photodetector substrate 72 through the scintillator 74, thereby starting a light resetting process for resetting the photodetector devices 94, i.e., the pixels 190. Thereafter, control proceeds to step S7 in FIG. 16, to switch the light-regulating mirror film layer 122 to the mirror state. Then, step S8 and subsequent steps in FIG. 17 are carried out, to thereby perform the still image capturing mode.

On the other hand, in step S52, if the light resetting operation determiner 214 determines that the present time is not a timing at which the moving image capturing mode should switch to the still image capturing mode, i.e., that the next mode is also a moving image capturing mode (step S52: NO), then in step S56, the light resetting operation determiner 214 determines whether or not the next moving image capturing mode is a low-rate moving image capturing mode.

If the next moving image capturing mode is a low-rate moving image capturing mode (step S56: YES), then step S9 in FIG. 17 is performed. If the next moving image capturing mode is a high-rate moving image capturing mode (step S56: NO), then step S25 in FIG. 19 is performed.

If the time period T is long, and it is expected that high-quality radiographic images with only slight noise therein can be acquired in the still image capturing mode even if the light resetting process is not performed, or if the frame rate of the moving image capturing mode is lower than the frame rate threshold value Fth depending on the temperature of the photodiodes, then in step S53, the light resetting operation determiner 214 determines that the light resetting process does not need to be performed (step S53: YES). The light resetting operation determiner 214 displays the decision on the display control panel 56. Thereafter, in step S8 and subsequent steps in FIG. 17, the still image capturing mode is carried out.

Figure 24:
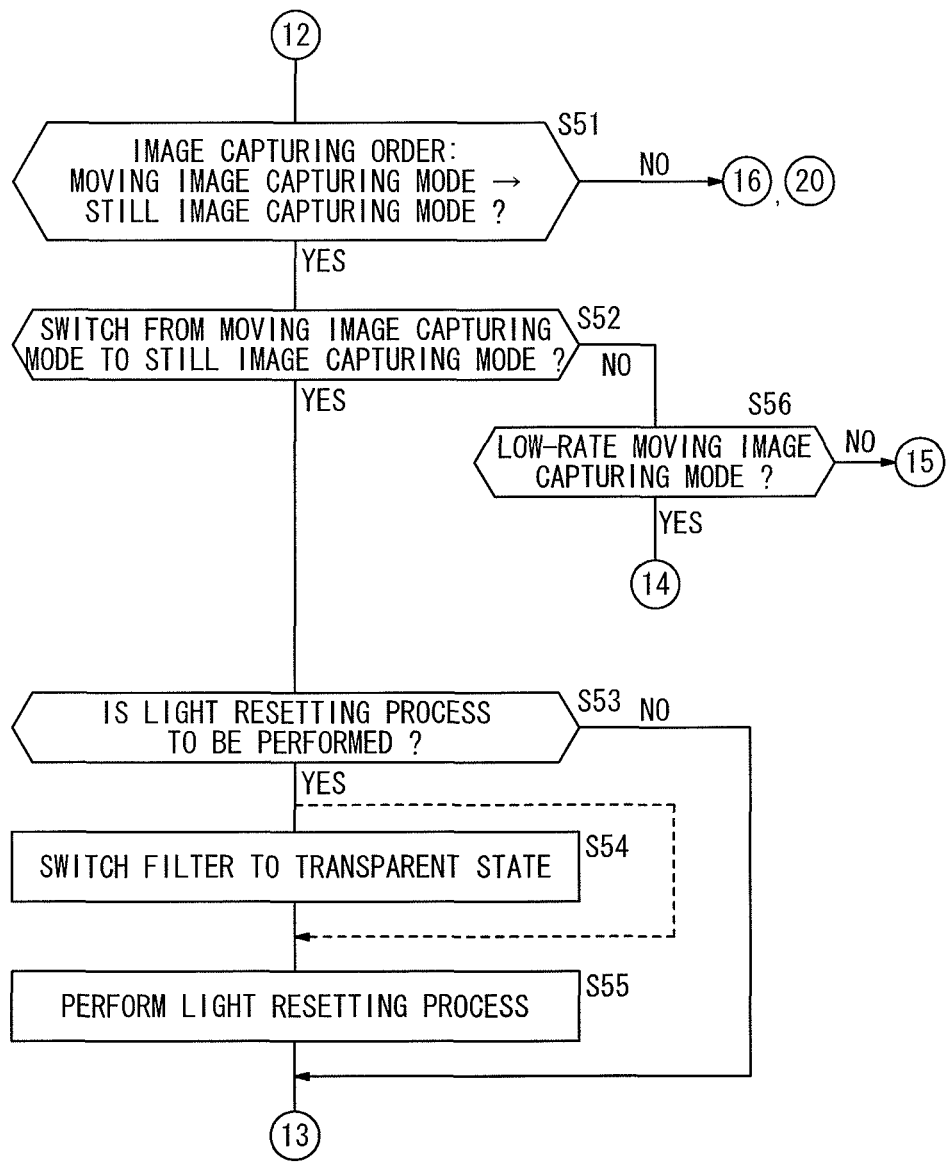
FIG. 24 is a flowchart of a switching sequence and a resetting sequence of the switching filter.

Furthermore, during the moving image capturing mode, if the light-regulating mirror film layer 122 is to be kept in a transparent state, then as shown by the broken lines in FIG. 24, step S54 may be skipped, and the light resetting operation of step S55 may be carried out directly.

In step S53, if the light resetting operation determiner 214 determines whether or not the light resetting process should be performed based on the temperature of the photodiodes, then, as described above with respect to the radiographic image capturing process [3], the light resetting operation determiner 214 may detect the temperature of the photodiodes from pixel values read from pixels 190 that are not irradiated with radiation 16, so as to determine whether or not the light resetting process should be performed or not based on the frame rate threshold value Fth (or Fth0) depending on the detected temperature and the frame rate of the moving image capturing mode.

[6] The radiographic image capturing process according to an image capturing order including two moving image capturing modes having different frame rates (see part of FIG. 21C) shall be described below.

In this case, the radiographic image capturing process is performed in a sequence of a low-rate moving image capturing mode and a high-rate moving image capturing mode in this order, or in a sequence of a high-rate moving image capturing mode and a low-rate moving image capturing mode in this order.

According to the radiographic image capturing process [6], unlike the radiographic image capturing processes [4] and [5], even if the frame rate is changed during the radiographic image capturing process (due to switching from a low-rate moving image capturing mode to a high-rate moving image capturing mode, or due to switching from a high-rate moving image capturing mode to a low-rate moving image capturing mode) depending on the temperature of the photodiodes or the image capturing interval, the light-regulating mirror film layer 122 (see FIG. 6A, FIGS. 9 through 12B, FIG. 13B and FIG. 14) may continue to be kept in the transparent state, or alternatively the light-regulating mirror film layer 122 may continue to be switched alternately between the mirror state and the transparent state in one frame.

After step S5 in FIG. 16, the two moving image capturing modes included in the image capturing order are successively carried out in step S31 (step S31: NO) (see FIG. 22) and step S32 (step S32: NO), and also if the image capturing order indicates that the low-rate moving image capturing mode is initially carried out (step S34: YES), then in step S7 and subsequent steps in FIG. 16, the low-rate moving image capturing mode is carried out with the light-regulating mirror film layer 122 being set to the mirror state.

On the other hand, if the image capturing order indicates that the high-rate moving image capturing mode is initially carried out (step S34: NO), then prior to capturing of images, the sequence of steps S21 through S24 in FIG. 18 is carried out, and the sequence of step S8 and subsequent steps in FIG. 17 is carried out after the light resetting process.

After it has been decided that capturing of all moving images is not yet completed (step S13: NO), if the decision from the image capturing order determiner 210 indicates that two image capturing modes are successively carried out in step S41 (step S41: NO) in FIG. 23 and in step S51 (step S51: NO) in FIG. 24, and also, in step S61, if the decision indicates that a low-rate moving image capturing mode and a high-rate moving image capturing mode are successively carried out in this order (step S61: YES) in FIG. 25, then in step S62, the light resetting operation determiner 214 (see FIG. 15) determines whether or not the light-regulating mirror film layer 122 should be switched to the transparent state.

More specifically, since the image capturing interval of the high-rate moving image capturing mode is shorter than the image capturing interval of the low-rate moving image capturing mode, even if the light-regulating mirror film layer 122 is switched alternately to the mirror state and the transparent state during one frame, it is difficult to perform the light resetting process if the switching time is longer than the image capturing interval.

Consequently, if switching of the light-regulating mirror film layer 122 to the mirror state or the transparent state cannot catch up with the frame rate of the high-rate moving image capturing mode, then as shown in FIG. 21C, it is desirable to switch the light-regulating mirror film layer 122 from the mirror state to the transparent state during the low-rate moving image capturing mode, the image capturing interval of which is relatively long.

Figure 25:
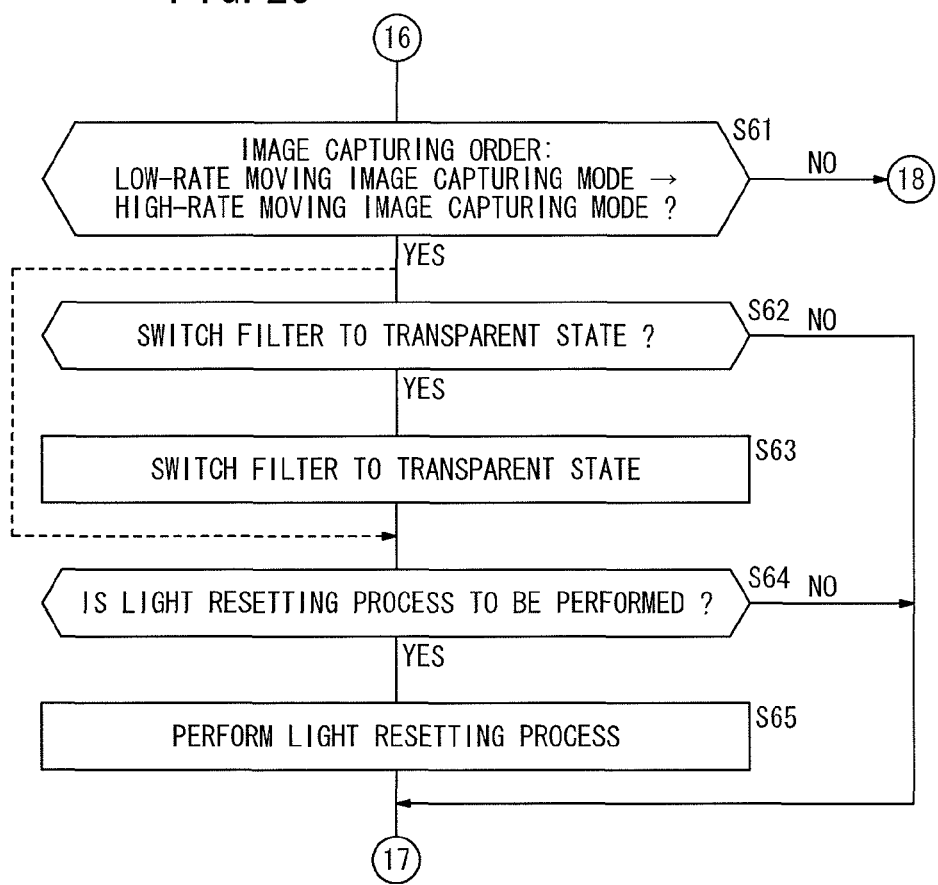
FIG. 25 is a flowchart of a switching sequence and a resetting sequence of the switching filter.
Figure 26:
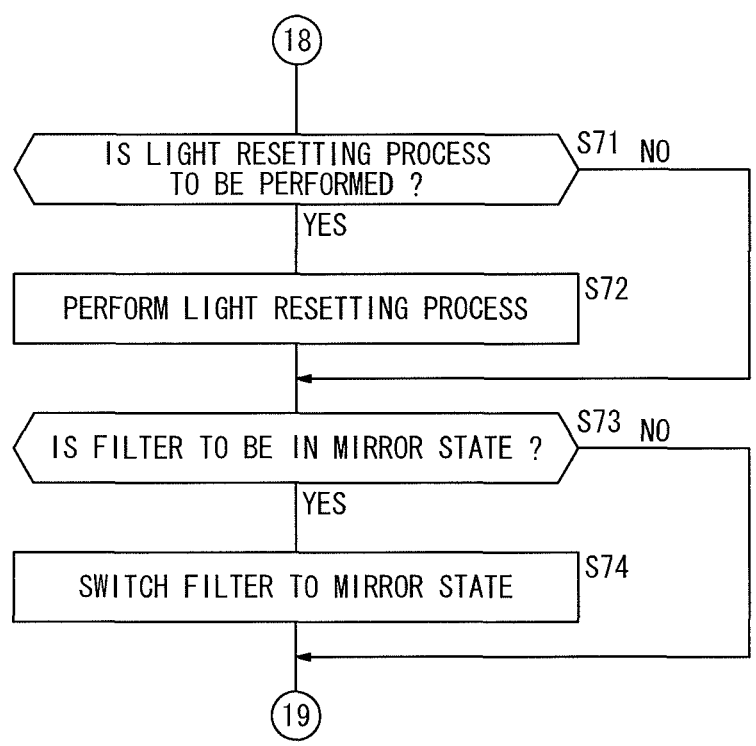
FIG. 26 is a flowchart of a switching sequence and a resetting sequence of the switching filter.

In step S62 of FIG. 25, if the light resetting operation determiner 214 determines that the light-regulating mirror film layer 122 is to switch from the mirror state to the transparent state (step S62: YES), then the light resetting operation determiner 214 outputs the decision to the filter controller 216 while also displaying the decision on the display control panel 56. In step S63, the filter controller 216 applies a voltage to the switching filter 76 (see FIG. 3B, FIG. 4A, FIG. 6A, FIGS. 9 through 12B, FIG. 13B and FIG. 14), to thereby switch the light-regulating mirror film layer 122 from the mirror state to the transparent state.

Then, in step S64, the light resetting operation determiner 214 determines whether or not the light resetting process is necessary.

If the frame rate of the low-rate moving image capturing mode is higher than the frame rate threshold value Fth dependent on the temperature of the photodiodes (see FIG. 20), then in step S64, the light resetting operation determiner 214 determines that the light resetting process is necessary (step S64: YES), and outputs the decision that the light resetting process needs to be performed to the filter controller 216 and to the light source controller 218, while displaying the decision on the display control panel 56. The speaker 58 may also output a sound representative of the decision.

The filter controller 216 keeps the light-regulating mirror film layer 122 in a transparent state, and the light source controller 218 energizes the resetting light source 78 to start emitting resetting light 132. In step S65, resetting light 132 passes through the light-regulating mirror film layer 122 and is applied to the photodetector substrate 72 through the scintillator 74, thereby resetting the photodetector devices 94, i.e., the pixels 190. After the light resetting process is finished, the light-regulating mirror film layer 122 is kept in the transparent state. Then, step S9 and the subsequent steps shown in FIG. 17 are carried out, i.e., the low-rate moving image capturing mode is performed.

On the other hand, in step S62, the light resetting operation determiner 214 decides that the light-regulating mirror film layer 122 should remain in the mirror state (step S62: NO), i.e., if switching of the light-regulating mirror film layer 122 to the mirror state or the transparent state can sufficiently catch up with the frame rate of the high-rate moving image capturing mode, or if the light-regulating mirror film layer 122 should be kept in the mirror state because a certain time period remains prior to switching from the low-rate moving image capturing mode to the high-rate moving image capturing mode, then steps S63 through S65 are skipped, and step S9 and subsequent steps are carried out while the light-regulating mirror film layer 122 remains in the mirror state.

Further, in step S64, if the light resetting operation determiner 214 decides that the light resetting process is not necessary (step S64: NO), even if the light-regulating mirror film layer 122 switches to the transparent state, then step S9 and subsequent steps are carried out while the light-regulating mirror film layer 122 is kept in the transparent state.

If the light-regulating mirror film layer 122 has already been in a transparent state in previous moving image capturing modes, then after the affirmative decision in step S61 is made, steps S62 and S63 may be skipped, and step S64 may be carried out.

If a high-rate moving image capturing mode and a low-rate moving image capturing mode are successively performed in this order (step S61: NO), then in step S71 in FIG. 26, the light resetting operation determiner 214 determines whether or not the light resetting process needs to be performed.

If the frame rate of the moving image capturing mode is higher than the frame rate threshold value Fth depending on the temperature of the photodiodes, then in step S71, the light resetting operation determiner 214 decides that the light resetting process is necessary (step S71: YES), and outputs the decision to the filter controller 216 and the light source controller 218, while also displaying the decision on the display control panel 56. The speaker 58 may also output a sound representative of the decision.

The filter controller 216 applies a voltage to the switching filter 76 to switch the light-regulating mirror film layer 122 from the mirror state to the transparent state. The light source controller 218 energizes the resetting light source 78 to start emitting resetting light 132. In step S72, the resetting light 132 passes through the light-regulating mirror film layer 122 and is applied to the photodetector substrate 72 through the scintillator 74, thereby performing the light resetting process on the photodetector devices 94, i.e., the pixels 190. Thereafter, the light source controller 218 de-energizes the resetting light source 78 in order to finish the light resetting process. In step S73, the filter controller 216 determines whether or not the light-regulating mirror film layer 122 should be switched to the mirror state.

If switching of the light-regulating mirror film layer 122 to the mirror state or the transparent state can sufficiently catch up with the frame rate of the high-rate moving image capturing mode (step S73: YES), then the filter controller 216 applies a voltage, which is opposite in polarity to the voltage applied in step S72, to the switching filter 76, so as to switch the light-regulating mirror film layer 122 from the transparent state to the mirror state in step S74. Thereafter, step S9 and subsequent steps shown in FIG. 17 are carried out.

If switching of the light-regulating mirror film layer 122 to the mirror state or the transparent state cannot catch up with the frame rate of the high-rate moving image capturing mode (step S73: NO), then the filter controller 216 keeps the light-regulating mirror film layer 122 in a transparent state, after which step S9 of FIG. 17 and subsequent steps are carried out.

Further, in step S71, if the frame rate of the moving image capturing mode is lower than the frame rate threshold value Fth dependent on the temperature of the photodiodes, then the light resetting operation determiner 214 determines that the light resetting process is not necessary (step S71: NO), and outputs the decision to the filter controller 216 and to the light source controller 218, while displaying the decision on the display control panel 56.

[7] The radiographic image capturing process according to an image capturing order including two moving image capturing modes having different frame rates, and an image capturing mode for capturing at least one still image (see FIG. 21C) will be described below.

In this case, for example, as shown in FIG. 21C, since the still image capturing mode, the low rate moving image capturing mode, and the high rate moving image capturing mode are carried out in this order, the radiographic image capturing process [4] is applied directly and without modification to switching from the still image capturing mode to the low-rate moving image capturing mode.

Further, the radiographic image capturing process [6] may be applied directly to switching from the low-rate moving image capturing mode to the high rate moving image capturing mode. More specifically, if the light-regulating mirror film layer 122 (see FIG. 6A, FIGS. 9 through 12B, FIG. 13B and FIG. 14B) switches to the mirror state or to the transparent state in one frame after the low-rate moving image capturing mode switches to the high-rate moving image capturing mode, there is a possibility that the switching time may not be able to catch up with the frame rate. Therefore, as shown in FIG. 21C, the light-regulating mirror film layer 122 is switched from the mirror state to the transparent state in advance between image capturing cycles in the low-rate moving image capturing mode, and is kept in the transparent state during the high-rate moving image capturing mode, so that the light resetting process can be performed reliably. In particular, in a high-rate moving image capturing mode carried out on a region of interest (ROI) of the subject 14 (see FIG. 1), noise in the radiographic image can reliably be reduced by performing the light resetting process, while keeping the light-regulating mirror film layer 122 in the transparent state.

With the process [7], not only the case shown in FIG. 21C, but also other cases may be implemented, for example, a case in which image capturing is carried out in order from the high rate moving image capturing mode to the low rate moving image capturing mode and then to the still image capturing mode, or a case in which the still image capturing mode is carried out between the low rate moving image capturing mode and the high rate moving image capturing mode. It is a matter of course that processes [4] through [6] may also be suitably applied with respect to such image capturing modes.

According to the present embodiment, it is determined whether or not the light resetting process is required based on the frame rate and the temperature of the photodiodes. If the light resetting process is carried out on the photodetector devices 94, the photodetector devices 94 are reset, so as to sufficiently embed the impurity level of the photodiodes with electric charges, to thereby eliminate variations in the amount of electric charges discharged from the impurity level between frames due to a rise in temperature of the photodiodes. Owing thereto, if a plurality of images are captured in a moving image capturing mode, etc., the amount of electric charges discharged from the impurity level is made constant in each of the frames. Consequently, in the radiographic image capturing processes [2] through [7], in which a plurality of images are captured on which the light resetting process is carried out, in step S12, the cassette controller 182 or the console 22 may perform an image processing sequence for removing noise caused by a certain amount of discharged electric charges from the radiographic images, i.e., for correcting the radiographic images. Thus, high-quality radiographic images, which are free of noise, can be displayed on the display control panel 56 and the display device 24.

The radiographic image capturing system 10 incorporating therein the electronic cassette 20 according to the present embodiment operates as described above.

Modifications to the Present Embodiment

Modifications to the electronic cassette 20 (electronic cassettes 20A through 20D), and electronic cassettes 20B through 20D according to second through fourth examples, will be described in detail below.

Figure 27A:
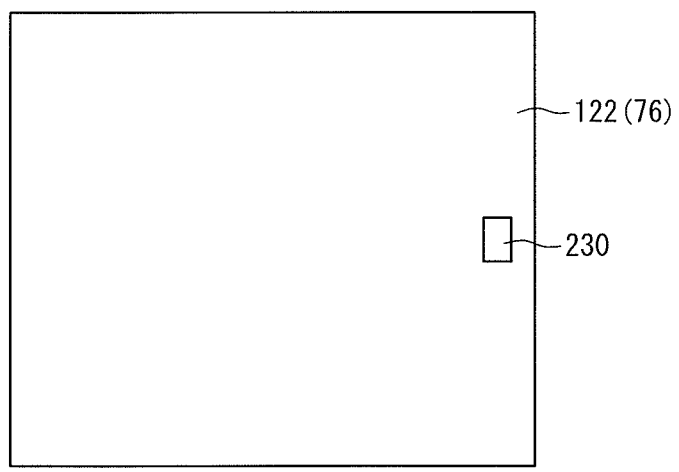
FIG. 27A is a plan view of a window provided on a switching filter.
Figure 27B:
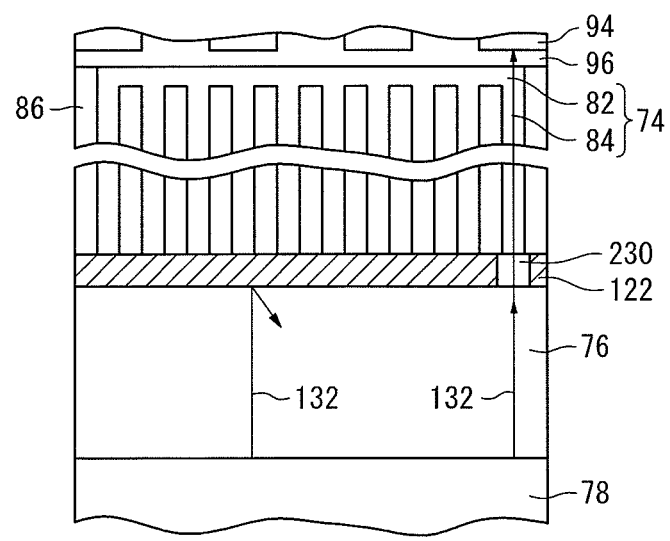
FIG. 27B is a fragmentary view showing the manner in which the switching filter with the window thereon operates.

FIGS. 27A and 27B show a switching filter 76 for detecting the temperature of the photodiodes more accurately and more efficiently.

More specifically, a portion of the light-regulating mirror film layer 122 has a window 230 defined therein for allowing resetting light 132 to pass therethrough at all times. The window 230 should preferably be disposed in a position facing toward a photodetector device 94, which is located in an area the temperature of which is expected to rise. More preferably, the window 230 should be disposed in a position facing toward the photodetector device 94, which is located in an area that is not irradiated with radiation 16.

If the light-regulating mirror film layer 122 is in a mirror state, then in a case where the resetting light source 78 emits resetting light 132, most of the resetting light 132 is reflected toward the resetting light source 78 by the light-regulating mirror film layer 122 in the mirror state. However, a portion of such resetting light 132, which travels toward the window 230, passes through the window 230 and is applied to the scintillator 74, and in addition is applied through the planarization film 96 to a photodetector device 94 (i.e., a photodiode that is not irradiated with radiation 16) that faces toward the window 230.

If the photodetector device 94, which faces toward the window 230, is irradiated with resetting light 132, the photodetector device 94 detects and stores the resetting light 132 as electric charges. As noted previously, since the photodetector device 94 is in the form of the photodiode that is arranged in a location not irradiated with radiation 16, if the stored electric charges are read out as electric signals, the electric signals represent a pixel value depending on a dark current signal. Accordingly, the temperature detector 212 (see FIG. 15) detects the temperature of the photodiode based on the pixel value depending on the dark current signal. The light resetting operation determiner 214 then identifies a frame rate threshold value Fth (see FIG. 20) depending on the detected temperature, and determines whether or not the light resetting process should be carried out based on a comparison between the identified frame rate threshold value Fth and the frame rate of the moving image capturing mode. If the light resetting operation determiner 214 determines that the light resetting process is needed, then the filter controller 216 can switch the light-regulating mirror film layer 122 from the mirror state to the transparent state.

FIGS. 28A through 29B show specific structural details of an electronic cassette 20B according to the second example.

Figure 28A:
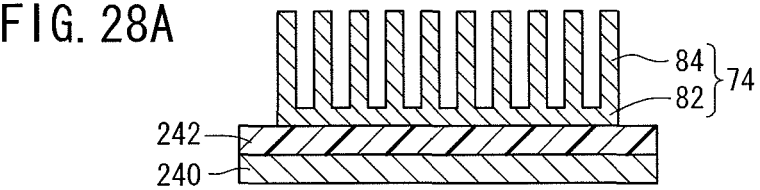
FIG. 28A is a cross-sectional view showing the manner in which a scintillator is formed by film deposition on a vapor deposition substrate.
Figure 28B:
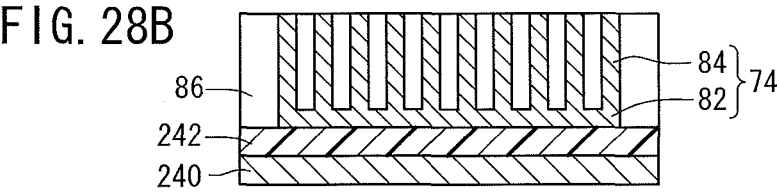
FIG. 28B is a cross-sectional view showing the manner in which a moisture-resistant protective film is formed.
Figure 28C:
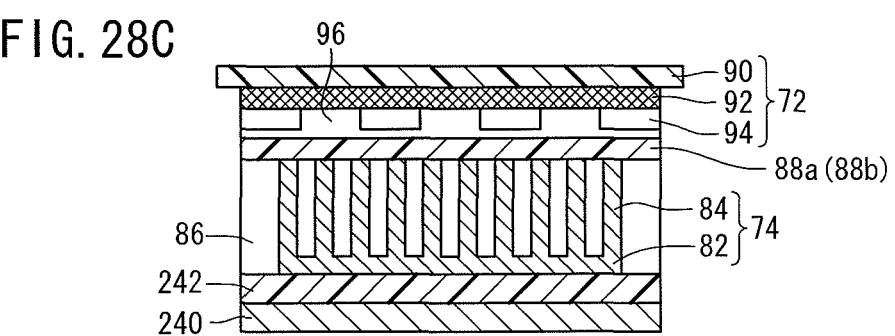
FIG. 28C is a cross-sectional view showing the manner in which the scintillator is bonded or adhered to the photodetector substrate.

First, as shown in FIG. 28A, the scintillator 74 is formed as a film on the vapor deposition substrate 240 with a peel-off layer 242 intervening therebetween. Then, as shown in FIG. 28B, the scintillator 74 is sealed by a moisture-resistant protective layer 86 so as to cover the columns of the columnar crystalline structure 84 with polyparaxylylene, by a CVD (chemical vapor deposition) method. Then, as shown in FIG. 28C, with the photodetector substrate 72 serving as a transfer target, the distal end portion of the scintillator 74 and the photodetector substrate 72 are bonded together by a bonding layer 88a, or are adhered to one another by an adhesive layer 88b. The scintillator 74 may be bonded or adhered (transferred) with respect to the photodetector substrate 72, which serves as a transfer target, according to known transfer techniques.

Figure 29A:
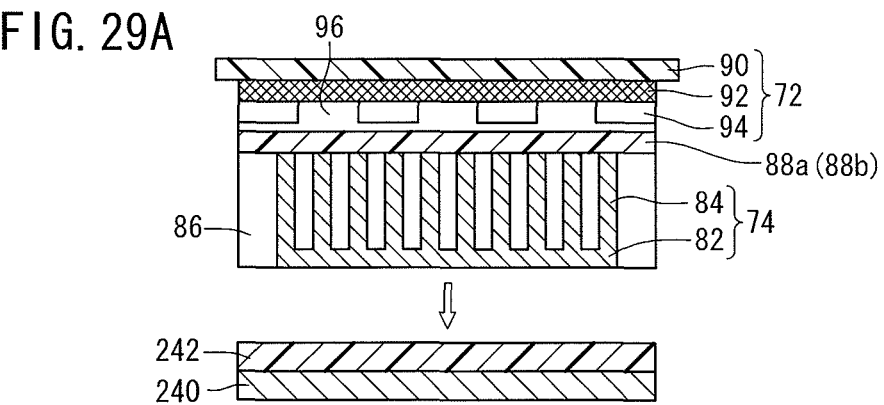
FIG. 29A is a cross-sectional view showing a state in which a vapor deposition substrate and a peel-off layer are peeled off from the scintillator.
Figure 29B:
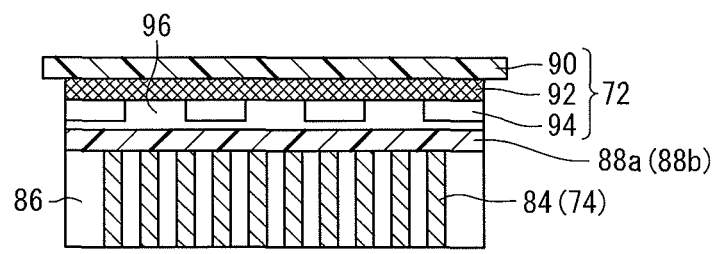
FIG. 29B is a cross-sectional view showing a state in which a base end portion of the scintillator is removed.
Figure 30A:
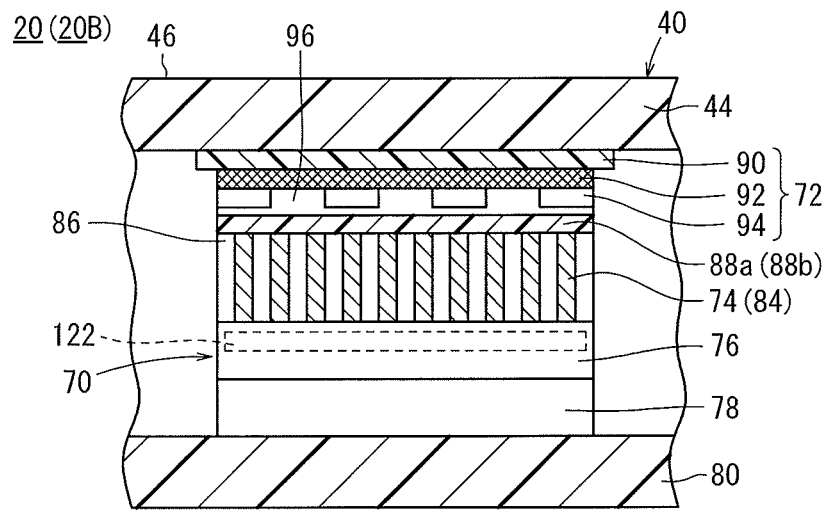
FIGS. 30A and 30B are fragmentary cross-sectional views showing an electronic cassette according to a second example of the present invention in the vicinity of a radiation detector thereof.

Then, as shown in FIG. 29A, the peel-off layer 242 is irradiated with a laser beam, not shown, to peel off the vapor deposition substrate 240 and the peel-off layer 242 from the scintillator 74. Thereafter, as shown in FIG. 29B, the non-columnar crystalline portion 82 of the scintillator is removed, and the photodetector substrate 72, the scintillator 74, the switching filter 76 and the resetting light source 78 are assembled inside the casing 44 in the order shown in FIG. 4B, thereby housing the radiation detector 70 inside the casing 44, as shown in FIG. 30A.

If the vapor deposition substrate 240 is made of a material that is impermeable to resetting light 132, then as shown in FIGS. 28A through 29A, it is necessary to form the scintillator 74 as a film via the peel-off layer 242.

Figure 30B:
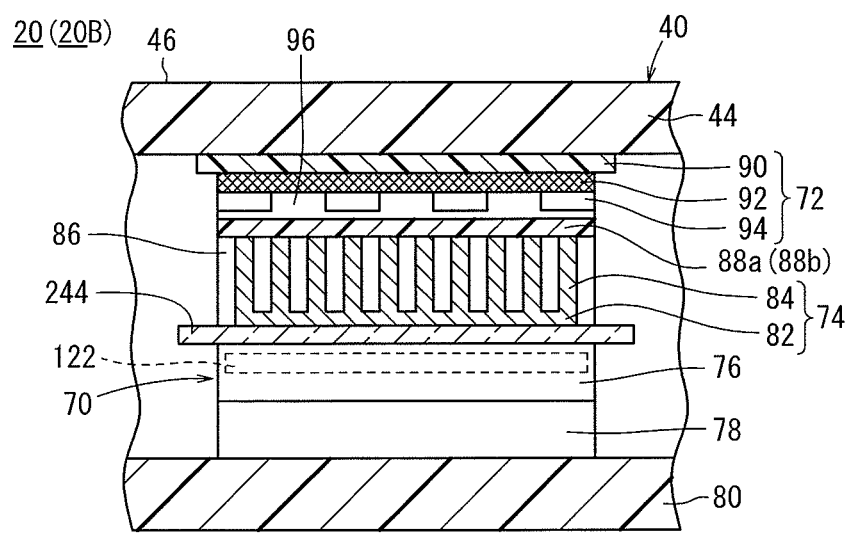

In contrast thereto, if the vapor deposition substrate 244 is made of a material permeable to resetting light 132, then as shown in FIG. 30B, the peel-off layer 242 may be dispensed with, and the scintillator 74 may be formed directly on the vapor deposition substrate 244. In this case, because the non-columnar crystalline portion 82 includes characteristics that cause scattering or reflection of visible light 130, visible light 130 that travels in the direction of the resetting light source 78, together with being reflected by the light-regulating mirror film layer 122 in the mirror state, can also be reflected with higher efficiency toward the photodetector substrate 72.

Apart from a glass substrate, a light-permeable and flexible plastic film, such as a polyimide film, a polyarylate film, a biaxially elongated polystyrene film, an aramid film, or a film of bionanofibers, may be used as the vapor deposition substrate 244, which is transparent with respect to the resetting light 132.

Figure 31:
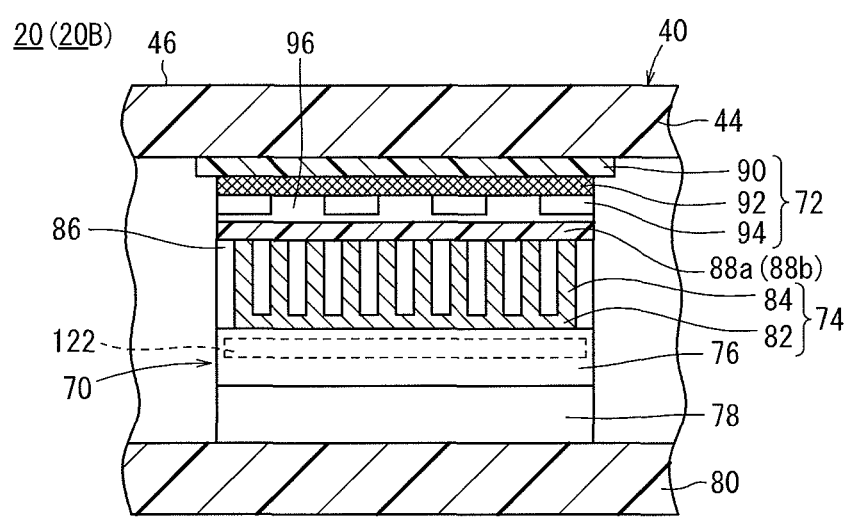
FIG. 31 is a fragmentary cross-sectional view showing an electronic cassette according to a second example in the vicinity of a radiation detector thereof.

Further, as shown in FIG. 31, the vapor deposition substrate 244 may be dispensed with, and the non-columnar crystalline portion 82 and the switching filter 76 may be held in contact with each other. In this manner, reflection of visible light 130 as mentioned above can be performed more efficiently.

As shown in FIGS. 4B and 30A through 31, apart from the photodetector substrate 72 and the scintillator 74 being bonded together by the bonding layer 88a or being adhered to each other through the adhesive layer 88b, the electronic cassette 20B according to the second example is substantially the same in structure as the electronic cassette 20A according to the first example (see FIG. 6A), and therefore, the aforementioned cases [1] through [7] can be applied thereto directly without modification.

Further, in the descriptions of FIGS. 28A through 31, a case has been explained in which the scintillator 74 is formed having the non-columnar crystalline portion 82. However, in the second example, after vapor deposition conditions have been determined such that the non-columnar crystalline portion 82 is not formed, the scintillator 74 may be vapor deposited on the vapor deposition substrate 240 in accordance with such conditions. In this manner, light scattering by the non-columnar crystalline portion 82 can be avoided.

Figure 32A:
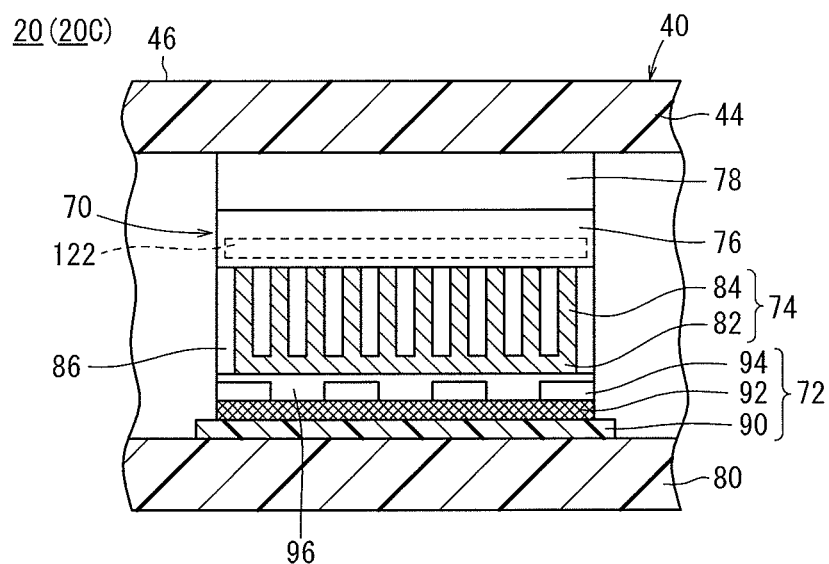
FIG. 32A is a fragmentary cross-sectional view showing an electronic cassette according to a third example in the vicinity of a radiation detector thereof.
Figure 32B:
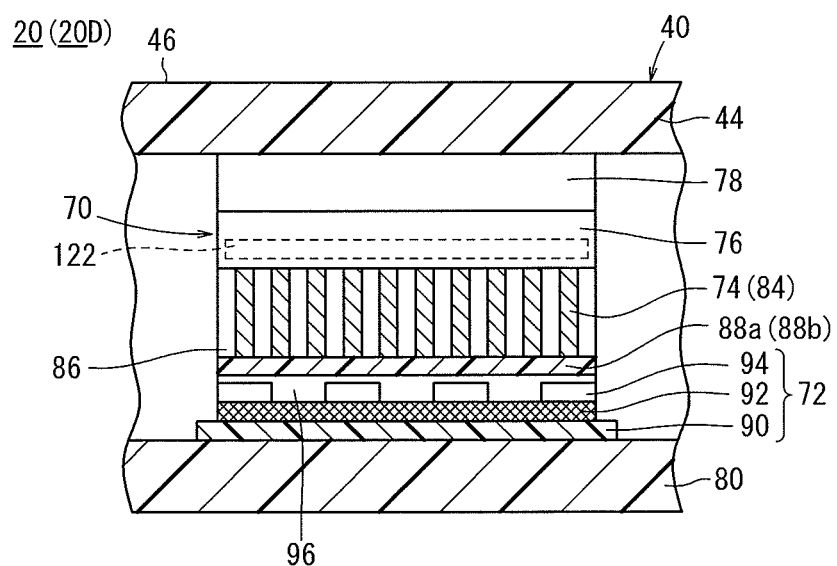
FIG. 32B is a fragmentary cross-sectional view showing an electronic cassette according to a fourth example in the vicinity of a radiation detector thereof.

FIGS. 32A and 32B are fragmentary cross-sectional views showing electronic cassettes 20C and 20D according to third and fourth examples, in the vicinity of the radiation detector 70. The electronic cassettes 20C and 20D according to the third and fourth examples differ from the electronic cassettes 20A and 20B according to the first and second examples (see FIGS. 6A and 30A), in that the radiation detector 70 is vertically reversed or turned upside down.

With the electronic cassettes 20C and 20D according to the third and fourth examples, radiation 16 that has passed through the subject 14 (see FIG. 1) reaches the scintillator 74 via the resetting light source 78 and the switching filter 76, the scintillator 74 converts the radiation into visible light 130 (see FIGS. 11A and 11B), and the photodetector substrate 72 converts the visible light 130 into electric signals. In this case, since the resetting light source 78 is arranged on the side of the irradiation surface 46 in the casing 44, there is a concern that resetting light 132 could be generated in error as a result of the resetting light source 78 being irradiated with radiation 16.

Thus, with the electronic cassettes 20C and 20D according to the third and fourth examples, if the light-regulating mirror film layer 122 is in a mirror state at least during application of radiation 16 thereto, since resetting light 132, which is generated in error, is reflected toward the resetting light source 78 by the light-regulating mirror film layer 122, application of such resetting light 132 to the photodetector substrate 72 is blocked, and blurring of radiographic images can be prevented. In addition, by setting the light-regulating mirror film layer 122 in a mirror state, visible light 130, which travels in the direction of the resetting light source 78, can be reflected toward the photodetector substrate 72, and as a result, sensitivity of the photodetector devices 94 of the photodetector substrate 72 with respect to visible light 130 can be enhanced.

In the electronic cassettes 20C and 20D according to the third and fourth examples, because it is necessary for the light-regulating mirror film layer 122 to be set in the mirror state at least upon application of radiation 16, cases [1] through [7] can be applied only with respect to operations in which the light-regulating mirror film layer 122 can be kept in the mirror state during application of radiation 16.

Advantages of the Present Embodiment

As described above, with the electronic cassette 20 (20A through 20D) according to the present embodiment, if the switching filter 76 is switched to the transparent state with respect to resetting light 132, the resetting light source 78 can apply resetting light 132 to the photodetector substrate 72 through the switching filter 76 and the scintillator 74, for thereby sufficiently performing a light resetting process on the photodetector substrate 72.

On the other hand, if the switching filter 76 is switched to the mirror state with respect to resetting light 132, among the fluorescence (i.e., visible light 130) that is converted from radiation 16 by the scintillator 74, part of such fluorescence that is directed toward the resetting light source 78 is reflected toward the photodetector substrate 72 by the switching filter 76, and the reflected light (visible light 130) travels through the scintillator 74 without passing through the resetting light source 78, and is applied to the photodetector substrate 72. Owing thereto, high-quality radiographic images, which are not blurred, can be obtained, and the amount of visible light 130 applied to the photodetector substrate 72 is increased, thereby increasing the sensitivity of the photodetector substrate 72 with respect to visible light 130.

According to the present embodiment, therefore, since the photodetector substrate 72, the scintillator 74, the switching filter 76, and the resetting light source 78 are successively arranged in this order, and the switching filter 76 is selectively permeable and impermeable to resetting light 132, the light resetting process can sufficiently be performed on the photodetector substrate 72, and the sensitivity of the photodetector substrate 72 with respect to visible light 130 can be increased, while blurring of radiographic images can be suppressed.

Further, based on the image capturing order, the switching filter 76 can be switched to the transparent state (permeable state) for passing resetting light 132 therethrough, or the mirror state (impermeable state) for reflecting visible light 130 toward the photodetector substrate 72 as well as reflecting resetting light 132 toward the resetting light source 78. Therefore, the switching filter 76 can be kept in a transparent state or in a mirror state, or switched to a transparent state or a mirror state, depending on the image capturing method (a still image capturing mode or a moving image capturing mode) for the subject 14, thereby reliably and efficiently performing the light resetting process on the photodetector substrate 72, and acquiring, with high sensitivity, high-quality radiographic images, which are prevented from becoming blurred. If the switching filter 76 in the mirror state reflects visible light 130 toward the photodetector substrate 72, the amount of visible light 130 applied to the photodetector substrate 72 is increased. Consequently, the amount of radiation 16 that is applied to the subject 14 can be reduced, thereby reducing the exposure dose of radiation 16 applied to the subject 14.

More specifically, if the image capturing order includes a radiographic image capturing mode for capturing at least one radiographic image, or a moving image capturing mode having a frame rate lower than the frame rate threshold value Fth (or Fth0), i.e., a low-rate moving image capturing mode, then the switching filter 76 may be kept in the mirror state.

The above image capturing modes, in particular, require high-quality radiographic images to be acquired with high sensitivity. Since the image capturing interval in such image capturing modes is relatively long, the temperature of the photodiodes does not rise significantly, and noise caused if electric charges trapped by the impurity level are discharged again is not expected to greatly affect the captured radiographic images.

Consequently, if the above image capturing order is received, the switching filter 76 is kept in a mirror state so that the light resetting process is not carried out, and also so that visible light 130, which is converted from radiation 16 by the scintillator 74, is reflected toward the photodetector substrate 72, thereby increasing the amount of visible light 130 applied to the photodetector substrate 72. As a result, it is possible to easily acquire low-noise, high-quality radiographic images, which are prevented from becoming blurred, with high sensitivity.

Further, if the image capturing order includes a moving image capturing mode, and in particular, a high-rate moving image capturing mode, then the switching filter 76 may be kept in a transparent state.

In the case of the moving image capturing mode, the temperature of the photodiodes tends to increase due to image capturing taking place over a long period of time, and it can be expected that noise caused by electric charges, which become trapped by the impurity level, being discharged again may impart a significant adverse influence on the radiographic images. Accordingly, by keeping the switching filter 76 in the transparent state, resetting can be performed during times in which radiation 16 is not being applied between respective image capturing events, and as a result, the presence of noise in the radiographic images can be reduced.

Further, if the image capturing order includes a moving image capturing mode, and in particular, a high-rate moving image capturing mode, then the switching filter 76 is kept in a mirror state during each frame in which the subject 14 is irradiated with radiation 16, and is kept in a transparent state during each frame in which the subject 14 is not irradiated with radiation 16. Accordingly, the switching filter 76 is switched successively between the mirror state and the transparent state.

In this case, since the switching filter 76 is switched successively between the mirror state and the transparent state within one frame, during times that the subject 14 is irradiated with radiation 16, the switching filter 76 is kept in a mirror state to reflect visible light 130 reliably toward the photodetector substrate 72, thereby increasing the amount of visible light 130 applied to the photodetector substrate 72. During times that the subject 14 is not irradiated with radiation 16, the switching filter 76 is kept in a transparent state to thereby sufficiently perform the light resetting process on the photodetector substrate 72.

In the moving image capturing mode, therefore, the switching filter 76 is switched alternately between the mirror state and the transparent state within one frame in order to acquire high-quality radiographic images with high sensitivity, and also to reduce noise in the acquired radiographic images. For enabling such a successive switching state between the mirror state and the transparent state, it is necessary to provide a switching filter 76 that can realize a switching time, which is capable of catching up sufficiently with the frame rate of the moving image capturing mode (i.e., a switching filter 76 having a switching time shorter than the time interval between image capturing cycles). Accordingly, with a switching filter 76, the sensitivity of which is incapable of catching up with the frame rate, the transparent state should be maintained.

Furthermore, in the case of an image capturing order including a moving image capturing mode (high rate moving image capturing mode, low rate moving image capturing mode) and a still image capturing mode for capturing at least one still image, the switching filter 76 may keep the transparent state during the moving image capturing mode, may keep the mirror state during the still image capturing mode, and may switch from the transparent state to the mirror state at a timing at which the moving image capturing mode is switched to the still image capturing mode, or alternatively, may switch from the mirror state to the transparent state at a timing at which the still image capturing mode is switched to the moving image capturing mode.

In this manner, by switching the state of the switching filter 76 at a timing at which the image capturing method is changed, optimal radiographic images corresponding to the image capturing method can be acquired.

Still further, in the case of an image capturing order including a high rate moving image capturing mode and a still image capturing more for capturing at least one still image, the switching filter 76 keeps the mirror state during the still image capturing mode, whereas in each frame in the high rate moving image capturing mode, the switching filter 76 keeps the mirror state during application of radiation 16 with respect to the subject 14, and keeps the transparent state at times that radiation 16 is not being applied with respect to the subject 14. Thereby, the switching filter 76 switches successively between the mirror state and the transparent state, and may switch from a state of switching successively between the mirror state and the transparent state to the mirror state at a timing at which the high rate moving image capturing mode is switched to the still image capturing mode, or alternatively, may switch from the mirror state to a state of switching successively between the mirror state and the transparent state at a timing at which the still image capturing mode is switched to the moving image capturing mode.

With this type of switching order as well, since the state of the switching filter 76 is switched reliably at a timing at which the image capturing method is changed, optimal radiographic images corresponding to the image capturing method can be acquired.

Further, in the case of an image capturing order including a low rate moving image capturing mode and a high rate moving image capturing mode, the switching filter 76 is kept in the mirror sate during the low rate moving image capturing mode, is kept in the transparent state during the high rate moving image capturing mode, and may be switched from the mirror state to the transparent state at a timing at which the low rate moving image capturing mode is switched to the high rate moving image capturing mode, or alternatively, may be switched from the transparent state to the mirror state at a timing at which the high rate moving image capturing mode is switched to the low rate moving image capturing mode.

In this manner, even if the frame rate of the image capturing order is changed during the radiographic image capturing process, optimum radiographic images depending on the frame rate can reliably be acquired by switching the switching filter 76 at a timing at which the frame rate is changed.

Further, in the case of an image capturing order including a low rate moving image capturing mode and a high rate moving image capturing mode, the switching filter 76 is kept in the mirror state during the low rate moving image capturing mode, and together therewith, is kept in the mirror state at times that radiation 16 is applied with respect to the subject 14, and is kept in the transparent state at times that radiation 16 is not applied with respect to the subject 14 in each frame in the high rate moving image capturing mode. Thereby, the switching filter 76 switches successively between the mirror state and the transparent state, and may switch from the mirror state to a state of successively switching between the mirror state and the transparent state at a timing a which the low rate moving image capturing mode is switched to the high rate moving image capturing mode, or alternatively, may switch from the state of successively switching between the mirror state and the transparent state to the mirror state at a timing at which the high rate moving image capturing mode is switched to the low rate moving image capturing mode.

Even with an image capturing order in which the frame rate changes during image capturing, assuming that the state of the switching filter is switched at a timing at which the frame rate changes, optimal radiographic images can be acquired reliably corresponding to the frame rate.

Further, in the case of an image capturing order including a low rate moving image capturing mode and a high rate moving image capturing mode, if the switching order includes an image capturing sequence of a low rate moving image capturing mode and a high rate moving image capturing mode in this order, the switching filter 76 may be switched to the transparent state after having been maintained in the mirror state up to a predetermined number of frames in the low rate moving image capturing mode, and then may be kept in the transparent state for any frames remaining after switching and in the high rate moving image capturing mode, or alternatively, if the switching order includes an image capturing sequence of a high rate moving image capturing mode and a low rate moving image capturing mode in this order, the switching filter 76 may be switched to the mirror state after having been maintained in the transparent state in the high rate moving image capturing mode and up to a predetermined number of frames in the low rate moving image capturing mode, and then may be kept in the mirror state for any frames remaining after switching.

Due to the fact that time is required for switching between the mirror state and the transparent state, cases may occur in which switching between the mirror state and the transparent state cannot be smoothly carried out at the timing at which switching takes place between the low rate moving image capturing mode and the high rate moving image capturing mode. Thus, in the foregoing manner, by carrying out switching between the mirror state and the transparent state during the low rate moving image capturing mode, superimposition of noise in the radiographic images, caused by charges becoming trapped in the impurity level and then being released again in the high rate moving image capturing mode, can reliably be avoided.

In the case of an image capturing order including, in addition to the two types of moving image capturing modes, a still image capturing mode for capturing at least one still image, the switching filter 76 keeps the mirror state in the still image capturing mode, and may be switched from a state in which the switching filter 76 corresponds to the moving image capturing mode to the mirror state at a timing at which the moving image capturing mode is switched to the still image capturing mode, or alternatively, may be switched from the mirror state to the state in which the switching filter 76 corresponds to the moving image capturing mode at a timing at which the still image capturing mode is switched to the moving image capturing mode.

In this manner, even if the image capturing order includes a still image capturing mode, optimum radiographic images can easily be acquired during each of the image capturing modes, by switching the switching filter 76 as described above.

With the electronic cassette 20, the photodetector substrate 72 includes the photodetector devices 94 for converting visible light 130 into electric signals, and the switching filter 76 includes the window 230, which is defined in a portion for passing resetting light 132 therethrough at all times. If the resetting light source 78 applies resetting light 132 through the window 230 to one of the photodetector devices 94, which faces toward the window 230, the photodetector device 94, which is irradiated with resetting light 132, detects a dark current signal generated by the resetting light 132. The switching filter 76 may switch to the mirror state or to the transparent state based on the temperature of the photodetector devices 94, depending on the dark current signal and the image capturing order.

The level of noise trapped by the impurity level varies with the temperature of the photodetector devices 94 in the form of photodiodes. Therefore, it is desirable to change the frame rate threshold value Fth depending on the temperature of the photodetector devices 94. Therefore, as described above, noise can be reduced efficiently depending on a change in temperature of the photodetector devices 94, by switching the switching filter 76 into a mirror state or a transparent state based on the temperature, and depending on the dark current signal and the image capturing order.

According to the present embodiment, unlike conventional processes, it is determined whether or not the light resetting process is required based on the frame rate and the temperature of the photodiodes. If a light resetting process is performed, a sufficient amount of electric charge is embedded in the impurity level to thereby eliminate variations in the amount of electric charge discharged from the impurity level between frames due to a rise in the temperature of the photodiodes. As a consequence, noise due to electric charges discharged at a certain rate can be removed (corrected) from the radiographic images by way of an image processing sequence, thus making it possible to acquire radiographic images of higher quality.

Further, the switching filter 76 includes the light-regulating mirror film layer 122, which is controlled electrically to be permeable or impermeable to resetting light 132. The scintillator 74 is disposed on the side of the light-regulating mirror film layer 122, whereas the resetting light source 78 is disposed on the side of the transparent base 110. Therefore, the switching filter 76 can easily and efficiently be switched to a permeable state or an impermeable state (mirror state).

The resetting light source 78 is in the form of an array of light-emitting elements 142, a backlight, or an electroluminescent light source, disposed in facing relation to the photodetector substrate 72 with the switching filter 76 and the scintillator 74 interposed therebetween.

In this case, the resetting light source 78, which is in the form of a backlight, makes it possible to place the cold-cathode ray tube 152 and the light-emitting elements 162 in an area that is not irradiated with radiation 16. Therefore, the cold-cathode ray tube 152 and the light-emitting elements 162 are prevented from becoming degraded by radiation 16. If the resetting light source 78 is in the form of an organic electroluminescent light source, then the resetting light source 78 may be made low in profile.

Further, if the photodetector devices 94 of the photodetector substrate 72 are made of an organic photoconductor or an amorphous oxide semiconductor, and the TFTs 92 are made of an organic semiconductor, an amorphous oxide semiconductor, or carbon nanotubes, then the photodetector devices 94 and the TFTs 92 can be deposited as films at low temperatures.

The oblique light blocking layer 102 is interposed between the photodetector substrate 72 and the scintillator 74, thereby making it possible to increase sensitivity of the photodetector substrate 72 with respect to visible light 130, and to prevent radiographic images from becoming blurred.

The present invention is not limited to the illustrated details of the present embodiment, but various process modifications may be made to the illustrated processes, as follows.

More specifically, according to the radiographic image capturing processes [1] through [7], the light resetting operation determiner 214 determines whether or not the light resetting process needs to be performed on the photodetector devices 94 based on the magnitude of the frame rate relative to the frame rate threshold value Fth. However, the light resetting operation determiner 214 may also determine whether or not the light resetting process needs to be performed according to any one of the following processes (1) through (3).

(1) The light resetting operation determiner 214 determines that the light resetting process needs to be performed if the number of captured images exceeds a predetermined threshold value during the moving image capturing mode.

(2) Since the noise level in the radiographic image increases as the temperature of the photodetector devices 94 rises, the light resetting operation determiner 214 may determine that the light resetting process needs to be performed, if the noise level of an acquired radiographic image exceeds a predetermined threshold value.

(3) In the radiographic image capturing process [6], if the high-rate moving image capturing mode and the low-rate moving image capturing mode are successively carried out in this order, i.e., if a high frame rate changes to a low frame rate in the moving image capturing mode, it may not necessarily be decided that the light resetting process is not required because of the low frame rate. In other words, the temperature of the photodetector devices 94 may possibly be increased if the light resetting process is repeatedly performed on the photodetector devices 94 during the high-rate moving image capturing mode. Accordingly, the light resetting operation determiner 214 may decide that the light resetting process needs to be performed in order to eliminate adverse effects of the high-rate moving image capturing mode.

The light resetting operation determiner 214 may determine whether or not the light resetting process needs to be performed according to the processes (1) through (3), instead of determining whether the light resetting process needs to be performed based on the frame rate. The light resetting operation determiner 214 may also determine whether or not the light resetting process needs to be performed based on a combination of the frame rate and any one of the processes (1) through (3). Furthermore, the light resetting operation determiner 214 may determine whether or not the light resetting process needs to be performed based on a combination of the frame rate and all of the processes (1) through (3).

Although certain preferred embodiments of the present invention have been shown and described in detail, it should be understood that various changes and modifications may be made to the embodiments without departing from the scope of the invention as set forth in the appended claims.

What is claimed is:

1. A radiographic image capturing apparatus comprising:
 a scintillator for converting radiation into fluorescence;
 a photodetector substrate for converting the fluorescence into electric signals;

a resetting light source for applying resetting light to the photodetector substrate; and a switching filter, which is selectively permeable and impermeable to the resetting light, wherein the photodetector substrate, the scintillator, the switching filter, and the resetting light source are arranged in this order, and if the switching filter is made permeable to the resetting light, the switching filter allows the resetting light to be applied to the photodetector substrate through the scintillator, and if the switching filter is made impermeable to the resetting light, the switching filter reflects at least the fluorescence toward the photodetector substrate.

2. The radiographic image capturing apparatus according to claim 1, wherein:

the scintillator converts the radiation, which has passed through a subject, into the fluorescence;

the photodetector substrate converts the fluorescence into the electric signals, which represent a radiographic image of the subject; and the switching filter is selectively switchable to a transparent state, which is permeable to the resetting light, and a mirror state, which reflects the fluorescence toward the photodetector substrate and also reflects the resetting light toward the resetting light source, based on an image capturing order concerning capturing of the radiographic image of the subject.

3. The radiographic image capturing apparatus according to claim 2, wherein if the image capturing order includes a still image capturing mode for capturing at least one still image or a moving image capturing mode at a frame rate lower than a frame rate threshold value, the switching filter is kept in the mirror state.

4. The radiographic image capturing apparatus according to claim 2, wherein if the image capturing order includes a moving image capturing mode, the switching filter is kept in the transparent state.

5. The radiographic image capturing apparatus according to claim 2, wherein if the image capturing order includes a moving image capturing mode, the switching filter is kept in the mirror state in each frame while the subject is irradiated with radiation, and is kept in the transparent state if the subject is not irradiated with radiation, whereby the switching filter is switched successively between the mirror state and the transparent state.

6. The radiographic image capturing apparatus according to claim 2, wherein if the image capturing order includes a moving image capturing mode and a still image capturing mode for capturing at least one still image, the switching filter is kept in a transparent state in the moving image capturing mode, and is kept in the mirror state in the still image capturing mode, and further is switched from the transparent state to the mirror state at a timing at which the moving image capturing mode is switched to the still image capturing mode, or the switching filter switches from the mirror state to the transparent state at a timing at which the still image capturing mode is switched to the moving image capturing mode.

7. The radiographic image capturing apparatus according to claim 2, wherein if the image capturing order includes a moving image capturing mode at a frame rate higher than a frame rate threshold value, and a still image capturing mode for capturing at least one still image, the switching filter is kept in the mirror state during the still image capturing mode, is further kept in the mirror state during application of radiation with respect to the subject in each frame during the moving image capturing mode, and is kept in the transparent state at times that radiation is not being applied with respect to the subject, whereby switching between the mirror state and the transparent state is carried out successively, and the switching filter is switched to the mirror state from a state in which the switching filter is switched successively between the mirror state and the transparent state at a timing at which the moving image capturing mode is switched to the still image capturing mode, or is switched from the mirror state to the state in which the switching filter is switched successively between the mirror state and the transparent state at a timing at which the still image capturing mode is switched to the moving image capturing mode.

8. The radiographic image capturing apparatus according to claim 2, wherein if the image capturing order includes a first moving image capturing mode at a frame rate lower than a frame rate threshold value and a second moving image capturing mode at a frame rate higher than the frame rate threshold value, the switching filter is kept in the mirror state during the first moving image capturing mode, and is kept in the transparent state during the second image capturing mode, and the switching filter switches from the mirror state to the transparent state at a timing at which the first moving image capturing mode is switched to the second moving image capturing mode, or switches from the transparent state to the mirror state at a timing at which the second moving image capturing mode is switched to the first moving image capturing mode.

9. The radiographic image capturing apparatus according to claim 2, wherein if the image capturing order includes a first moving image capturing mode at a frame rate lower than a frame rate threshold value and a second moving image capturing mode at a frame rate higher than the frame rate threshold value, the switching filter is kept in the mirror state in the first moving image capturing mode, or is kept in the mirror state while the subject is irradiated with the radiation and is kept in the transparent state while the subject is not irradiated with the radiation in each frame in the second moving image capturing mode, whereby the switching filter is switched successively between the mirror state and the transparent state; and the switching filter switches from the mirror state to successively switching between the mirror state and the transparent state at a timing at which the first moving image capturing mode is switched to the second moving image capturing mode, or switches from successively switching between the mirror state and the transparent state to the mirror state at a timing at which the second moving image capturing mode is switched to the first moving image capturing mode.

10. The radiographic image capturing apparatus according to claim 2, wherein if the image capturing order includes a first moving image capturing mode at a frame rate lower than a frame rate threshold value and a second moving image capturing mode at a frame rate higher than the frame rate threshold value, if the image capturing order includes an image capturing sequence in order of the first image capturing mode and the second image capturing mode, the switching filter is switched to the transparent state after the mirror state has been maintained until a predetermined frame in the first image capturing mode, and then maintains the transparent state for any remaining frames after switching and in the second image capturing mode, and if the image capturing order includes an image capturing sequence in order of the second image capturing mode and the first image capturing mode, the switching filter is switched to the mirror state after the transparent state has been maintained in the second image capturing mode and until a predetermined frame in the first image capturing mode, and then maintains the mirror state for any remaining frames after switching.

11. The radiographic image capturing apparatus according to claim 8, wherein if the image capturing order further includes a still image capturing mode for capturing at least one still image, the switching filter is kept in the mirror state in the still image capturing mode, and switches from a state corresponding to the moving image capturing modes to the mirror state, at a timing at which the moving image capturing modes is switched to the still image capturing mode, or switches from the mirror state to the state corresponding to the moving image capturing modes, at a timing at which the still image capturing mode is switched to the moving image capturing modes.

12. The radiographic image capturing apparatus according to claim 2, wherein the photodetector substrate includes a plurality of photodetector devices for converting the fluorescence into the electric signals;
   the switching filter has a window defined in a portion thereof for passing the resetting light therethrough at all times;
   if the resetting light source applies the resetting light through the window to one of the photodetector devices, which faces toward the window, the photodetector device, which is irradiated with the resetting light, detects a dark current signal generated by the resetting light; and
   the switching filter switches to the mirror state or the transparent state based on a temperature of the photodetector device depending on the dark current signal and the image capturing order.

13. The radiographic image capturing apparatus according to claim 1, wherein the switching filter includes a light-regulating mirror film layer, which is electrically controlled to be permeable or impermeable to the resetting light.

14. The radiographic image capturing apparatus according to claim 13, wherein the switching filter includes a transparent base permeable to the resetting light, and the light-regulating mirror film layer is disposed on the transparent base; and
   the scintillator is disposed on a side of the light-regulating mirror film layer, and the resetting light source is disposed on a side of the transparent base.

15. The radiographic image capturing apparatus according to claim 1, wherein the resetting light source comprises an array of light-emitting elements, a backlight, or an electroluminescent light source, disposed in facing relation to the photodetector substrate with the switching filter and the scintillator interposed therebetween.

16. The radiographic image capturing apparatus according to claim 15, wherein the backlight comprises a light guide plate disposed on a side of the switching filter remote from the scintillator, a light source disposed on a side of the light guide plate, a reflective sheet disposed in surrounding relation to the light guide plate and the light source, and a diffusion sheet disposed on a surface of the light guide plate, which faces toward the switching filter;
   the light source applies light to the light guide plate; and
   the light applied to the light guide plate is repeatedly reflected in the light guide plate between surfaces of the reflective sheet and the diffusion sheet, and thereafter, the light is emitted as the resetting light from the diffusion sheet to the switching filter.

17. The radiographic image capturing apparatus according to claim 16, wherein the light source comprises a light-emitting diode or a cold-cathode ray tube.

18. The radiographic image capturing apparatus according to claim 15, wherein the electroluminescent light source comprises an organic electroluminescent light source.

19. The radiographic image capturing apparatus according to claim 1, further comprising:
   an oblique light blocking layer for blocking the fluorescence or the resetting light that travels obliquely to a direction in which the radiation is applied, the oblique light blocking layer being interposed between the photodetector substrate and the scintillator.

20. The radiographic image capturing apparatus according to claim 1, wherein the photodetector substrate, the scintillator, the switching filter, and the resetting light source, are successively arranged in this order, or alternatively, the resetting light source, the switching filter, the scintillator, and the photodetector substrate are successively arranged in this order, along a direction in which radiation is applied.

21. The radiographic image capturing apparatus according to claim 20, wherein if the resetting light source, the switching filter, the scintillator, and the photodetector substrate are successively arranged in this order along the direction in which radiation is applied, the switching filter is kept in the mirror state, for thereby reflecting the resetting light toward the resetting light source while reflecting the fluorescence toward the photodetector substrate, at least during times that the radiation is applied.

* * * * *